(12) United States Patent
Shah et al.

(10) Patent No.: US 11,806,135 B2
(45) Date of Patent: Nov. 7, 2023

(54) IN VIVO SENSING AND INFUSION DEVICES

(71) Applicant: Percusense, Inc., Valencia, CA (US)

(72) Inventors: Rajiv Shah, Ranchos Palos Verdes, CA (US); Ellen Messer, Pasadena, CA (US); Katherine Wolfe, Dunwoody, GA (US); Shaun Pendo, Wofford Heights, CA (US)

(73) Assignee: PercuSense, Inc., Valencia, CA (US)

( * ) Notice: Subject to any disclaimer, the term of this patent is extended or adjusted under 35 U.S.C. 154(b) by 191 days.

(21) Appl. No.: 17/406,244

(22) Filed: Aug. 19, 2021

(65) Prior Publication Data

US 2022/0248987 A1 Aug. 11, 2022

Related U.S. Application Data

(63) Continuation of application No. 15/455,115, filed on Mar. 9, 2017, now abandoned, and a continuation-in-part of application No. 15/417,055, filed on Jan. 26, 2017, now Pat. No. 10,888,281.

(60) Provisional application No. 62/353,559, filed on Jun. 23, 2016.

(51) Int. Cl.
| | |
|---|---|
| *A61B 5/1473* | (2006.01) |
| *A61B 5/145* | (2006.01) |
| *A61B 5/1486* | (2006.01) |
| *A61B 5/00* | (2006.01) |
| *A61M 5/172* | (2006.01) |
| *A61M 5/142* | (2006.01) |

(52) U.S. Cl.
CPC ........ *A61B 5/14532* (2013.01); *A61B 5/1473* (2013.01); *A61B 5/14865* (2013.01); *A61B 5/6852* (2013.01); *A61M 5/14276* (2013.01); *A61M 5/1723* (2013.01); *A61B 2560/0406* (2013.01); *A61B 2560/063* (2013.01); *A61M 2230/201* (2013.01)

(58) Field of Classification Search
CPC .............. A61B 5/14532; A61B 5/1473; A61B 5/14865; A61B 5/6852; A61B 2560/0406; A61B 2560/063; A61B 5/746; A61B 2560/0214; A61B 2562/0219; A61B 5/14542; A61B 5/14546; A61B 5/412; A61B 5/7275; A61B 5/0002; A61B 5/01; A61B 5/11; A61M 5/14276; A61M 5/1723; A61M 2230/201; A61M 5/172; A61M 2005/1726; G16H 40/67
See application file for complete search history.

(56) References Cited

U.S. PATENT DOCUMENTS

| | | | | |
|---|---|---|---|---|
| 5,390,671 | A * | 2/1995 | Lord | ........... A61B 17/3403 600/347 |
| 7,003,336 | B2 * | 2/2006 | Holker | ........... A61B 5/14865 600/347 |
| 2012/0277667 | A1 * | 11/2012 | Yodat | ........... A61B 5/1451 604/65 |

* cited by examiner

*Primary Examiner* — Andrey Shostak
(74) *Attorney, Agent, or Firm* — PercuSense, Inc.

(57) ABSTRACT

Sensing and infusion devices are described. In one embodiment, a sensing and infusion device may include an implantable segment having a sensor. The sensing and infusion device may also include a catheter, and a sensor channel may be formed in the catheter. The sensor channel may be configured to retain at least a portion of the implantable segment.

10 Claims, 47 Drawing Sheets

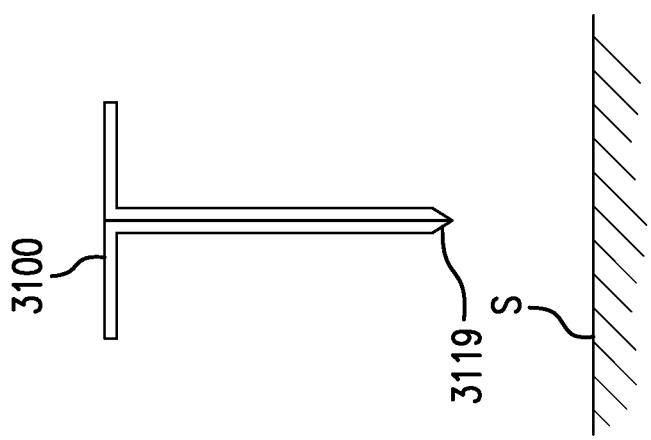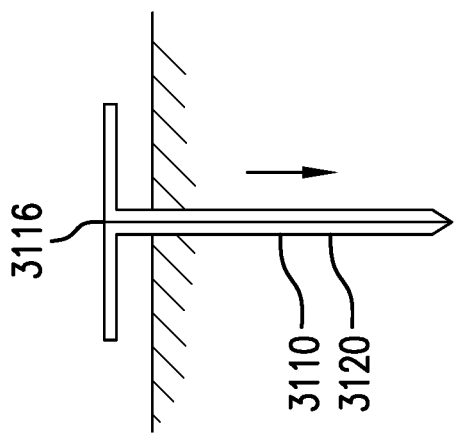
FIG.18A
FIG.18B

IN VIVO SENSING AND INFUSION DEVICES

CROSS-REFERENCE TO RELATED APPLICATIONS

This application is a continuation application that claims the benefit under 35 U.S.C. 120 of U.S. patent application Ser. No. 15/455,115 filed on Mar. 9, 2017 which further claims priority from U.S. provisional application Nos.: 62/336,482, filed May 13, 2016; 62/348,806, filed Jun. 10, 2016; 62/370,226, filed Aug. 2, 2016; 62/383,233, filed Sep. 2, 2016; 62/401,481, filed Sep. 29, 2016; 62/443,070, filed Jan. 6, 2017; and 62/451,545, filed Jan. 27, 2017. This application is continuation-in-part of U.S. patent application Ser. No. 15/417,055, filed Jan. 26, 2017, which claims the benefit of U.S. provisional application No. 62/353,559, filed Jun. 23, 2016. The applications listed above are hereby incorporated by reference in their entireties.

BACKGROUND

Diabetes and other diseases may be treated by obtaining information about analytes such as glucose, as well as obtaining information about other physiological properties. Diabetes and other diseases may be treated by delivering an infusate, such as insulin and other agents.

Obtaining information about analytes and/or other physiological properties may be performed using one or more sensors implanted in a subject. For example, obtaining information about glucose concentration may be performed using a glucose sensor implanted in a subject. Sensors may kink, fold, and break during insertion and wear. Also, sensors implanted for prolonged periods of time may lead to a stagnant sensor-tissue interface.

Delivering an infusate may be performed using a catheter implanted in a subject. An implantation site for a catheter may be separate from an implantation site for a sensor. Multiple implantation sites for a catheter and a sensor may use more space and may cause more trauma.

What is needed are in vivo sensing devices with sensors that resist kinking, folding, and breaking. What is also needed are in vivo sensing devices that reduce the likelihood of a stagnant sensor-tissue interface. What is also needed are sensing and infusion devices that are able to both (1) sense an analyte and/or physiological property and (2) deliver an infusate, with fewer implantation sites, such as a single implantation site.

SUMMARY

Sensing and infusion devices are described. In one embodiment, a sensing and infusion device may include an implantable segment having a sensor. The sensing and infusion device may also include a catheter, and a sensor channel may be formed in the catheter. The sensor channel may be configured to retain at least a portion of the implantable segment.

In vivo sensing devices are described. In one embodiment, an in vivo sensing device may include an implantable body having a sensor. The implantable body may be configured to be implanted in an implantation site. The implantable body may have a first implantable segment and a second implantable segment. A distal portion of the first implantable segment may be coupled to a distal portion of the second implantable segment. The first implantable segment may be coupled to the second implantable segment along at least part of a length of the first implantable segment. The in vivo sensing device may also include a first spacer arm. An inner portion of the first spacer arm may be coupled to a proximal portion of the first implantable segment. The in vivo sensing device may also include a second spacer arm. An inner portion of the second spacer arm may be coupled to a proximal portion of the second implantable segment. The in vivo sensing device may also include a first contact tab coupled to an outer portion of the first spacer arm, and second contact tab coupled to an outer portion of the second spacer arm.

BRIEF DESCRIPTION OF THE DRAWINGS

FIGS. 18A-18B show one embodiment of a method for implanting in vivo sensing device 3000.

DESCRIPTION

FIGS. 1A-1E show one embodiment of a sensing and infusion device 1000.

Figure 1A:
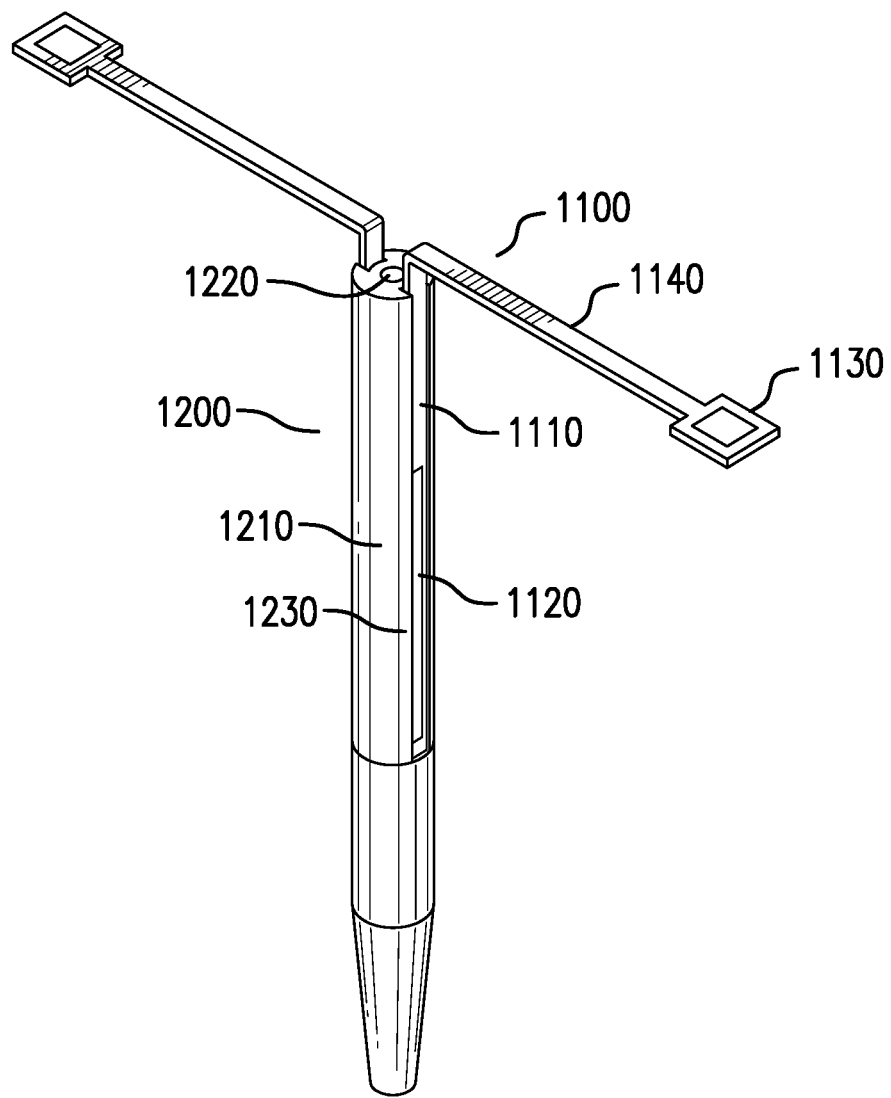
FIGS. 1A-1E show one embodiment of an in vivo sensing device 1000.
Figure 1B:
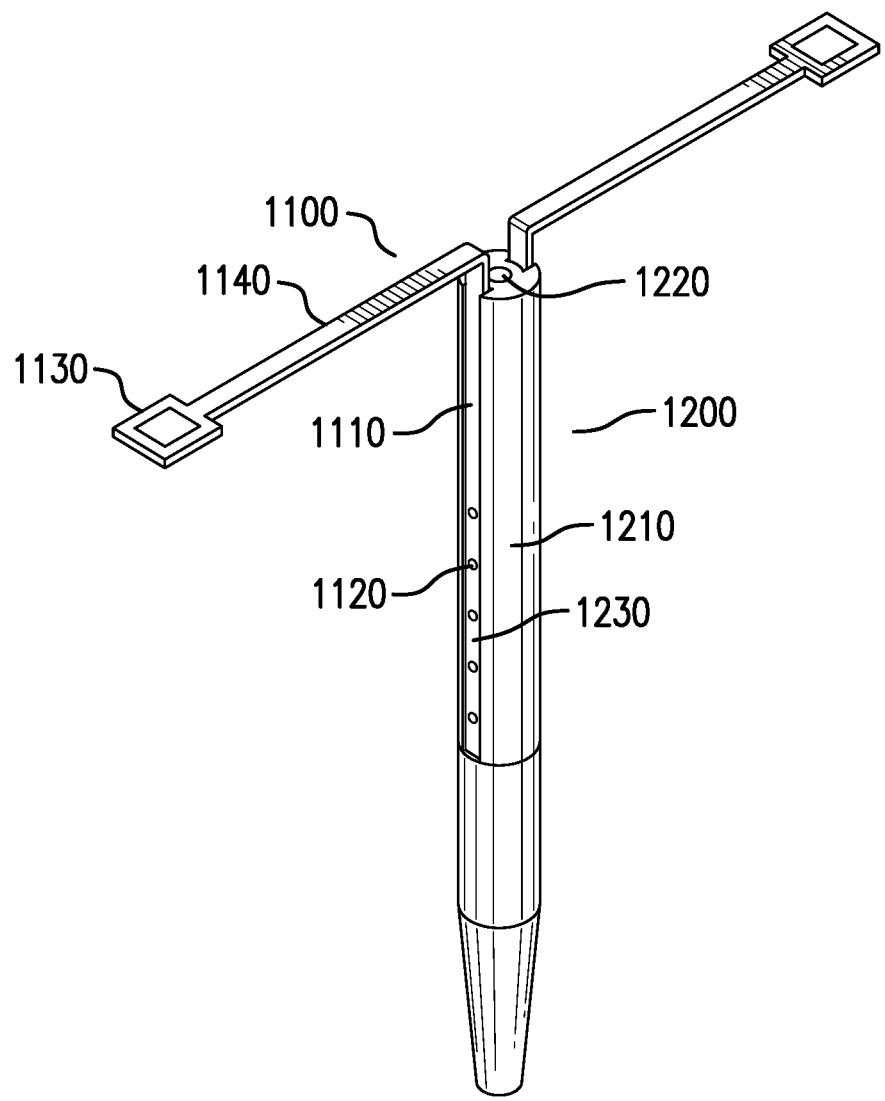
Figure 1C:
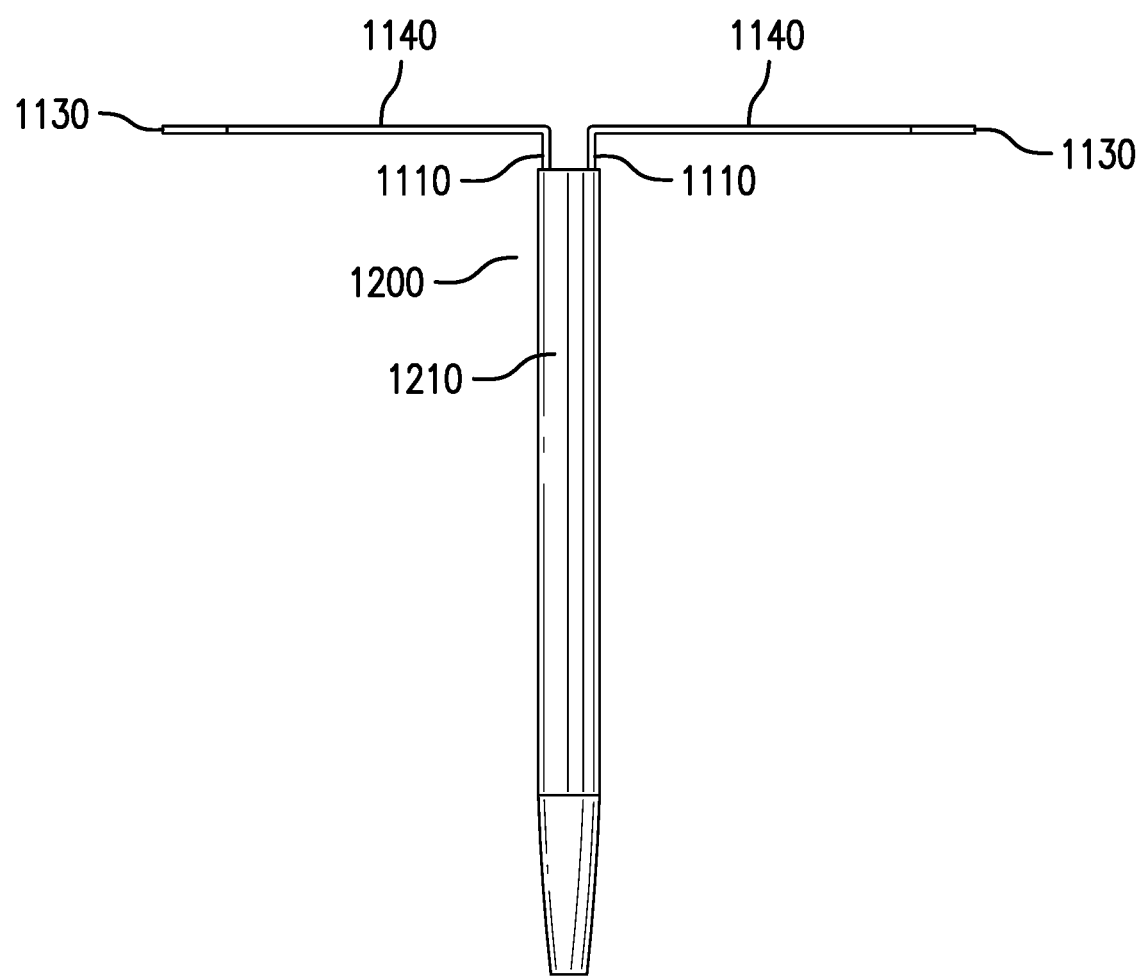
Figure 1D:
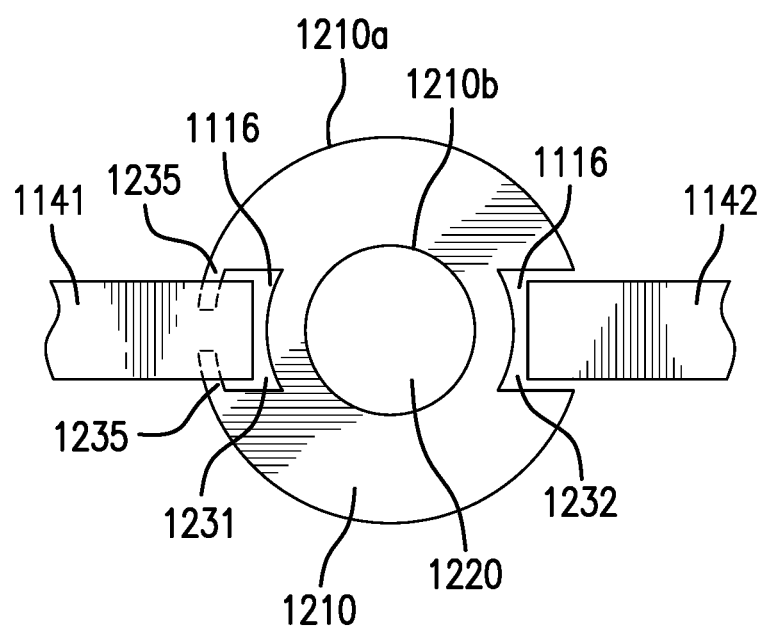
Figure 1E:
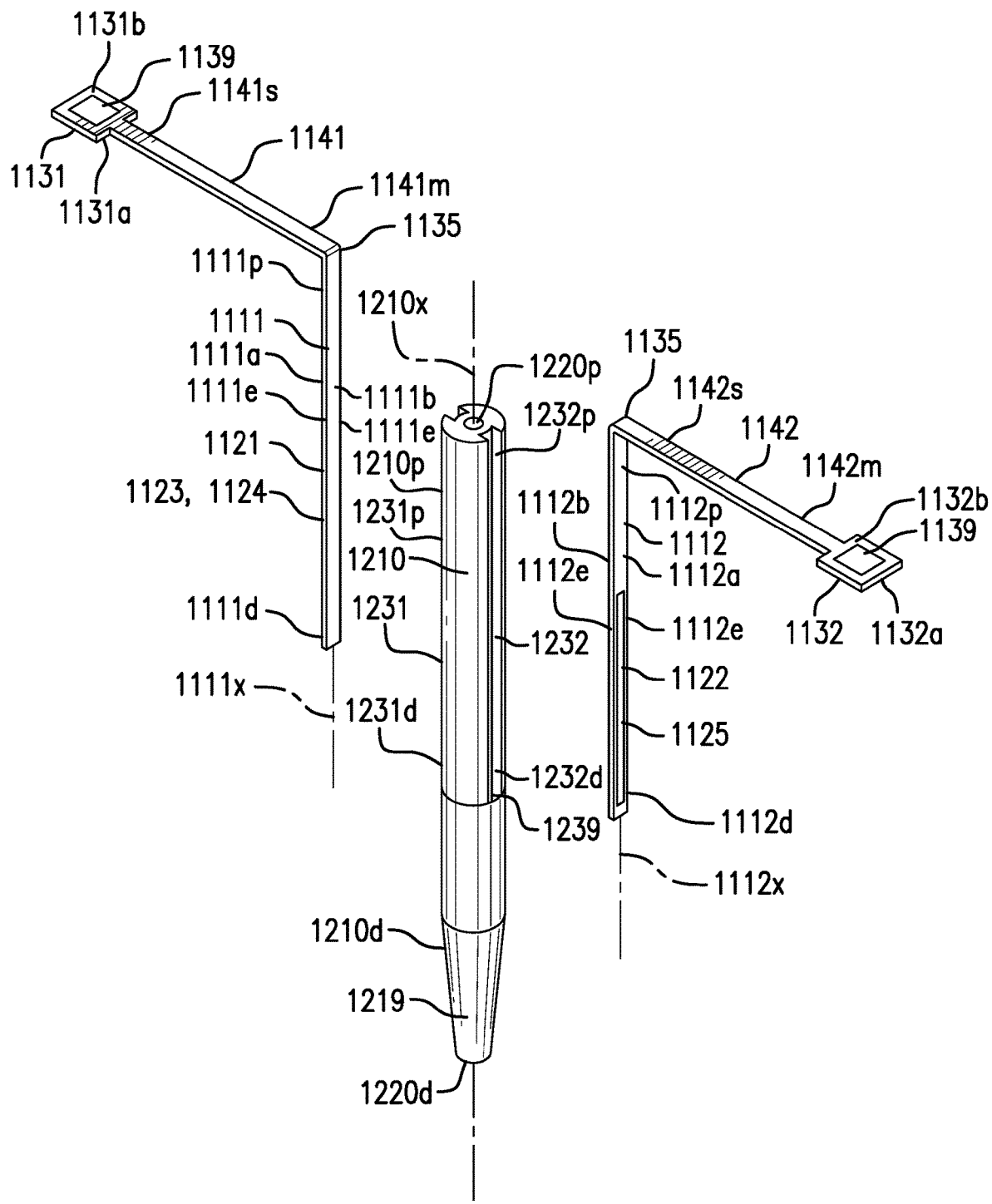

FIGS. 1A-1B show perspective views of sensing and infusion device 1000. FIG. 1C shows a side view of sensing and infusion device 1000. FIG. 1D shows a top view of sensing and infusion device 1000. FIG. 1E shows an exploded view of sensing and infusion device 1000.

Sensing and infusion device 1000 is capable of providing information about an analyte and/or other measurements in vivo. Sensing and infusion device 1000 may also be capable of delivering an infusate.

Sensing and infusion device 1000 includes a sensor assembly 1100 and a catheter assembly 1200.

Sensor assembly 1100 includes one or more implantable segments 1110. Implantable segments 1110 may be configured to be at least partially implanted in an implantation site in a subject. The implantation site may be in a tissue of a body of a subject.

Implantable segments 1110 may include a first implantable segment 1111. Implantable segments 1110 may include a second implantable segment 1112.

First implantable segment 1111 may include a proximal portion 1111*p*, a distal portion 1111*d*, a longitudinal axis 1111*x*, an outer side 1111*a*, an inner side 1111*b*, and edges 1111*e*. First implantable segment 1111 may be elongate. First implantable segment 1111 may be flat. First implantable segment 1111 may be flexible. First implantable segment 1111 may be straight or curved. First implantable segment 1111 may include one or more bends.

Second implantable segment 1112 may include a proximal portion 1112*p*, a distal portion 1112*d*, a longitudinal axis 1112*x*, an outer side 1112*a*, and an inner side 1112*b*. Second implantable segment 1112 may be elongate. Second implantable segment 1112 may be flat. Second implantable segment 1112 may be flexible. Second implantable segment 1112 may be straight or curved. Second implantable segment 1112 may include one or more bends.

First implantable segment 1111 and second implantable segment 1112 may include one or more conducting layers. The conducting layers may include stainless steel and/or other conducting material. First implantable segment 1111 and second implantable segment 1112 may include one or more insulating layers. The insulating layers may include polyimide and/or other insulating material.

Figure 1F:
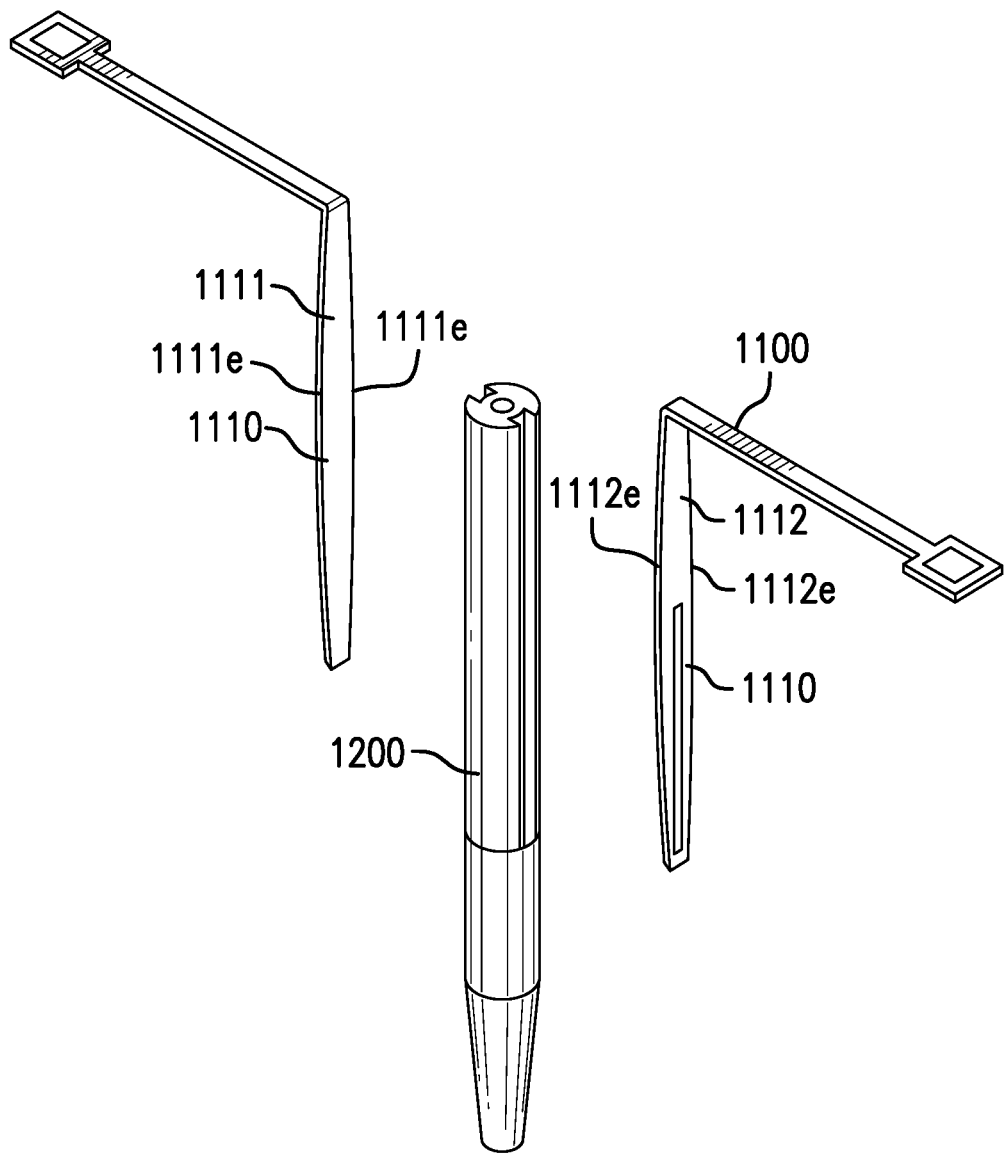
FIG. 1F shows in vivo sensing device 1000 with another embodiment of implantable segments 1110.

First implantable segment 1111 and second implantable segment 1112 may be of the same or different lengths and/or shapes. One or more of edges 1111*e* and edges 1112*e* may be straight, as shown in FIG. 1E, or curved, as shown in FIG. 1F.

Implantable segments 1110 may have spring-like properties. First implantable segment 1111 and second implantable segment 1112 may be capable of being deformed, and then spring back to their original shapes. First implantable segment 1111 and second implantable segment 1112 may be configured to bow out or flex if they are compressed in a longitudinal direction. This bowing out or flexing may reduce the likelihood that first implantable segment 1111 and second implantable segment 1112 will break, kink, coil, or come out while implanted. This bowing out or flexing may help to refresh interstitial fluid and/or displace any blood surrounding implantable segments 1110. First implantable segment 1111 and second implantable segment 1112 may have sufficient fatigue strength to last a design life of sensor assembly 1100.

Sensor assembly 1100 includes at least one sensor 1120. Sensor 1120 may include one or more components that are an integral part of implantable segments 1110. These components may be at least partially formed as part of one or more sides and/or edges of implantable segments 1110. Sensor 1120 may include one or more discrete components that are coupled to implantable segments 1110.

Sensor 1120 may include one or more portions. Sensor 1120 may include a first portion 1121 that is part of and/or coupled to first implantable segment 1111. First portion 1121 may be part of and/or coupled to outer side 1111*b* and/or inner side 1111*a* of first implantable segment 1111. Sensor 1120 may include a second portion 1122 that is part of and/or coupled to second implantable segment 1112. Second portion 1122 may be part of and/or coupled to outer side 1112*b* and/or inner side 1112*a* of second implantable segment 1112.

Figure 1G:
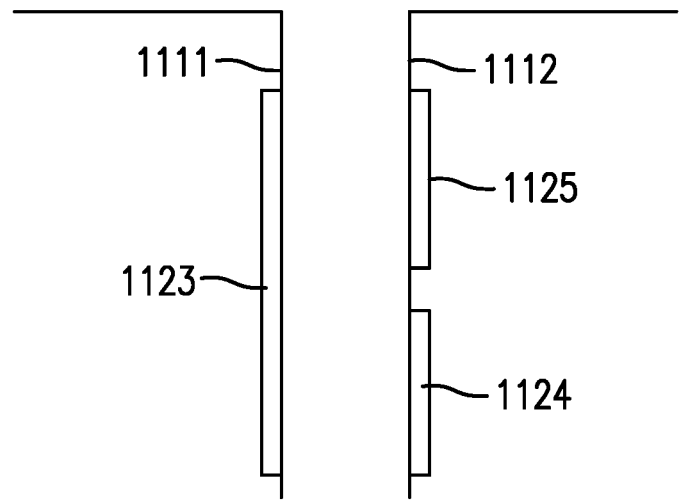
FIGS. 1G-1H show in vivo sensing device 1000 with at least one sensor 1120.
Figure 1H:
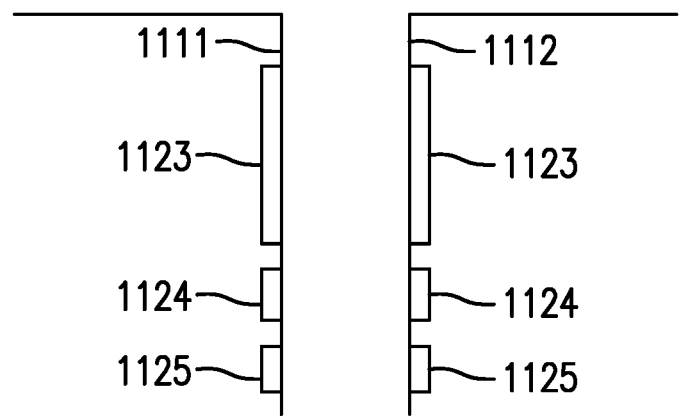

Sensor 1120 may include one or more electrodes. Sensor 1120 may include a working electrode 1123. Sensor 1120 may include a counter electrode 1124 and/or a reference electrode 1125. Sensor 1120 may include a combined counter/reference electrode. First portion 1121 and second portion 1122 may each include any one any combination of these electrodes. In one example, first portion 1121 of sensor 1120 may include working electrode 1123, and be part of and/or coupled to first implantable segment 1111, while second portion 1122 of sensor 1120 may include counter electrode 1124 and reference electrode 1125, and be part of and/or coupled to second implantable segment 1112, as shown in FIG. 1G. In another example, first portion 1121 of sensor 1120 may include a first set of working electrode 1123, counter electrode 1124, and reference electrode 1125, and be part of and/or coupled to first implantable segment 1111, while second portion 1122 of sensor 1120 may include a second set of working electrode 1123, counter electrode 1124, and reference electrode 1125, and be part of and/or coupled to second implantable segment 1112, as shown in FIG. 1H.

Sensor 1120 may be configured to provide information about a tissue in which sensor 1120 is implanted. Sensor 1120 may be configured to provide information about an analyte and/or other measurements. Sensor 1120 may be configured to provide information about any one or any combination of temperature, pressure, pH, hydration, and perfusion. Sensor 1120 may be configured to provide information about impedance and/or other electrical properties. Sensor 1120 may include any one or any combination of a glucose sensor, oxygen sensor, lactate sensor, or other sensor. Multiple sensors 1120 having different functions may be included. Multiple sensors 1120 having the same function, of the same or different types, may be included for redundancy.

Sensor 1120 may be configured to be in direct contact with a tissue in a body of a subject. Sensor 1120 may be open to an exterior of implantable segments 1110.

Sensor assembly 1100 may include one or more contact tabs 1130. Contact tabs 1130 may be coupled to implantable segments 1110. Contact tabs 1130 may be configured to rest outside of the implantation site.

Contact tabs 1130 may provide electrical connections to sensor 1120. Contact tabs 1130 may allow a computer and/or circuit to be electrically coupled to sensor 1120. Contact tabs 1130 may allow a power source to be electrically coupled to sensor 1120.

Contact tabs 1130 may include at least one tab. Contact tabs 1130 may include a first contact tab 1131. Contact tabs 1130 may include a second contact tab 1132. First contact tab 1131 may have a first side 1131*a* and a second side 1131*b*. Second contact tab 1132 may have a first side 1132*a* and a second side 1132*b*.

First contact tab 1131 may be coupled to first implantable segment 1111. First contact tab 1131 may be coupled to proximal portion 1111*p* of first implantable segment 1111. First contact tab 1131 and proximal portion 1111*p* may be coupled by at least one bend 1135. First contact tab 1131 and first implantable segment 1111 may be formed as a single piece that is bent at bend 1135. Alternatively, first contact tab 1131 and first implantable segment 1111 may be formed as separate pieces, and first contact tab 1131 and proximal portion 1111p may be coupled by a hinge, joint, link, or other coupling. First contact tab 1131 and proximal portion 1111p may be substantially perpendicular. First contact tab 1131 and proximal portion 1111p may form an angle of approximately 30 to 150 degrees. First contact tab 1131 may be flat. First contact tab 1131 may be flexible.

Second contact tab 1132 may be coupled to second implantable segment 1112. Second contact tab 1132 may be coupled to proximal portion 1112p of second implantable segment 1112. Second contact tab 1132 and proximal portion 1112p may be coupled by at least one bend 1135. Second contact tab 1132 and second implantable segment 1112 may be formed as a single piece that is bent at bend 1135. Alternatively, second contact tab 1132 and second implantable segment 1112 may be formed as separate pieces, and second contact tab 1132 and proximal portion 1112p may be coupled by a hinge, joint, link, or other coupling. Second contact tab 1132 and proximal portion 1112p may be substantially perpendicular. Second contact tab 1132 and proximal portion 1112p may form an angle of approximately 30 to 150 degrees. Second contact tab 1132 may be flat. Second contact tab 1132 may be flexible.

First contact tab 1131 and/or second contact tab 1132 may include one or more conducting layers. Bends 1135 may include one or more conducting layers. The conducting layers may include stainless steel and/or other conducting material. First contact tab 1131 and/or second contact tab 1132 may include one or more insulating layers. Bends 1135 may include one or more insulating layers. The insulating layers may include polyimide and/or other insulating material. Some or all of the layers may remain intact or unbroken at bends 1135. Bends 1135 may be a bend, fold, crease, or any elastic or plastic deformation. Bends 1135 may be permanent or temporary.

First contact tab 1131 may be coupled to first portion 1121 of sensor 1120. Second contact tab 1132 may be coupled to second portion 1122 of sensor 1120.

First contact tab 1131 may include one or more contact pads 1139. Contact pads 1139 may be formed on first side 1131a and/or second side 1131b. Second contact tab 1132 may include one or more contact pads 1139. Contact pads 1139 may be formed on first side 1132a and/or second side 1132b. Contact pads 1139 may be formed by removing a portion of an insulating layer to expose a conducting layer.

Contact pads 1139 may be electrically coupled to one or more portions of sensor 1120. Contact pads 1139 may be coupled to sensor 1120 by one or more leads.

First contact tab 1131 and second contact tab 1132 may be oriented in different directions. First contact tab 1131 and second contact tab 1132 may be oriented in opposite directions. This orientation may balance sensor assembly 1100 and reduce the likelihood of damage or coming out of the implantation site. This orientation may allow first contact tab 1131 and second contact tab 1132 to be spaced apart. This spacing apart may provide room to make electrical connections to first contact tab 1131 and second contact tab 1132, such as to an on-body worn device (OBWD). This spacing apart may provide room to make bulky hermetic or airtight seals for electrical connections to first contact tab 1131 and/or second contact tab 1132. In one example, first contact tab 1131 and second contact tab 1132 may be separated by 3 mm or more.

First contact tab 1131 and second contact tab 1132 may be capable of lying flat against and/or parallel to an outside surface of the implantation site. This may allow a portion of sensing and infusion device 1000 outside of the implantation site to have a reduced height and/or size.

Sensor assembly 1100 may include one or more spacer arms 1140. Spacer arms 1140 may be coupled to implantable segments 1110 and contact tabs 1130. Spacer arms 1140 may be coupled between implantable segments 1110 and contact tabs 1130.

Spacer arms 1140 may include a first spacer arm 1141. First spacer arm 1141 may include a medial portion 1141m and a side portion 1141s. Spacer arms 1140 may include a second spacer arm 1142. Second spacer arm 1142 may include a medial portion 1142m and a side portion 1142s.

Figure 1I:
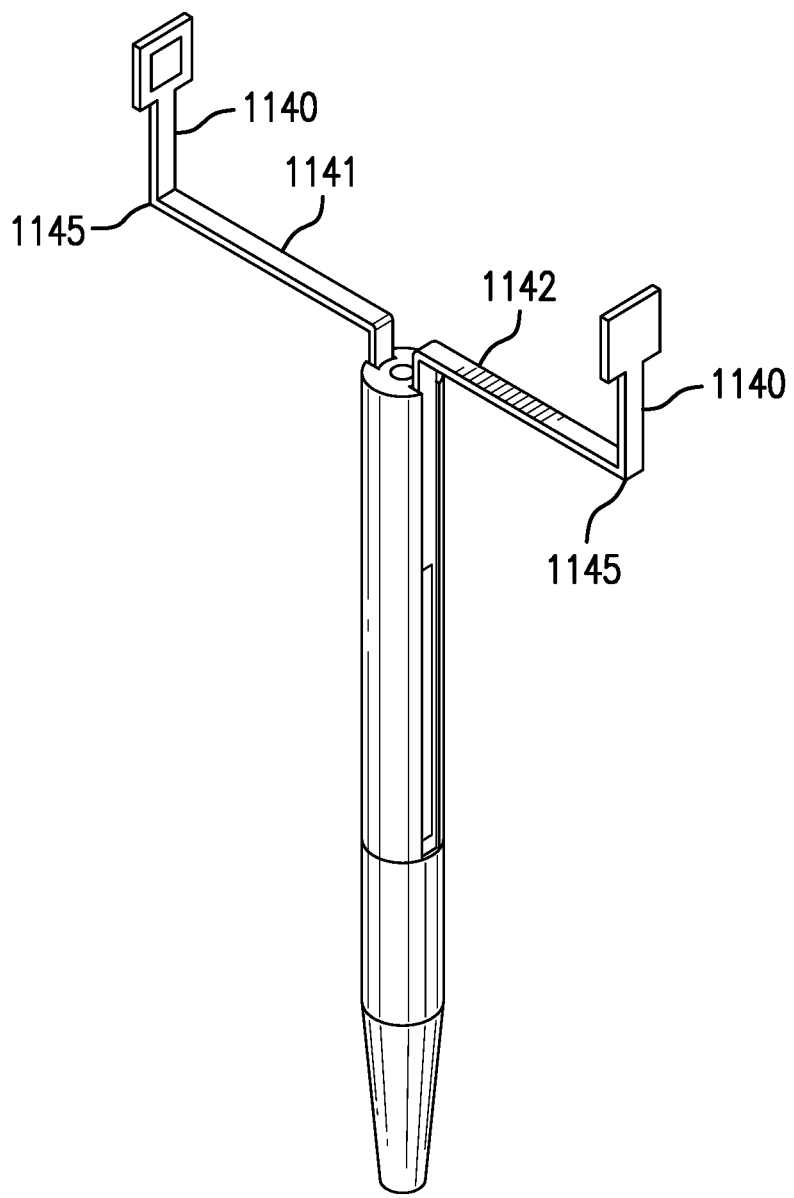
FIG. 1I shows in vivo sensing device 1000 with another embodiment of spacer arms 1140.

First spacer arm 1141 may be coupled to first implantable segment 1111 and first contact tab 1131. Medial portion 1141m of first spacer arm 1141 may be coupled to proximal portion 1111p of first implantable segment 1111. Side portion 1141s of first spacer arm 1141 may be coupled to first contact tab 1131. Medial portion 1141m and proximal portion 1111p may be coupled by at least one bend 1135. First spacer arm 1141 and first implantable segment 1111 may be formed as a single piece that is bent at bend 1135. Alternatively, first spacer arm 1141 and first implantable segment 1111 may be formed as separate pieces, and medial portion 1141m and proximal portion 1111p may be coupled by a hinge, joint, link, or other coupling. Medial portion 1141m and proximal portion 1111p may be substantially perpendicular. Medial portion 1141m and proximal portion 1111p may form an angle of approximately 30 to 150 degrees. First spacer arm 1141 may be elongate. First spacer arm 1141 may be flat. First spacer arm 1141 may be flexible. First spacer arm 1141 may be straight or curved. First spacer arm 1141 may include one or more bends 1145, as shown in FIG. 1I.

Second spacer arm 1142 may be coupled to second implantable segment 1112 and second contact tab 1132. Medial portion 1142m of second spacer arm 1142 may be coupled to proximal portion 1112p of second implantable segment 1112. Side portion 1142s of second spacer arm 1142 may be coupled to second contact tab 1132. Medial portion 1142m and proximal portion 1112p may be coupled by at least one bend 1135. Second spacer arm 1142 and second implantable segment 1112 may be formed as a single piece that is bent at bend 1135. Alternatively, second spacer arm 1142 and second implantable segment 1112 may be formed as separate pieces, and medial portion 1142m and proximal portion 1112p may be coupled by a hinge, joint, link, or other coupling. Medial portion 1142m and proximal portion 1112p may be substantially perpendicular. Medial portion 1142m and proximal portion 1112p may form an angle of approximately 30 to 150 degrees. Second spacer arm 1142 may be elongate. Second spacer arm 1142 may be flat. Second spacer arm 1142 may be flexible. Second spacer arm 1142 may be straight or curved. Second spacer arm 1142 may include one or more bends 1145.

First spacer arm 1141 and/or second spacer arm 1142 may include one or more conducting layers. Bends 1145 may include one or more conducting layers. The conducting layers may include stainless steel and/or other conducting material. First spacer arm 1141 and/or second spacer arm 1142 may include one or more insulating layers. bends 1145 may include one or more insulating layers. The insulating layers may include polyimide and/or other insulating material.

First spacer arm 1141 and second spacer arm 1142 may be oriented in different directions. First spacer arm 1141 and second spacer arm 1142 may be oriented in opposite directions. First spacer arm 1141 and second spacer arm 1142 may be of the same or different lengths and/or shapes.

First spacer arm 1141 and second spacer arm 1142 may be capable of lying flat against and/or parallel to an outside surface of the implantation site. This may allow a portion of sensing and infusion device 1000 outside of the implantation site to have a reduced height and/or size.

First spacer arm 1141 and second spacer arm 1142 may allow first contact tab 1131 and second contact tab 1132 to be spaced apart. First spacer arm 1141 and second spacer arm 1142 may allow a distance and positioning between first contact tab 1131 and second contact tab 1132 to be adjusted. This distance and positioning may provide space to make electrical connections to first contact tab 1131 and second contact tab 1132, such as to an on-body worn device (OBWD). This distance and positioning may provide space to make bulky electrical connections to first contact tab 1131 and/or second contact tab 1132. For example, first contact tab 1131 and/or second contact tab 1132 may require a bulky hermetic or airtight seal when coupled to working electrode 1123.

First spacer arm 1141 and second spacer arm 1142 may have spring-like properties. First spacer arm 1141 and second spacer arm 1142 may be capable of being deformed, and then spring back to their original shapes. First spacer arm 1141 and second spacer arm 1142 may be configured to bias implantable segments 1110 back into the implantation site when implantable segments 1110 travel at least partially out of the implantation site. First spacer arm 1141 and second spacer arm 1142 may be configured to bias implantable segments 1110 in a distal direction when implantable segments 1110 travel in a proximal direction. This travel may help to refresh interstitial fluid and/or displace any blood surrounding implantable segments 1110. First implantable segment 1111 and second implantable segment 1112 may have sufficient stiffness to be pushed back into the implantation site instead of buckling or bunching in an accordion-like fashion outside of the implantation site. First spacer arm 1141 and second spacer arm 1142 may have sufficient fatigue strength to last a design life of sensor assembly 1100.

Catheter assembly 1200 includes at least one catheter 1210.

Catheter 1210 includes a proximal portion 1210p, a distal portion 1210d, and a longitudinal axis 1210x. Catheter 1210 includes an outer surface 1210a and an inner surface 1210b. Catheter 1210 may have a cross section that is circular. Alternatively, catheter 1210 may have a cross section that is oval, square, triangular, or other suitable shape. Catheter 1210 may be flexible.

Catheter 1210 may include an infusion lumen 1220 formed in catheter 1210. Infusion lumen 1220 may have a distal end 1220d that is open or closed. Catheter 1210 may include one or more infusion ports formed in catheter 1210. Infusion ports may be in fluid communication with infusion lumen 1220. Infusion ports may be formed in a side of catheter 1210.

Catheter 1210 may include a tip 1219 at distal portion 1210d of catheter 1210. Tip 1219 may be soft and tapered.

Catheter assembly 1200 may include one or more sensor channels 1230. Sensor channels 1230 may be formed in outer surface 1210a and/or inner surface 1210b of catheter 1210. Sensor channels 1230 may be evenly or unevenly spaced. Each sensor channel 1230 may be configured to be coupled to one or more implantable segments 1110.

Sensor channels 1230 may include a first sensor channel 1231. First sensor channel 1231 may be formed in outer surface 1210a of catheter 1210. First sensor channel 1231 may include a proximal portion 1231p and a distal portion 1231d. First sensor channel 1231 may be configured to receive at least a portion of first implantable segment 1111. First sensor channel 1231 may be configured to receive at least a portion of first implantable segment 1111. First sensor channel 1231 may retain at least a portion of first implantable segment 1111 with an interference fit and/or an adhesive. First sensor channel 1231 may have a cross section shaped to retain at least a portion of first implantable segment 1111. First sensor channel 1231 may have a cross section that narrows towards outer surface 1210a of catheter 1210. First sensor channel 1231 may include a lip 1235 configured to retain at least a portion of first implantable segment 1111, as shown in FIG. 1D, or no lip 1235. First sensor channel 1231 may include a slot 1239 at distal portion 1231d of first sensor channel 1231. Distal portion 1111d of first implantable segment 1111 may be at least partially positioned in slot 1239 of first sensor channel 1231.

First sensor channel 1231 may be open to an exterior of catheter 1210. First sensor channel 1231 may be open along an entire length of first sensor channel 1231. Alternatively, first sensor channel 1231 may be open along at least 50% or at least 90% of first sensor channel 1231. First sensor channel 1231 may extend from proximal portion 1210p to distal portion 1210d of catheter 1210. First sensor channel 1231 may extend along an entire length of catheter 1210. Alternatively, first sensor channel 1231 may extend along at least 75% or at least 90% of an entire length of catheter 1210. First sensor channel 1231 may be parallel to longitudinal axis 1210x of catheter 1210. First sensor channel 1231 may spiral around longitudinal axis 1210x of catheter 1210.

Sensor channels 1230 may include a second sensor channel 1232. Second sensor channel 1232 may be formed in outer surface 1210a of catheter 1210. Second sensor channel 1232 may include a proximal portion 1232p and a distal portion 1232d. Second sensor channel 1232 may be configured to receive at least a portion of second implantable segment 1112. Second sensor channel 1232 may be configured to retain at least a portion of second implantable segment 1112. Second sensor channel 1232 may retain at least a portion of second implantable segment 1112 with an interference fit and/or an adhesive. Second sensor channel 1232 may have a cross section shaped to retain at least a portion of second implantable segment 1112. Second sensor channel 1232 may have a cross section that narrows towards outer surface 1210a of catheter 1210. Second sensor channel 1232 may include a lip 1235 configured to retain at least a portion of second implantable segment 1112, or no lip 1235 as shown in FIG. 1D. Second sensor channel 1232 may include a slot 1239 at distal portion 1232d of second sensor channel 1232. Distal portion 1112d of second implantable segment 1112 may be at least partially positioned in slot 1239 of second sensor channel 1232.

Second sensor channel 1232 may be open to an exterior of catheter 1210. Second sensor channel 1232 may be open along an entire length of second sensor channel 1232. Alternatively, second sensor channel 1232 may be open along at least 50% or at least 90% of second sensor channel 1232. Second sensor channel 1232 may extend from proximal portion 1210p to distal portion 1210d of catheter 1210. Second sensor channel 1232 may extend along an entire length of catheter 1210. Alternatively, second sensor channel 1232 may extend along at least 75% or at least 90% of an entire length of catheter 1210. Second sensor channel 1232 may be parallel to longitudinal axis 1210x of catheter 1210. Second sensor channel 1232 may spiral around longitudinal axis 1210x of catheter 1210.

Sensor channels 1230 with an open structure expose a greater portion of implantable segments 1110, which allows for a larger sensing area. This larger sensing area may be used for larger sensors 1120, which may provide greater sensitivity and/or accuracy. This larger sensing area may allow more sensors 1120 to be used, such as for multiple analytes and/or redundancy.

First sensor channel 1231 and second sensor channel 1232 may be of the same or different lengths and/or shapes. First sensor channel 1231 and second sensor channel 1232 may be spaced uniformly or non-uniformly about a circumference of catheter 1210. For example, first sensor channel 1231 and second sensor channel 1232 may be spaced 180 degrees from each other, or 90 degrees from each other.

Sensor channels 1230 may be configured to provide a space 1116 between implantable segments 1110 and catheter 1210. Space 1116 may allow inner side 1111b of first implantable segment 1111 and/or inner side 1112b of second implantable segment 1112 to be used for sensing. Space 1116 may also allow for a larger sensing area by allowing more than one side of implantable segments 1110 to be used.

Figure 2A:
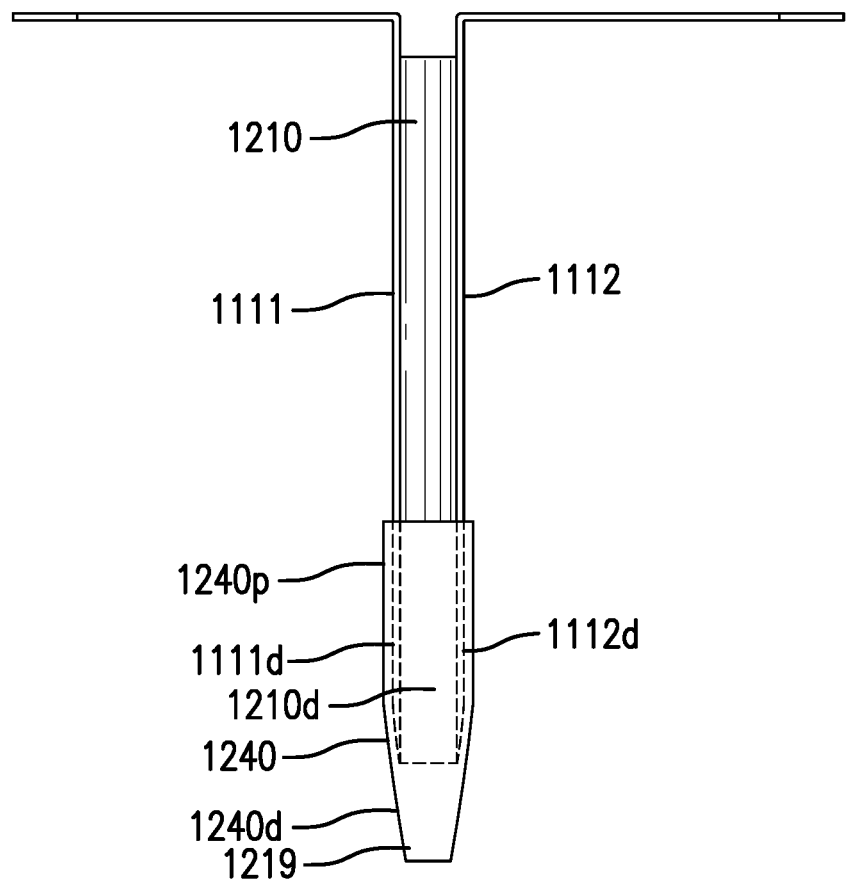
FIGS. 2A-2B show in vivo sensing device 1000 with another embodiment of catheter assembly 1200.
Figure 2B:
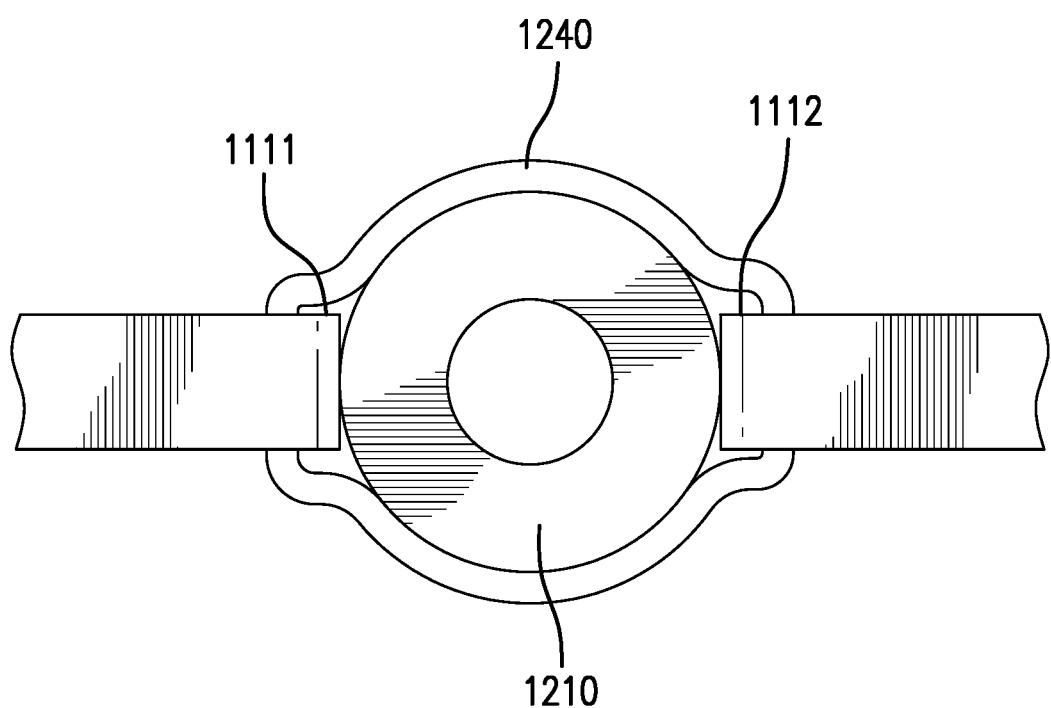

FIGS. 2A-2B show sensing and infusion device 1000 with another embodiment of catheter assembly 1200. FIG. 2A shows a side view of sensing and infusion device 1000. FIG. 2B shows a top view of sensing and infusion device 1000.

Catheter assembly 1200 may include a collar 1240. Collar 1240 is configured to couple first implantable segment 1111 and second implantable segment 1112 to catheter 1210. Collar 1240 may be used with or without a sensor channel 1230.

Collar 1240 includes a proximal portion 1240p and a distal portion 1240d. Collar 1240 may be placed around first implantable segment 1111, second implantable segment 1112, and catheter 1210 to couple first implantable segment 1111 and second implantable segment 1112 to catheter 1210. Collar 1240 may be placed around a distal portion 1111d and distal portion 1112d without covering any part of sensor 1120. Collar 1240 may be placed around a distal portion 1210d of catheter 1210. Collar 1240 may couple first implantable segment 1111 and second implantable segment 1112 along sides of catheter 1210.

Collar 1240 may be formed as a single piece with tip 1219. Alternatively, collar 1240 may be separate from tip 1219. Collar 1240 may be made of a flexible material.

Figure 3A:
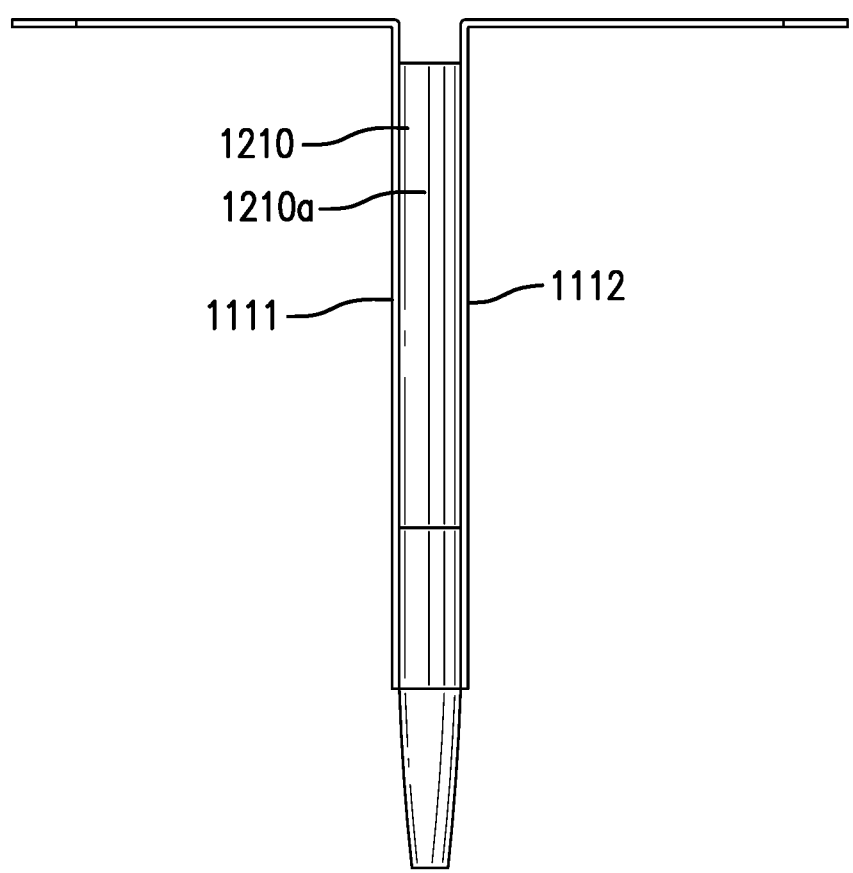
FIGS. 3A-3B show in vivo sensing device 1000 with another embodiment of catheter assembly 1200.
Figure 3B:
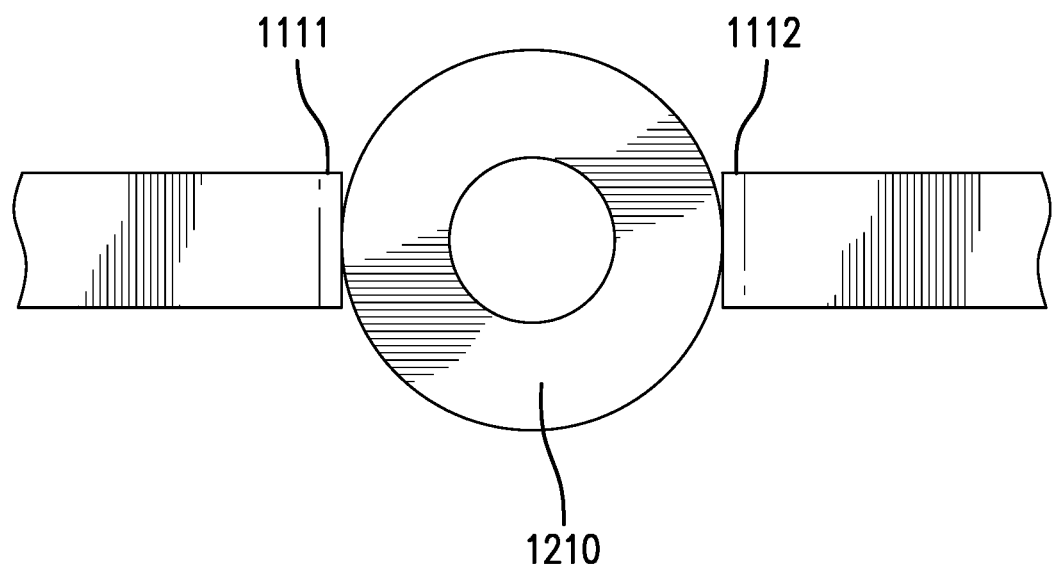

FIGS. 3A-3B show sensing and infusion device 1000 with another embodiment of catheter assembly 1200. FIG. 3A shows a side view of sensing and infusion device 1000. FIG. 3B shows a top view of sensing and infusion device 1000.

Catheter assembly 1200 does not include sensor channels 1230. First implantable segment 1111 and second implantable segment 1112 may be coupled to outer surface 1210a of catheter 1210. First implantable segment 1111 and second implantable segment 1112 may be coupled to catheter 1210 using an adhesive or any other suitable method. Alternatively, first implantable segment 1111 and second implantable segment 1112 may be positioned along sides of catheter 1210 without being coupled to catheter 1210.

Figure 4A:
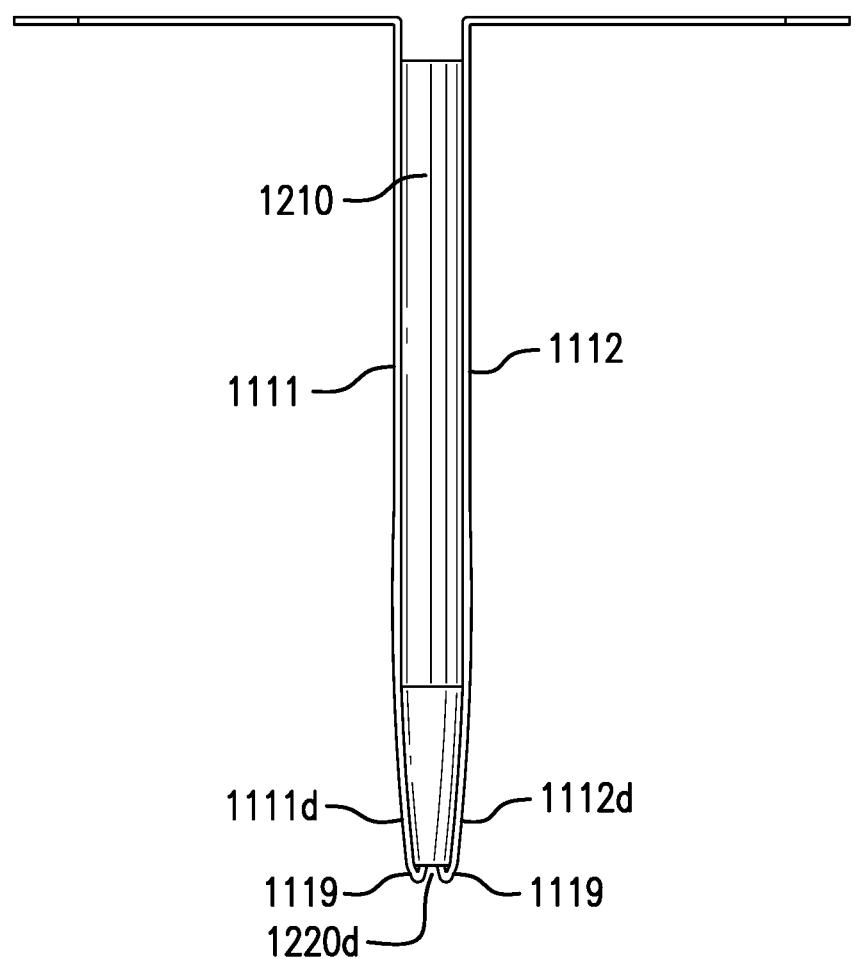
FIGS. 4A-4D show in vivo sensing device 1000 with various embodiments of implantable segments 1110.

FIG. 4A shows a side view of sensing and infusion device 1000 with another embodiment of implantable segments 1110.

Distal portion 1111d of first implantable segment 1111 may include a hook 1119. Hook 1119 may be formed as part of first implantable segment 1111. Hook 1119 may be a bent portion of first implantable segment 1111. Alternatively, hook 1119 may be separate from first implantable segment 1111 and coupled to distal portion 1111d. Hook 1119 of first implantable segment 1111 may be hooked into distal end 1220d of infusion lumen 1220.

Distal portion 1112d of second implantable segment 1112 may include a hook 1119. Hook 1119 may be formed as part of second implantable segment 1112. Hook 1119 may be a bent portion of second implantable segment 1112. Alternatively, hook 1119 may be separate from second implantable segment 1112 and coupled to distal portion 1112d. Hook 1119 of second implantable segment 1112 may be hooked into distal end 1220d of infusion lumen 1220.

Figure 4B:
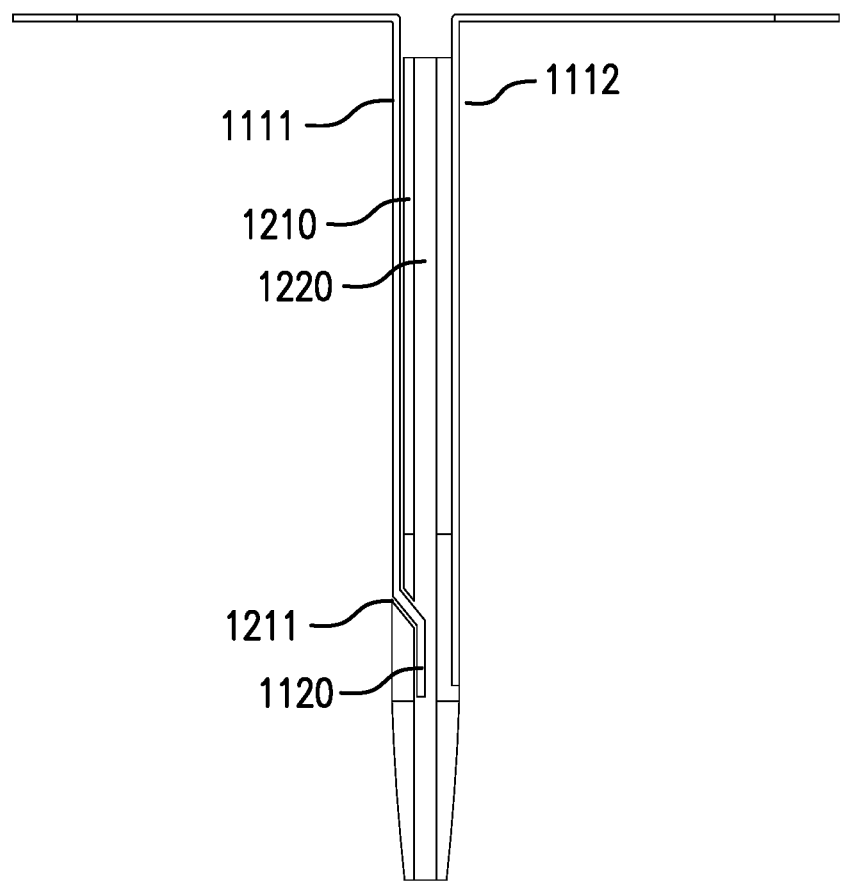

FIG. 4B shows a side cross-sectional view of sensing and infusion device 1000 with another embodiment of implantable segments 1110.

First implantable segment 1111 may have one or more portions positioned within infusion lumen 1220 of catheter 1210. First implantable segment 1111 may pass one through at least one opening 1211 formed in a wall of catheter 1210. First implantable segment 1111 may have a sensor 1120 positioned within infusion lumen 1220. Sensor 1120 may provide information about an infusate within infusion lumen 1220, such as pressure.

Figure 4C:
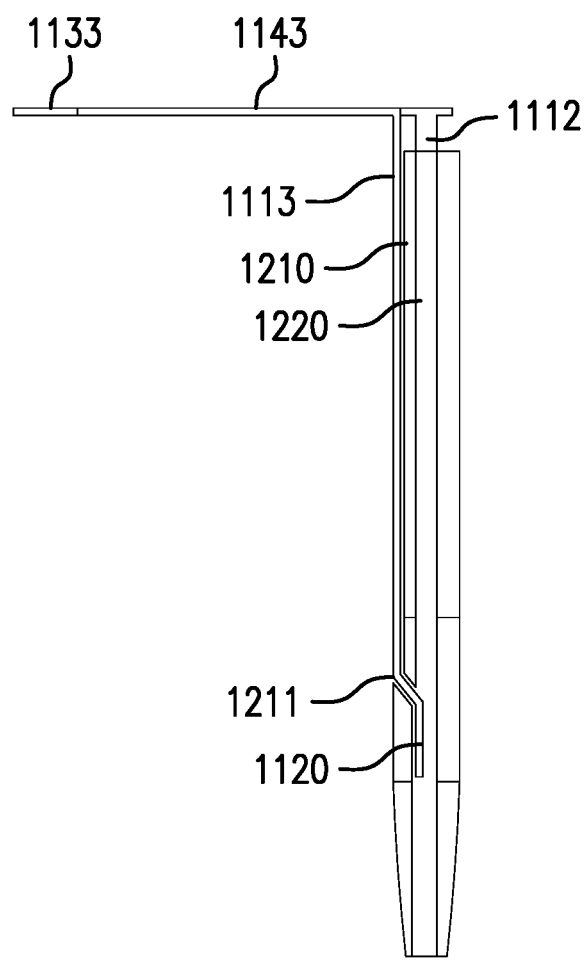
Figure 4D:
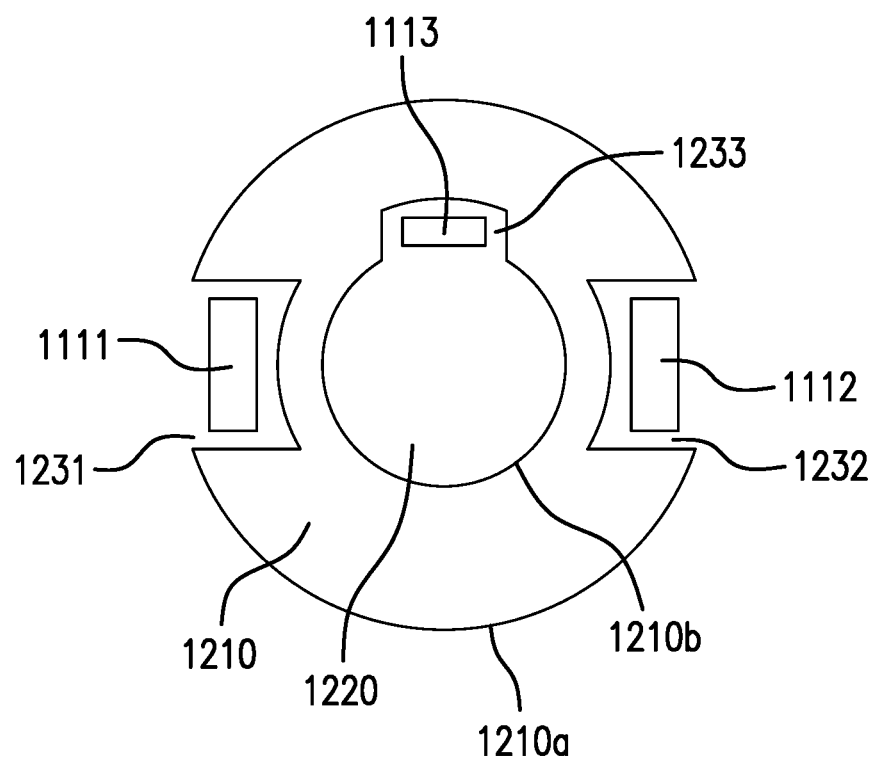

FIGS. 4C-4D show sensing and infusion device 1000 with another embodiment of implantable segments 1110. FIG. 4C shows a side cross-sectional view of sensing and infusion device 1000. FIG. 4D shows a top cross-sectional view of sensing and infusion device 1000.

Implantable segments 1110 may include a third implantable segment 1113. Third implantable segment 1113 may have one or more portions positioned within infusion lumen 1220 of catheter 1210. Third implantable segment 1113 may have one or more portions positioned against inner surface 1210b of catheter 1210, such as shown in FIG. 4C. Third implantable segment 1113 may have one or more portions positioned within a third sensor channel 1233 formed in inner surface 1210b of catheter 1210, as shown in FIG. 4D. Third implantable segment 1113 may pass through at least one opening 1211 formed in a wall of catheter 1210. Third implantable segment 1113 may have a sensor 1120 positioned within infusion lumen 1220. Sensor 1120 may provide information about an infusate within infusion lumen 1220, such as pressure. Contact tabs 1130 may include a third contact tab 1133 coupled to third implantable segment 1113. Spacer arms 1140 may include a third spacer arm 1143 coupled to third implantable segment 1133 and third contact tab 1133.

FIGS. 5A-5E show sensing and infusion device 1000 with various embodiments of a backflow device 1250.

Catheter assembly 1200 may include a backflow device 1250. Backflow device 1250 may be positioned proximal to infusion ports and/or distal end 1220d of infusion lumen 1220. Backflow device 1250 may be positioned proximal and/or distal to sensor 1120. Backflow device 1250 may be configured to reduce and/or compensate for backflow of an infusate from infusion lumen 1220 and/or infusion ports proximally towards one or more parts of sensor 1120. Backflow device 1250 may reduce data anomalies resulting from an infusate interacting with sensor 1120. For example, insulin as an infusate may be broken down at sensor 1120 and interfere with the accuracy of sensor 1120. Backflow device 1250 may increase the accuracy, life, and reliability of sensor 1120. Backflow device 1250 may increase sensing accuracy or reduce interference/noise in a therapeutic application.

Figure 5A:
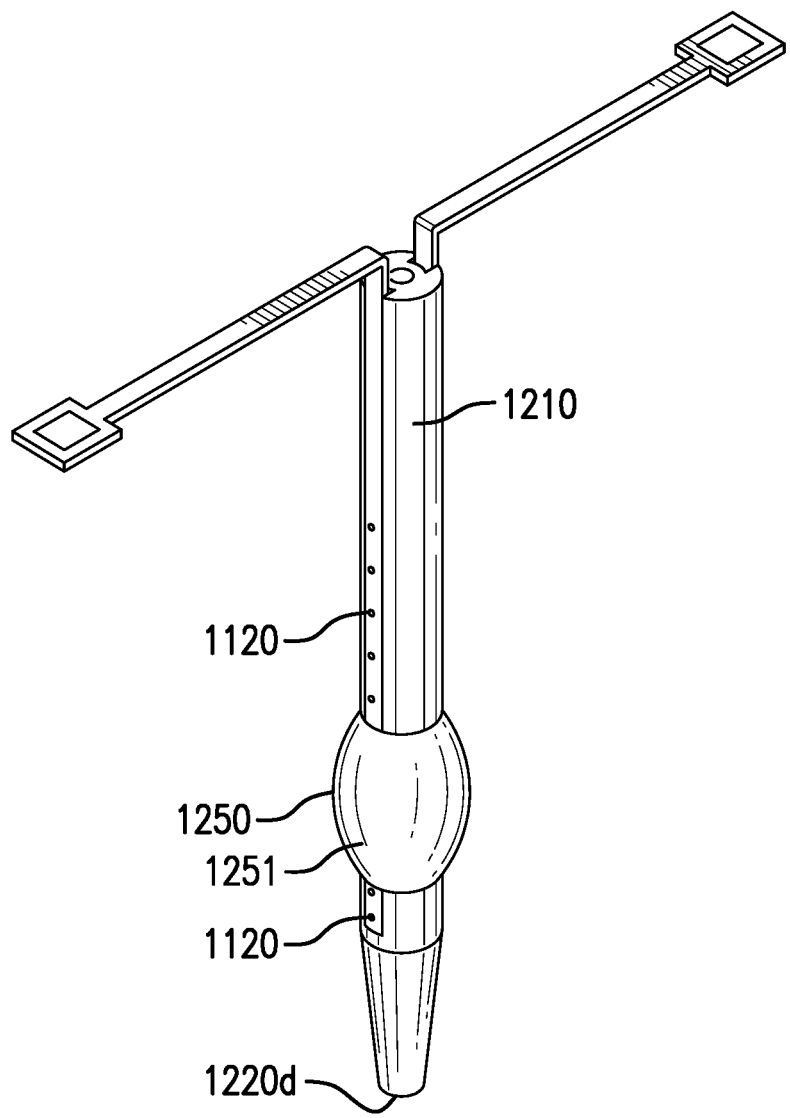
FIGS. 5A-5E show in vivo sensing device 1000 with various embodiments of a backflow device 1250.

FIG. 5A shows one embodiment of backflow device 1250. Backflow device 1250 may include a widened portion 1251 of catheter 1210. Widened portion 1251 may act as a physical barrier to at least partially block or direct an infusate away from parts of sensor 1120 proximal to widened portion 1251. Widened portion 1251 may be positioned proximal to one sensor 1120, such as a pressure sensor, and distal to another sensor 1120, such as a glucose sensor.

Figure 5B:
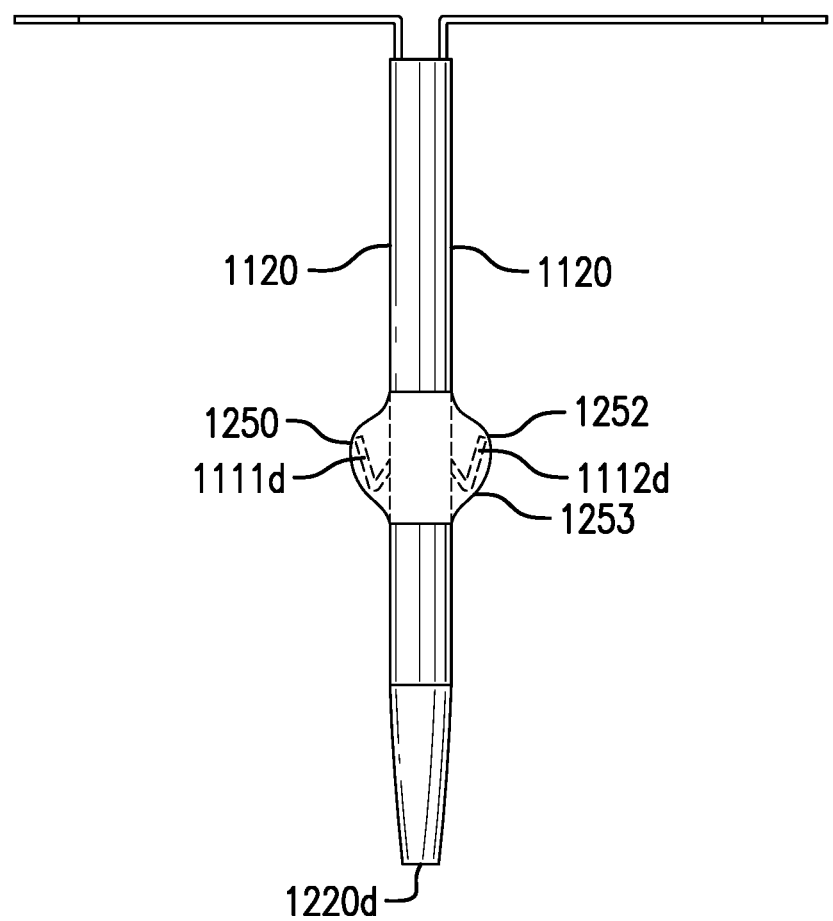

FIG. 5B shows another embodiment of backflow device 1250. Backflow device 1250 may include a deflector 1252. Deflector 1252 may include distal portion 1111*d* and/or distal portion 1112*d* protruding from sensor channel 1231 and/or sensor channel 1232. Deflector 1252 may include distal portion 1111*d* and/or distal portion 1112*d* that have been bent outwards between 0 and 180 degrees. Alternatively, deflector 1252 may be a separate element coupled to first implantable segment 1111 and/or second implantable segment 1112. Deflector 1252 may include a collet 1253 covering distal portion 1111*d* and distal portion 1112*d*. Collet 1253 may prevent distal portion 1111*d* and distal portion 1112*d* from catching when removed from a body of subject. Collet 1253 may be made of a flexible material such as silicone.

Figure 5C:
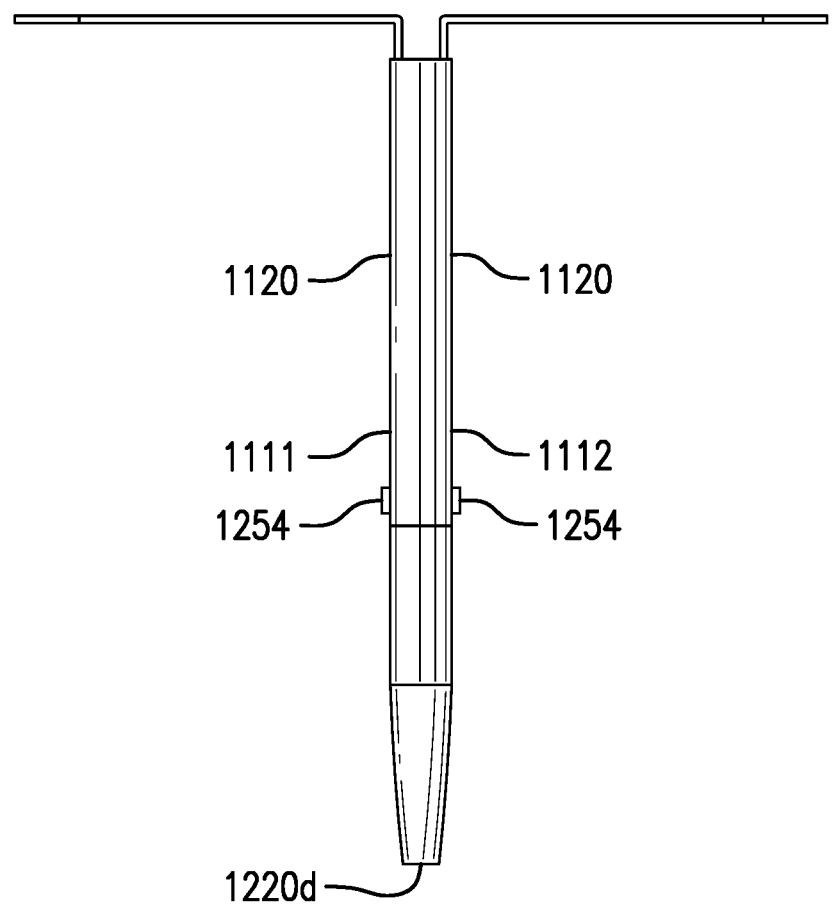

FIG. 5C shows another embodiment of backflow device 1250. Backflow device 1250 may include at least one infusate sink 1254. Infusate sink 1254 may be coupled to one or both sides of first implantable segment 1111 and/or second implantable segment 1112. Infusate sink 1254 may be coupled to catheter 1210. Infusate sink 1254 may be configured to consume reagents and/or reactants within the infusate that may affect performance of sensor 1120. For example, when the infusate is insulin, infusate sink 1254 may be configured to consume metacresol.

Figure 5D:
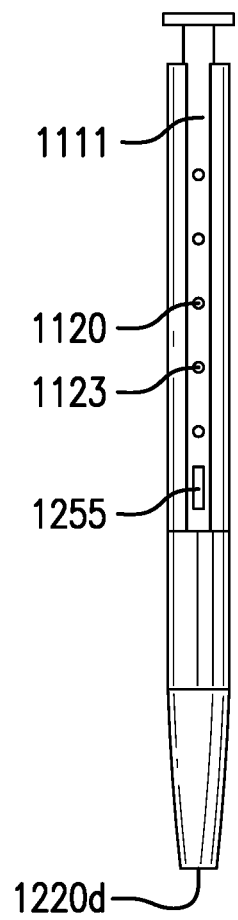

FIG. 5D shows another embodiment of backflow device 1250. Backflow device 1250 may include at least one blanking electrode 1255. Blanking electrode 1255 may be part of and/or coupled to first implantable segment 1111 and/or second implantable segment 1112. Blanking electrode 1255 may be configured to provide information about an infusate so that the information about an analyte from sensor 1120 may be adjusted. For example, blanking electrode 1255 may provide a signal about an infusate, while sensor 1120 may provide a signal about an analyte plus the infusate. The signal from blanking electrode 1255 may then be subtracted from the signal from sensor 1120 to calculate an adjusted or corrected signal about the analyte.

Figure 5E:
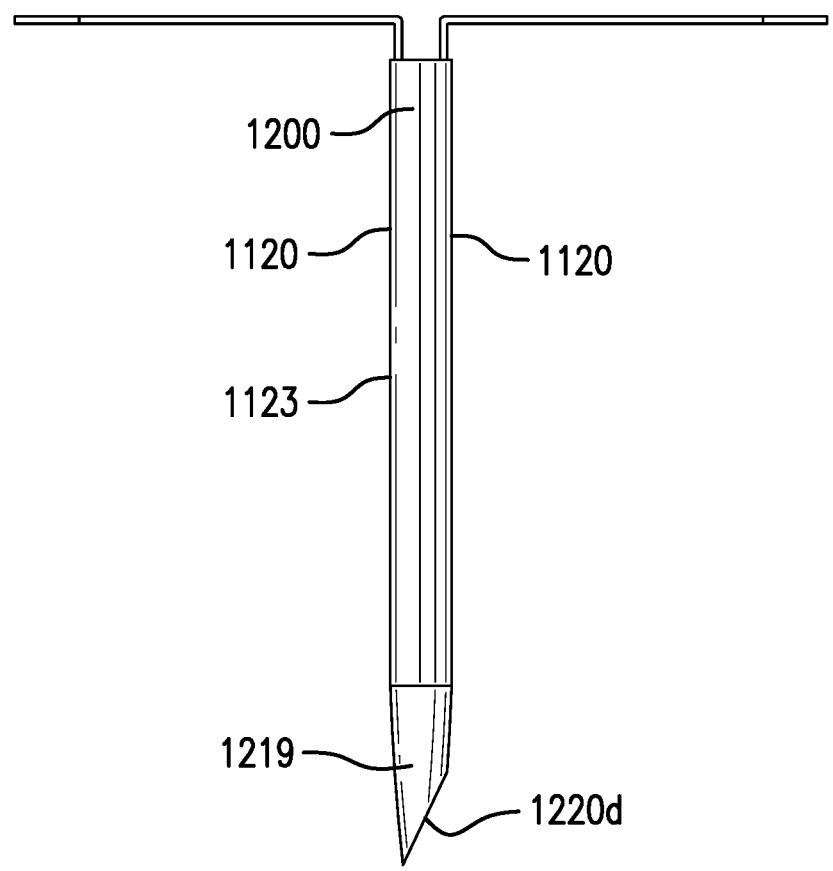

FIG. 5E shows another embodiment of backflow device 1250. Backflow device 1250 may include tip 1219 that is angled. Angled tip 1219 may be configured to direct an infusate away from sensor 1120 or a particular portion of sensor 1120. For example, angled tip 1219 may be configured to direct an infusate away from working electrode 1123. Angled tip 1219 may be angled on a side of catheter 1200 substantially opposite from working electrode 1123.

Sensing and infusion device 1000 may be used with an insertion sharp 1300. Insertion sharp 1300 may include a needle, a flat lancet, or other suitable sharp.

Insertion sharp 1300 includes a proximal portion 1300*p* and a distal portion 1300*d*.

Insertion sharp 1300 may be placed in infusion lumen 1220 of catheter 1210. Distal portion 1300*d* of insertion sharp 1300 may extend beyond distal portion 1210*d* of catheter 1210.

Alternatively, insertion sharp 1300 may be placed along a side of catheter 1210.

Figure 6A:
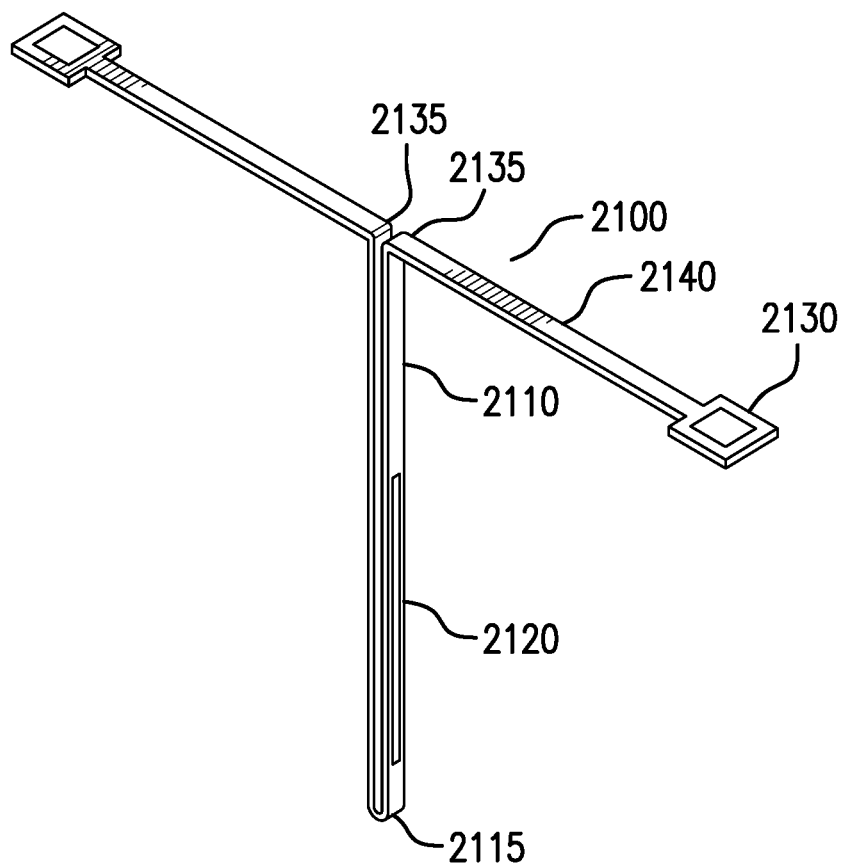
FIGS. 6A-6E show one embodiment of an in vivo sensing device 2000.
Figure 6B:
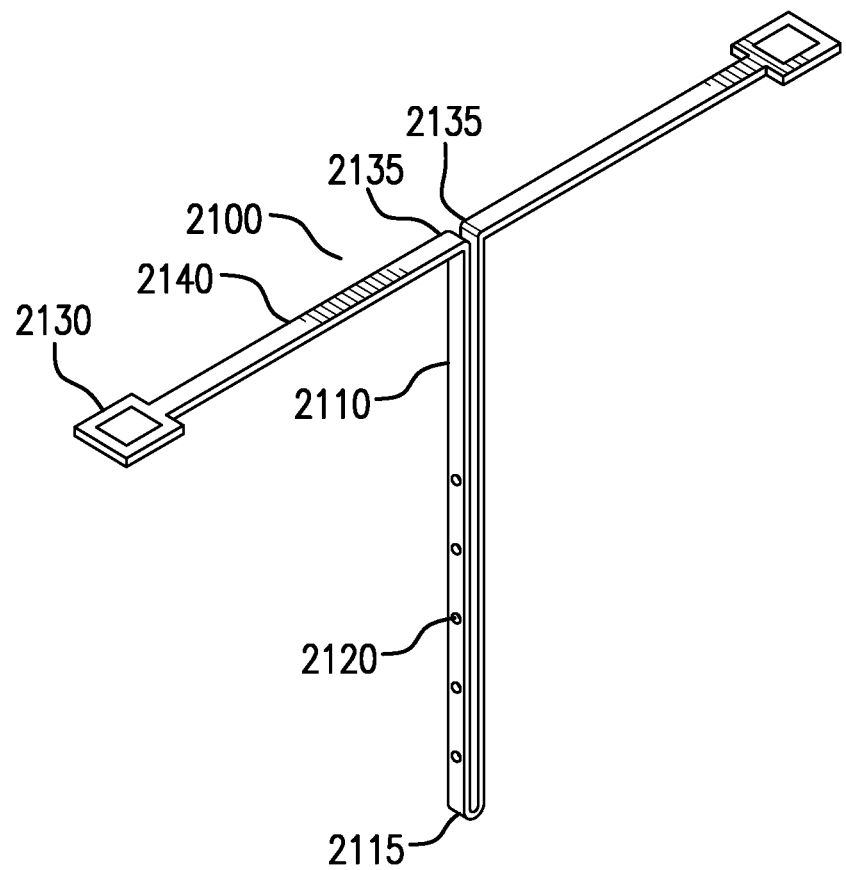
Figure 6C:
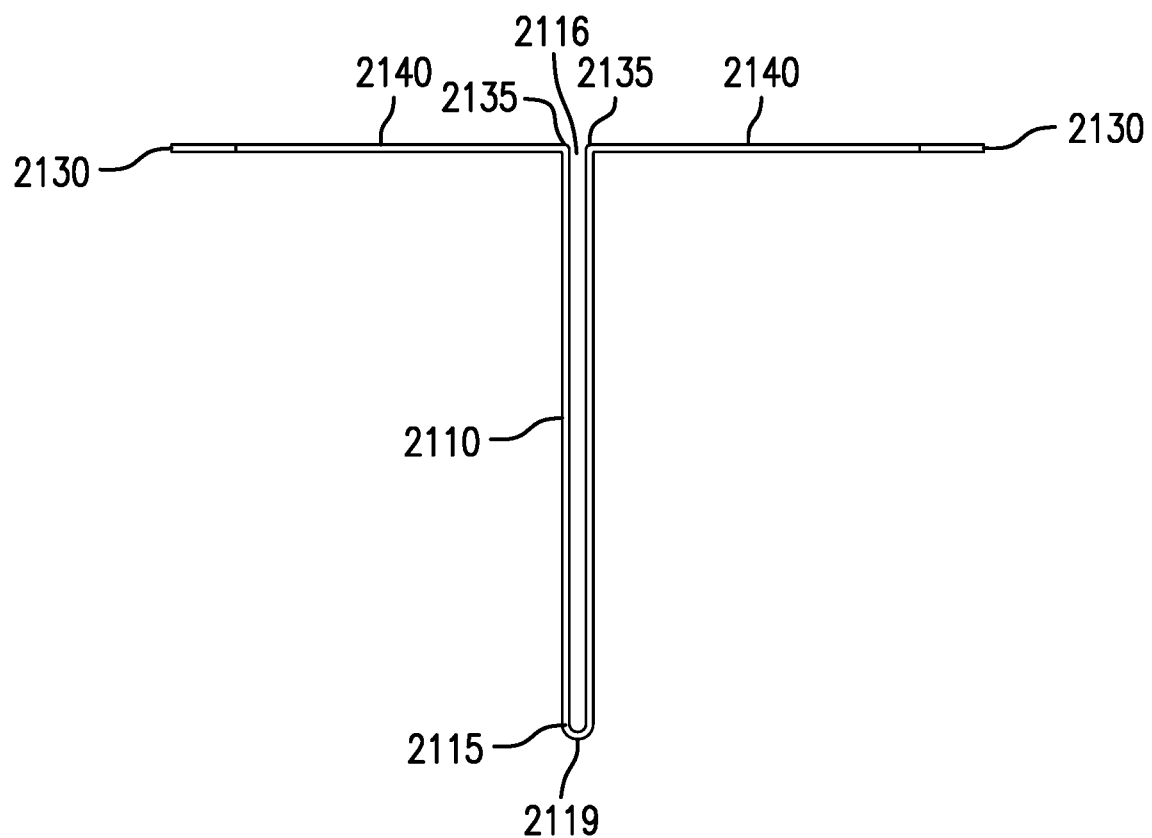
Figure 6D:
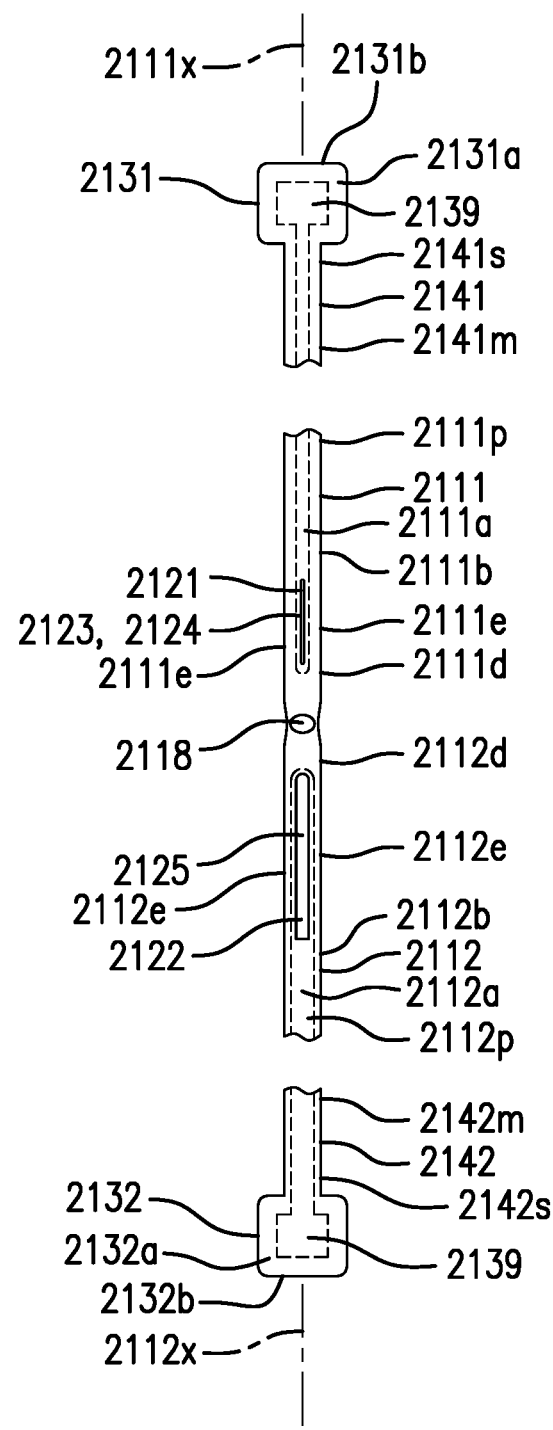

FIGS. 6A-6D show one embodiment of an in vivo sensing device 2000. FIGS. 6A-6B show perspective views of in vivo sensing device 2000. FIG. 6C shows a side view of in vivo sensing device 2000. FIG. 6D shows a flattened view of in vivo sensing device 2000.

In vivo sensing device 2000 is capable of providing information about an analyte and/or other measurements in vivo. In vivo sensing device 2000 may also be capable of delivering an infusate.

In vivo sensing device 2000 includes a sensor assembly 2100.

Sensor assembly 2100 includes an implantable body 2110. Implantable body 2110 may be configured to be at least partially implanted in an implantation site in a subject. The implantation site may be in a tissue of a body of a subject.

Implantable body 2110 may include two or more segments. Implantable body 2110 may include a first implantable segment 2111 and a second implantable segment 2112.

First implantable segment 2111 may include a proximal portion 2111*p*, a distal portion 2111*d*, a longitudinal axis 2111*x*, an outer side 2111*a*, an inner side 2111*b*, and edges 2111*e*. First implantable segment 2111 may be elongate. First implantable segment 2111 may be flat. First implantable segment 2111 may be flexible. First implantable segment 2111 may be straight or curved. First implantable segment 2111 may include one or more bends.

Second implantable segment 2112 may include a proximal portion 2112*p*, a distal portion 2112*d*, a longitudinal axis 2112*x*, an outer side 2112*a*, and an inner side 2112*b*. Second implantable segment 2112 may be elongate. Second implantable segment 2112 may be flat. Second implantable segment 2112 may be flexible. Second implantable segment 2112 may be straight or curved. Second implantable segment 2112 may include one or more bends.

First implantable segment 2111 is coupled to second implantable segment 2112. Distal portion 2111*d* of first implantable segment 2111 may be coupled to distal portion 2112*d* of second implantable segment 2112. First implantable segment 2111 and second implantable segment 2112 may be coupled by at least one bend 2115. First implantable segment 2111 and second implantable segment 2112 may be formed as a single piece that is bent at bend 2115. Bend 2115 may extend at an angle or straight across a width of implantable body 2110. Alternatively, first implantable segment 2111 and second implantable segment 2112 may be formed as separate pieces, and distal portion 2111*d* and distal portion 2112*d* may be coupled by a hinge, joint, link, or other coupling.

First implantable segment 2111 and second implantable segment 2112 may include one or more conducting layers. Bend 2115 may include one or more conducting layers. The conducting layers may include stainless steel and/or other conducting material. First implantable segment 2111 and second implantable segment 2112 may include one or more insulating layers. Bend 2115 may include one or more insulating layers. The insulating layers may include polyimide and/or other insulating material. Some or all of the layers may remain intact or unbroken at bend 2115. Bend 2115 may be a bend, fold, kink, crease, or any elastic or plastic deformation. Bend 2115 may be permanent or temporary.

First implantable segment 2111 and second implantable segment 2112 may define a space 2116 between first implantable segment 2111 and second implantable segment 2112. Space 2116 may be uniform or non-uniform in size.

First implantable segment 2111 and second implantable segment 2112 may be of the same or different lengths and/or shapes.

Bend 2115 may form a tip 2119. Tip 2119 may include an opening 2118. Opening 2118 may be a hole formed through bend 2115. Opening 2118 may be configured to receive a catheter and/or an insertion sharp. Alternatively, opening 2118 may be a pocket formed at bend 2115.

Figure 7A:
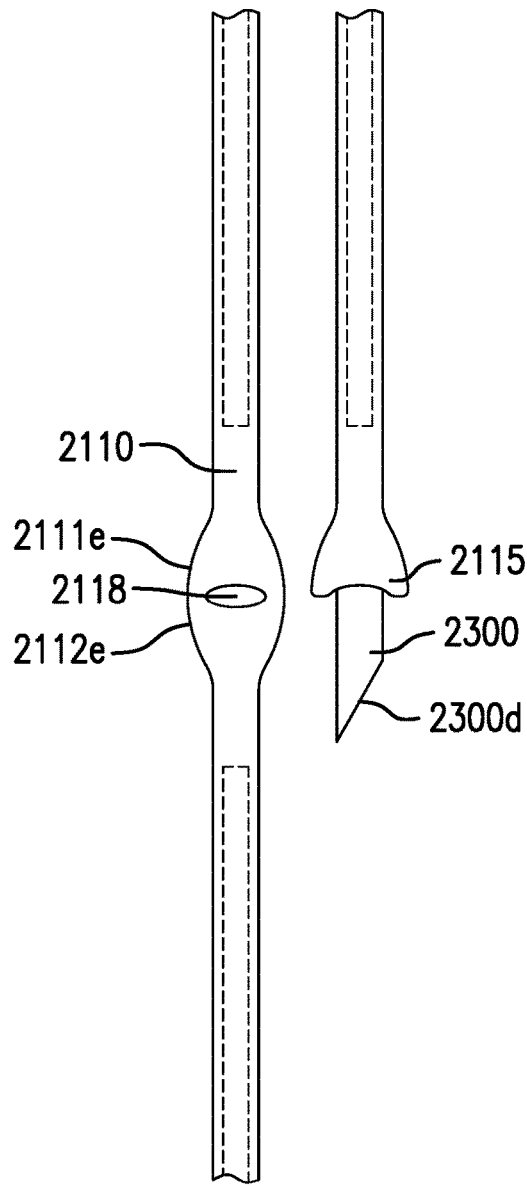
FIGS. 7A-7D show various embodiments of bend 2115.
Figure 7B:
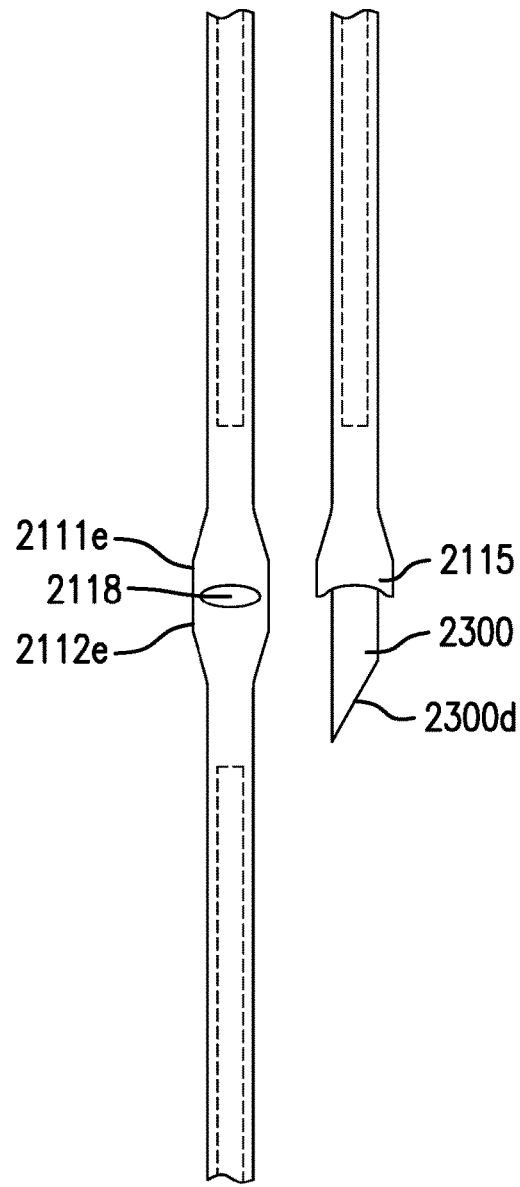
Figure 7C:
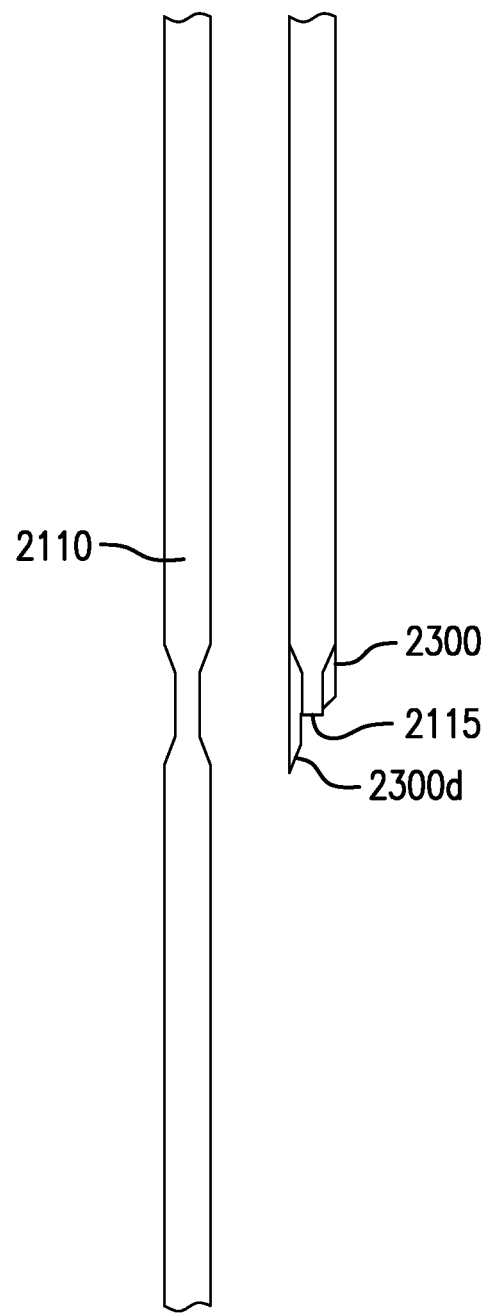
Figure 7D:
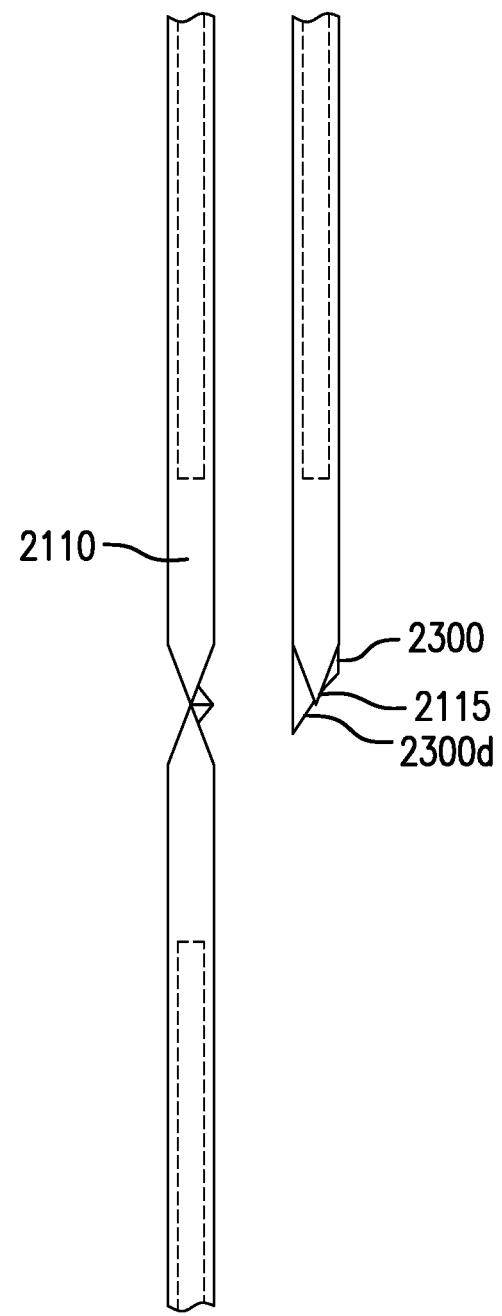

FIGS. 7A-7D show various embodiments of bend 2115. FIG. 7A shows bend 2115 with edges 2111e and edges 2112e that curve outward. FIG. 7B shows bend 2115 with edges 2111e and edges 2112e that curve inward. FIG. 7C shows bend 2115 that is narrowed, and may fit into an unsharpened portion or notch in an insertion sharp 2300. FIG. 7D shows bend 2115 having multiple bends.

Figure 6E:
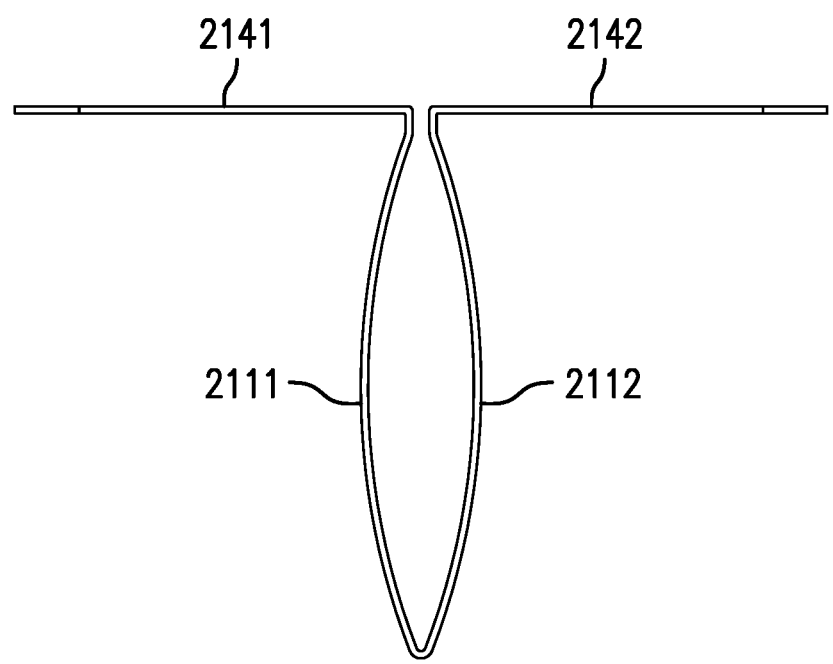

Implantable body 2110 may have spring-like properties. Implantable body 2110 may be capable of being deformed, and then spring back to its original shape. First implantable segment 2111 and second implantable segment 2112 may be configured to bow out or flex if implantable body 2110 is compressed in a longitudinal direction, as shown in FIG. 6E. This bowing out or flexing may reduce the likelihood that implantable body 2110 will break, kink, coil, or come out while implanted. This bowing out or flexing may help to refresh interstitial fluid and/or displace any blood surrounding implantable body 2110. Implantable body 2110 may have sufficient fatigue strength to last a design life of sensor assembly 2100.

Implantable body 2110 may have a U-shaped, V-shaped, W-shaped, or otherwise looped configuration where the free ends are outside of the body. This configuration has no free end inside the body, which reduces the likelihood implantable body 2110 will break and leave a piece stranded inside the body. This configuration also provides a greater sensing area for larger or more sensors.

Sensor assembly 2100 includes at least one sensor 2120. Sensor 2120 may include one or more components that are an integral part of implantable body 2110. These components may be at least partially formed as part of one or more sides and/or edges of implantable body 2110. Sensor 2120 may include one or more discrete components that are coupled to implantable body 2110.

Sensor 2120 may include one or more portions. Sensor 2120 may include a first portion 2121 that is part of and/or coupled to first implantable segment 2111. First portion 2121 may be part of and/or coupled to outer side 2111b and/or inner side 2111a of first implantable segment 2111. Sensor 2120 may include a second portion 2122 that is part of and/or coupled to second implantable segment 2112. Second portion 2122 may be part of and/or coupled to outer side 2112b and/or inner side 2112a of second implantable segment 2112.

Sensor 2120 may include one or more electrodes. Sensor 2120 may include a working electrode 2123. Sensor 2120 may include a counter electrode 2124 and/or a reference electrode 2125. Sensor 2120 may include a combined counter/reference electrode. First portion 2121 and second portion 2122 may each include any one, any combination of these electrodes. In one example, first portion 2121 of sensor 2120 may include working electrode 2123, and be part of and/or coupled to first implantable segment 2111, while second portion 2122 of sensor 2120 may include counter electrode 2124 and reference electrode 2125, and be part of and/or coupled to second implantable segment 2112. In another example, first portion 2121 of sensor 2120 may include a first set of working electrode 2123, counter electrode 2124, and reference electrode 2125, and be part of and/or coupled to first implantable segment 2111, while second portion 2122 of sensor 2120 may include a second set of working electrode 2123, counter electrode 2124, and reference electrode 2125, and be part of and/or coupled to second implantable segment 2112.

Sensor 2120 may be configured to provide information about a tissue in which sensor 2120 is implanted. Sensor 2120 may be configured to provide information about an analyte and/or other measurements. Sensor 2120 may be configured to provide information about any one or any combination of temperature, pressure, pH, hydration, and perfusion. Sensor 2120 may be configured to provide information about impedance and/or other electrical properties. Sensor 2120 may include any one or any combination of a glucose sensor, oxygen sensor, lactate sensor, or other sensor. Multiple sensors 2120 having different functions may be included. Multiple sensors 2120 having the same function, of the same or different types, may be included for redundancy.

Sensor 2120 may be configured to be in direct contact with a tissue in a body of a subject. Sensor 2120 may be open to an exterior of implantable body 2110.

Sensor assembly 2100 may include one or more contact tabs 2130. Contact tabs 2130 may be coupled to implantable body 2110. Contact tabs 2130 may be configured to rest outside of the implantation site.

Contact tabs 2130 may provide electrical connections to sensor 2120. Contact tabs 2130 may allow a computer and/or circuit to be electrically coupled to sensor 2120. Contact tabs 2130 may allow a power source to be electrically coupled to sensor 2120.

Contact tabs 2130 may include at least one tab. Contact tabs 2130 may include a first contact tab 2131. Contact tabs 2130 may include a second contact tab 2132. First contact tab 2131 may have a first side 2131a and a second side 2131b. Second contact tab 2132 may have a first side 2132a and a second side 2132b.

First contact tab 2131 may be coupled to first implantable segment 2111. First contact tab 2131 may be coupled to proximal portion 2111p of first implantable segment 2111. First contact tab 2131 and proximal portion 2111p may be coupled by at least one bend 2135. First contact tab 2131 and first implantable segment 2111 may be formed as a single piece that is bent at bend 2135. Alternatively, first contact tab 2131 and first implantable segment 2111 may be formed as separate pieces, and first contact tab 2131 and proximal portion 2111p may be coupled by a hinge, joint, link, or other coupling. First contact tab 2131 and proximal portion 2111p may be substantially perpendicular. First contact tab 2131 and proximal portion 2111p may form an angle of approximately 30 to 150 degrees. First contact tab 2131 may be flat. First contact tab 2131 may be flexible.

Second contact tab 2132 may be coupled to second implantable segment 2112. Second contact tab 2132 may be coupled to proximal portion 2112p of second implantable segment 2112. Second contact tab 2132 and proximal portion 2112p may be coupled by at least one bend 2135. Second contact tab 2132 and second implantable segment 2112 may be formed as a single piece that is bent at bend 2135. Alternatively, second contact tab 2132 and second implantable segment 2112 may be formed as separate pieces, and second contact tab 2132 and proximal portion 2112p may be coupled by a hinge, joint, link, or other coupling. Second contact tab 2132 and proximal portion 2112p may be substantially perpendicular. Second contact tab 2132 and proximal portion 2112p may form an angle of approximately 30 to 150 degrees. Second contact tab 2132 may be flat. Second contact tab 2132 may be flexible.

First contact tab 2131 and/or second contact tab 2132 may include one or more conducting layers. Bends 2135 may include one or more conducting layers. The conducting layers may include stainless steel and/or other conducting material. First contact tab 2131 and/or second contact tab 2132 may include one or more insulating layers. Bends 2135 may include one or more insulating layers. The insulating layers may include polyimide and/or other insulating material. Some or all of the layers may remain intact or unbroken at bends 2135. Bends 2135 may be a bend, fold, crease, or any elastic or plastic deformation. Bends 2135 may be permanent or temporary.

First contact tab 2131 may be coupled to first portion 2121 of sensor 2120. Second contact tab 2132 may be coupled to second portion 2122 of sensor 2120. First contact tab 2131 and second contact tab 2132 may also be coupled to second portion 2122 and first portion 2121, respectively, for redundancy.

First contact tab 2131 may include one or more contact pads 2139. Contact pads 2139 may be formed on first side 2131a and/or second side 2131b. Second contact tab 2132 may include one or more contact pads 2139. Contact pads 2139 may be formed on first side 2132a and/or second side 2132b. Contact pads 2139 may be formed by removing a portion of an insulating layer to expose a conducting layer.

Contact pads 2139 may be electrically coupled to one or more portions of sensor 2120. Contact pads 2139 may be coupled to sensor 2120 by one or more leads.

First contact tab 2131 and second contact tab 2132 may be oriented in different directions. First contact tab 2131 and second contact tab 2132 may be oriented in opposite directions. First contact tab 2131 and second contact tab 2132 may be positioned on opposite sides of implantable body 2110. This orientation may facilitate access to space 2116. This orientation in may balance sensor assembly 2100 and reduce the likelihood of damage or coming out of the implantation site. This orientation and/or positioning may allow first contact tab 2131 and second contact tab 2132 to be spaced apart. This spacing apart may provide room to make electrical connections to first contact tab 2131 and second contact tab 2132, such as to an on-body worn device (OBWD). This spacing apart may provide room to make bulky hermetic or airtight seals for electrical connections to first contact tab 2131 and/or second contact tab 2132. In one example, first contact tab 2131 and second contact tab 2132 may be separated by 3 mm or more.

First contact tab 2131 and second contact tab 2132 may be capable of lying flat against and/or parallel to an outside surface of the implantation site. This may allow a portion of in vivo sensing device 2000 outside of the implantation site to have a reduced height and/or size.

Sensor assembly 2100 may include one or more spacer arms 2140. Spacer arms 2140 may be coupled to implantable body 2110 and contact tabs 2130. Spacer arms 2140 may be coupled between implantable body 2110 and contact tabs 2130.

Spacer arms 2140 may include a first spacer arm 2141. First spacer arm 2141 may include a medial portion 2141m and a side portion 2141s. Spacer arms 2140 may include a second spacer arm 2142. Second spacer arm 2142 may include a medial portion 2142m and a side portion 2142s.

First spacer arm 2141 may be coupled to first implantable segment 2111 and first contact tab 2131. Medial portion 2141m of first spacer arm 2141 may be coupled to proximal portion 2111p of first implantable segment 2111. Side portion 2141s of first spacer arm 2141 may be coupled to first contact tab 2131. Medial portion 2141m and proximal portion 2111p may be coupled by at least one bend 2135. First spacer arm 2141 and first implantable segment 2111 may be formed as a single piece that is bent at bend 2135. Alternatively, first spacer arm 2141 and first implantable segment 2111 may be formed as separate pieces, and medial portion 2141m and proximal portion 2111p may be coupled by a hinge, joint, link, or other coupling. Medial portion 2141m and proximal portion 2111p may be substantially perpendicular. Medial portion 2141m and proximal portion 2111p may form an angle of approximately 30 to 150 degrees. First spacer arm 2141 may be elongate. First spacer arm 2141 may be flat. First spacer arm 2141 may be flexible. First spacer arm 2141 may be straight or curved. First spacer arm 2141 may include one or more bends.

Second spacer arm 2142 may be coupled to second implantable segment 2112 and second contact tab 2132. Medial portion 2142m of second spacer arm 2142 may be coupled to proximal portion 2112p of second implantable segment 2112. Side portion 2142s of second spacer arm 2142 may be coupled to second contact tab 2132. Medial portion 2142m and proximal portion 2112p may be coupled by at least one bend 2135. Second spacer arm 2142 and second implantable segment 2112 may be formed as a single piece that is bent at bend 2135. Alternatively, second spacer arm 2142 and second implantable segment 2112 may be formed as separate pieces, and medial portion 2142m and proximal portion 2112p may be coupled by a hinge, joint, link, or other coupling. Medial portion 2142m and proximal portion 2112p may be substantially perpendicular. Medial portion 2142m and proximal portion 2112p may form an angle of approximately 30 to 150 degrees. Second spacer arm 2142 may be elongate. Second spacer arm 2142 may be flat. Second spacer arm 2142 may be flexible. Second spacer arm 2142 may be straight or curved. Second spacer arm 2142 may include one or more bends 1145.

First spacer arm 2141 and/or second spacer arm 2142 may include one or more conducting layers. Bends 2145 may include one or more conducting layers. The conducting layers may include stainless steel and/or other conducting material. First spacer arm 2141 and/or second spacer arm 2142 may include one or more insulating layers. bends 2145 may include one or more insulating layers. The insulating layers may include polyimide and/or other insulating material.

First spacer arm 2141 and second spacer arm 2142 may be oriented in different directions. First spacer arm 2141 and second spacer arm 2142 may be oriented in opposite directions. First spacer arm 2141 and second spacer arm 2142 may be oriented in the same direction. First spacer arm 2141 and second spacer arm 2141 may be positioned on opposite sides of implantable body 2110. First spacer arm 2141 and second spacer arm 2142 may be positioned on the same side of implantable body 2110. First spacer arm 2141 and second spacer arm 2142 may be of the same or different lengths and/or shapes.

First spacer arm 2141 and second spacer arm 2142 may be capable of lying flat against and/or parallel to an outside surface of the implantation site. This may allow a portion of in vivo sensing device 2000 outside of the implantation site to have a reduced height and/or size.

First spacer arm 2141 and second spacer arm 2142 may allow first contact tab 2131 and second contact tab 2132 to be spaced apart. First spacer arm 2141 and second spacer arm 2142 may allow a distance and positioning between first contact tab 2131 and second contact tab 2132 to be adjusted. This distance and positioning may provide space to make electrical connections to first contact tab 2131 and second contact tab 2132, such as to an on-body worn device (OBWD). This distance and positioning may provide space to make bulky electrical connections to first contact tab 2131 and/or second contact tab 2132. For example, first contact tab 2131 and/or second contact tab 2132 may require a bulky hermetic or airtight seal when coupled to working electrode 2123.

First spacer arm 2141 and second spacer arm 2142 may have spring-like properties. First spacer arm 2141 and second spacer arm 2142 may be capable of being deformed, and then spring back to their original shapes. First spacer arm 2141 and second spacer arm 2142 may be configured to bias implantable body 2110 back into the implantation site when implantable body 2110 travels at least partially out of the implantation site. First spacer arm 2141 and second spacer arm 2142 may be configured to bias implantable body 2110 in a distal direction when implantable body 2110 travels in a proximal direction. This travel may help to refresh interstitial fluid and/or displace any blood surrounding implantable body 2110. First implantable segment 2111 and second implantable segment 2112 may have sufficient stiffness to be pushed back into the implantation site instead of buckling or bunching in an accordion-like fashion outside of the implantation site. First spacer arm 2141 and second spacer arm 2142 may have sufficient fatigue strength to last a design life of sensor assembly 2100.

Figure 8A:
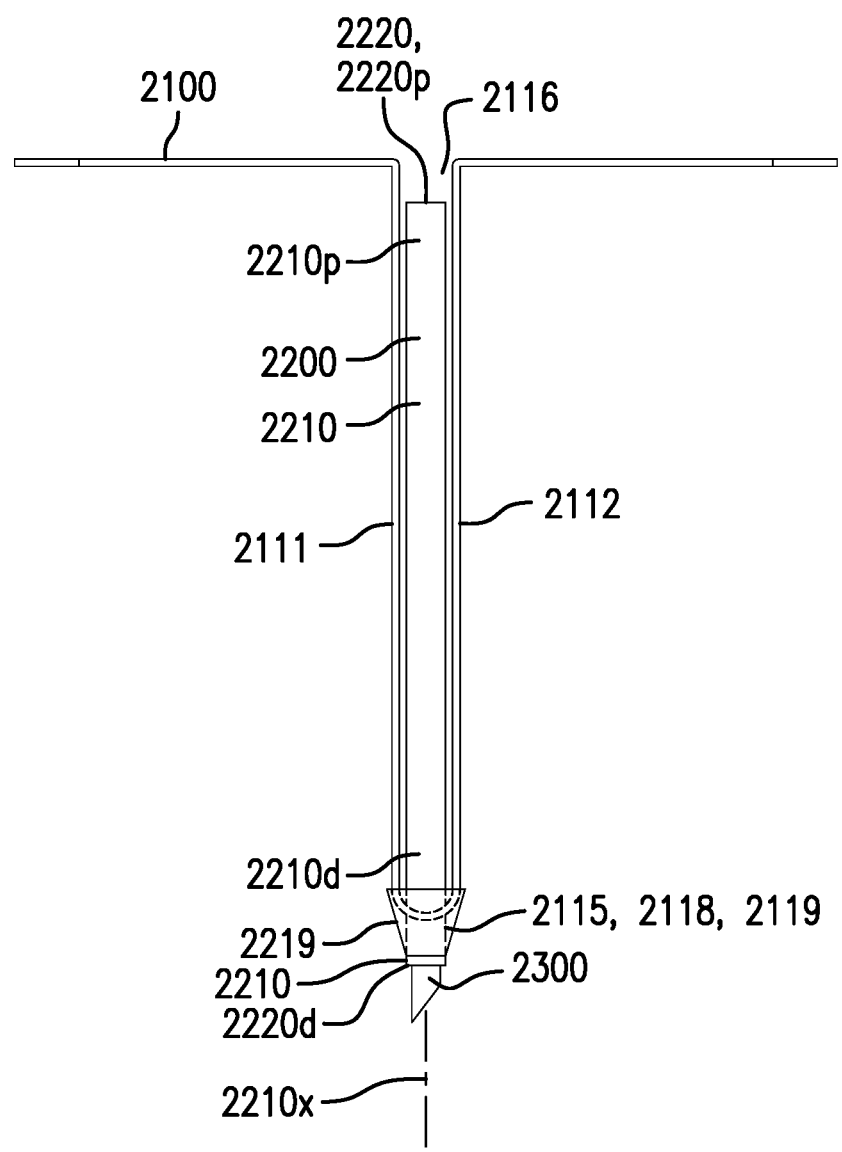
FIGS. 8A-8B show in vivo sensing device 2000 with a catheter assembly 2200.

Sensor assembly 2100 may be used with a catheter assembly 2200, as shown in FIG. 8A. Catheter assembly 2200 is configured to be at least partially placed in the implantation site. Catheter assembly 2200 includes at least one catheter 2210.

Catheter 2210 includes a proximal portion 2210p, a distal portion 2210d, and a longitudinal axis 2210x. Catheter 2210 may have a cross section that is circular. Alternatively, catheter 2210 may have a cross section that is oval, square, triangular, or other suitable shape. Catheter 2210 may be flexible.

Catheter 2210 may be at least partially positioned in space 2116 between first implantable segment 2111 and second implantable segment 2112. Catheter 2210 may be used with opening 2118. Distal portion 2210d of catheter 2210 may be inserted into opening 2118.

Catheter 2210 may include an infusion lumen 2220 formed in catheter 2210. Infusion lumen 2220 may have a distal end 2220d that is open or closed. Catheter 2210 may include one or more infusion ports formed in catheter 2210. Infusion ports may be in fluid communication with infusion lumen 2220. Infusion ports may be formed in a side of catheter 2210.

Catheter 2210 may include a tip 2219 at distal portion 2210d of catheter 2210. Tip 2219 may be soft and tapered. Tip 2219 may be formed as a separate piece or part of catheter 2210.

Figure 8B:
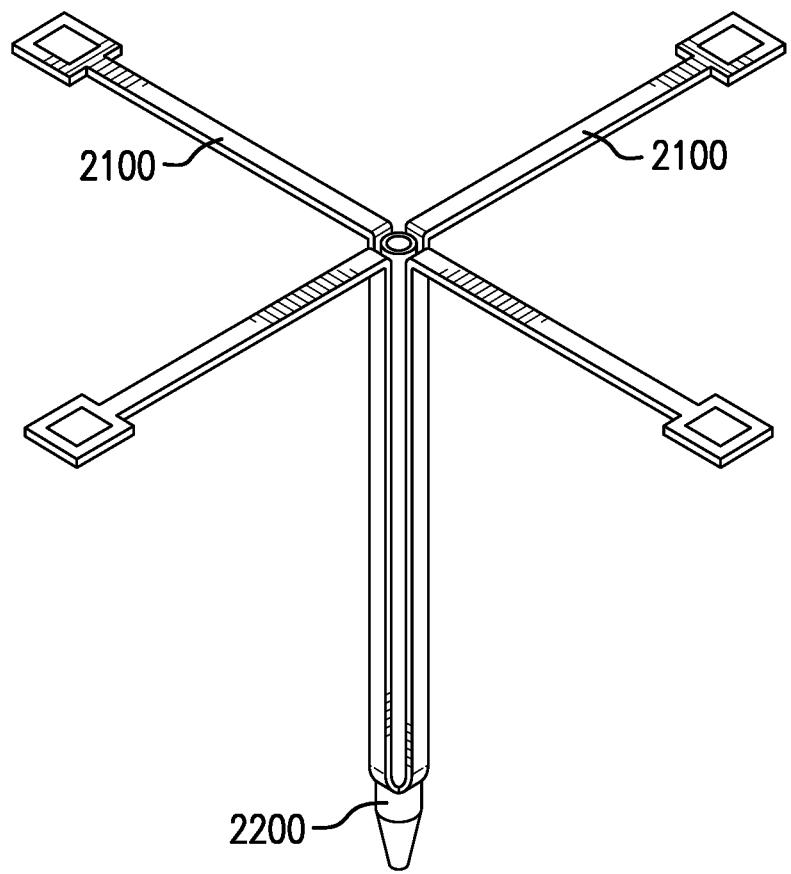

More than one sensor assembly 2100 may be used with catheter assembly 2200, as shown in FIG. 8B.

Figure 8C:
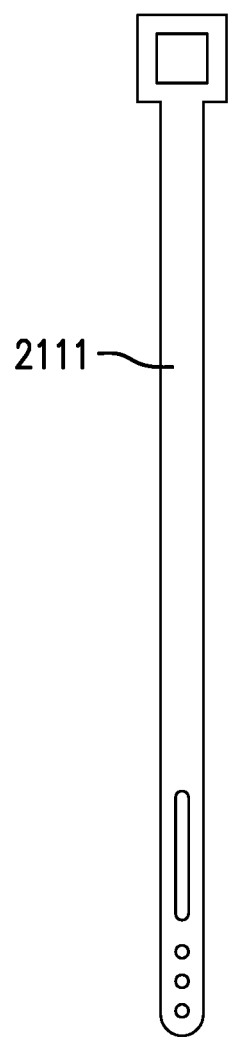
FIGS. 8C-8E show in vivo sensing device 2000 with an infusion lumen 2117.
Figure 8D:
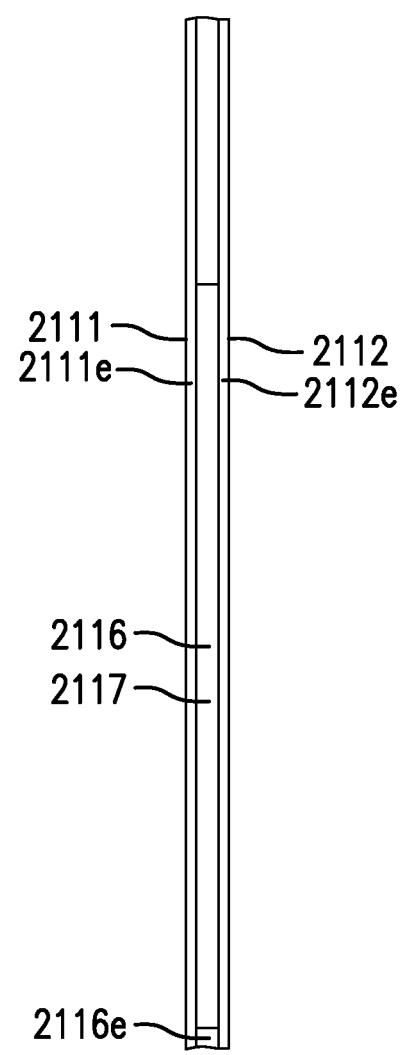
Figure 8E:
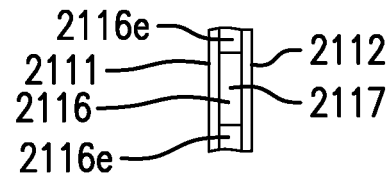

FIGS. 8C-8E show in vivo sensing device 2000 having an infusion lumen 2117 formed by at least partially enclosing space 2116. FIG. 8C shows a side view of in vivo sensing device 2000. FIG. 8D shows a side cross-sectional view of in vivo sensing device 2000. FIG. 8E shows an end cross-sectional view of in vivo sensing device 2000. Edges 2111e of first implantable segment 2111 may be at least partially sealed with edges 2112e of second implantable segment 2112 to enclose space 2116. For example, edges 2111e and edges 2112e may be sealed with an edge material 2116e such as silicone which encloses space 2116 and forms infusion lumen 2117. As another example, a sacrificial material and an edge material 2116e, such as an insulator, may be sandwiched between first implantable segment 2111 and second implantable segment 2112. The sacrificial material may be removed, leaving edge material 2116e which encloses space 2116 and forms infusion lumen 2117. Infusion ports may be formed in first implantable segment 2111 and/or second implantable segment 2112.

In vivo sensing device 2000 may be used with an insertion sharp 2300. Insertion sharp 2300 may include a needle, a flat lancet, or other suitable sharp.

Insertion sharp 2300 includes a proximal portion 2300p and a distal portion 2300d.

Insertion sharp 2300 may be used with in vivo sensing device 2000 without catheter assembly 2200. Insertion sharp 2300 may be at least partially placed in space 2116 between first implantable segment 2111 and second implantable segment 2112. Distal portion 2300d of insertion sharp 2300 may be placed in opening 2118.

Insertion sharp 2300 may be used with in vivo sensing device 2000 having catheter assembly 2200. Insertion sharp 2300 may be placed in infusion lumen 2220 of catheter 2210. Distal portion 2300d of insertion sharp 2300 may extend beyond distal portion 2210d of catheter 2210.

Alternatively, insertion sharp 2300 may be placed along a side of first implantable segment 2111 or second implantable segment 2112.

Figure 9A:
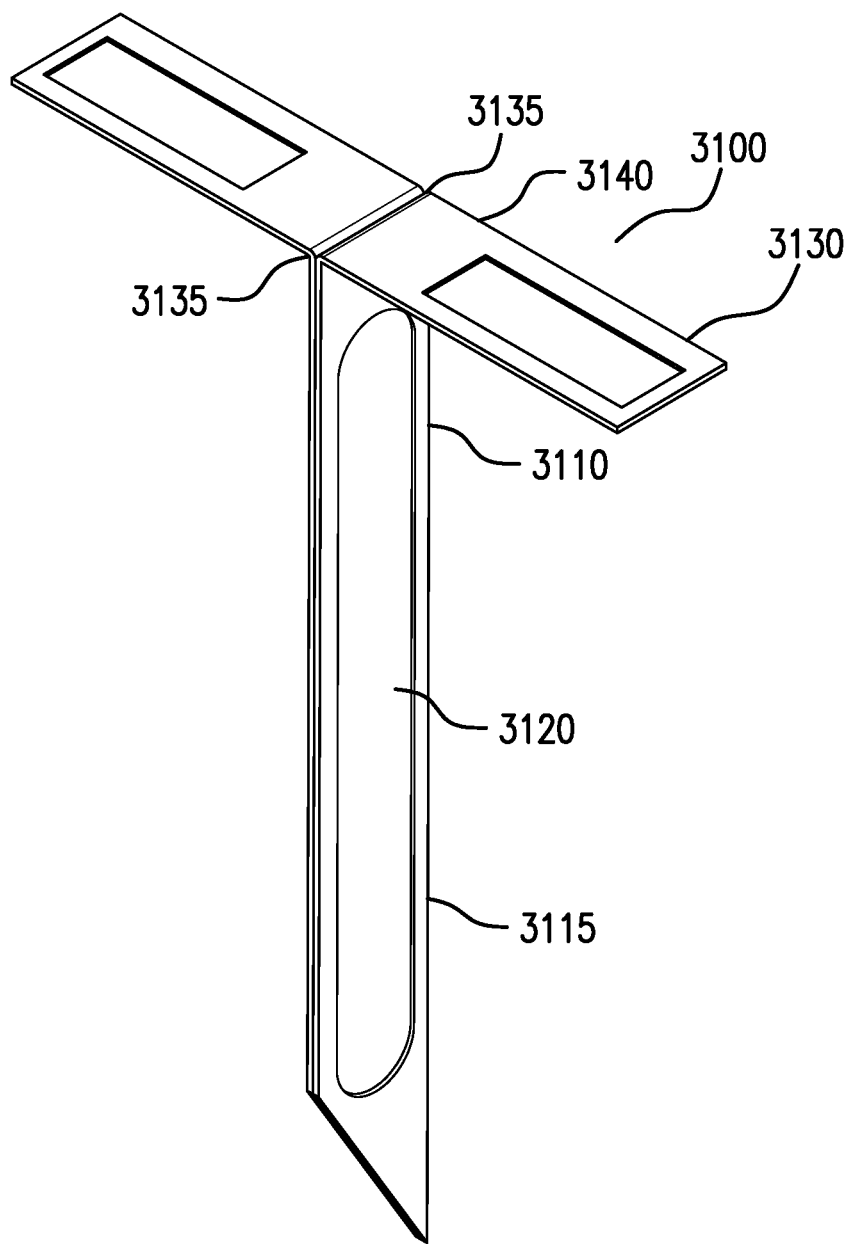
FIGS. 9A-9E show one embodiment of an in vivo sensing device 3000.
Figure 9B:
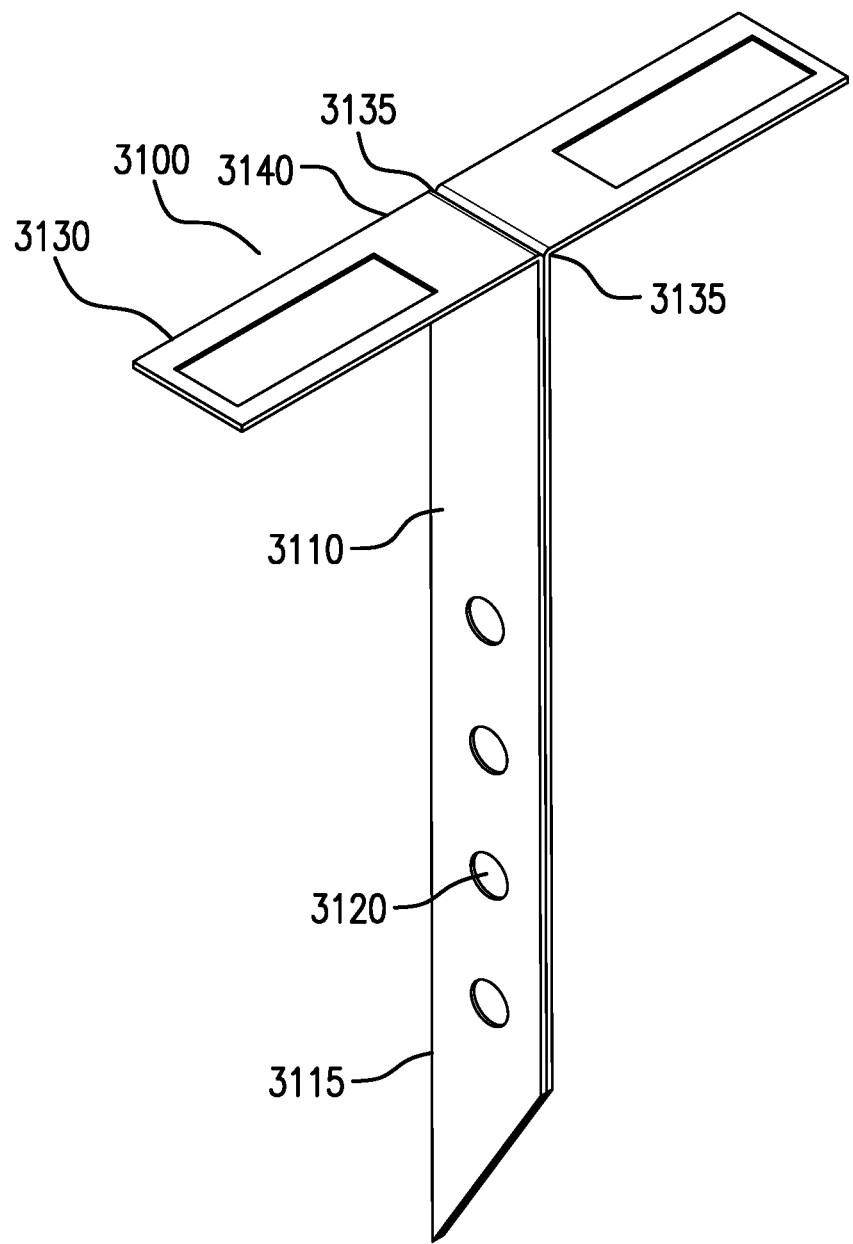
Figure 9C:
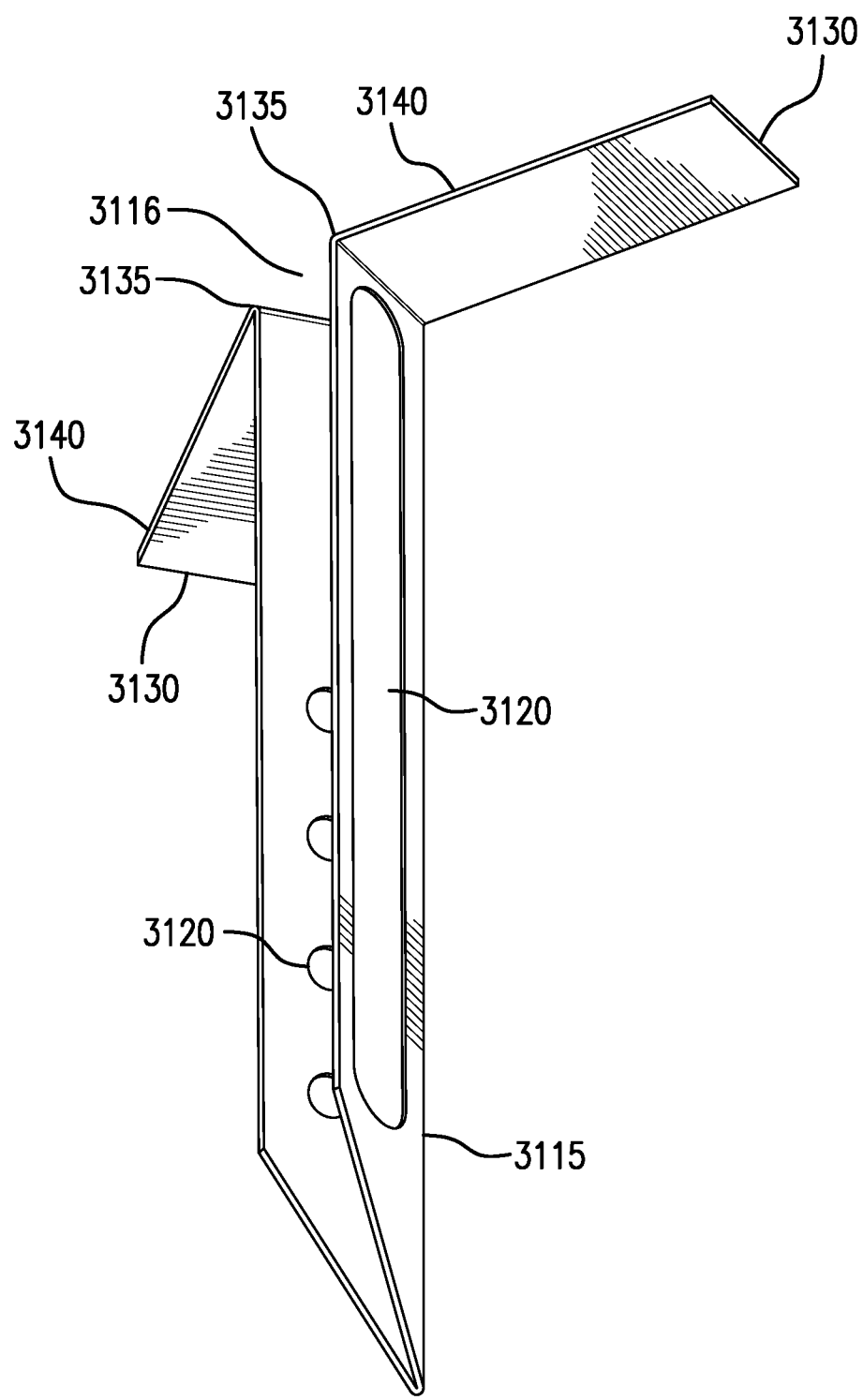
Figure 9D:
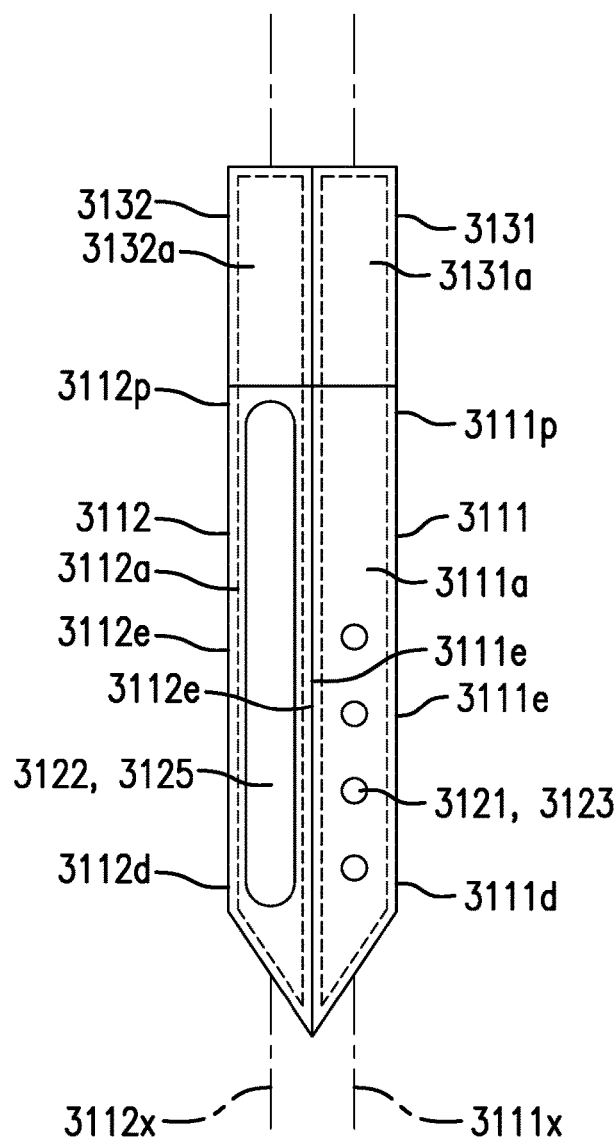
Figure 9E:
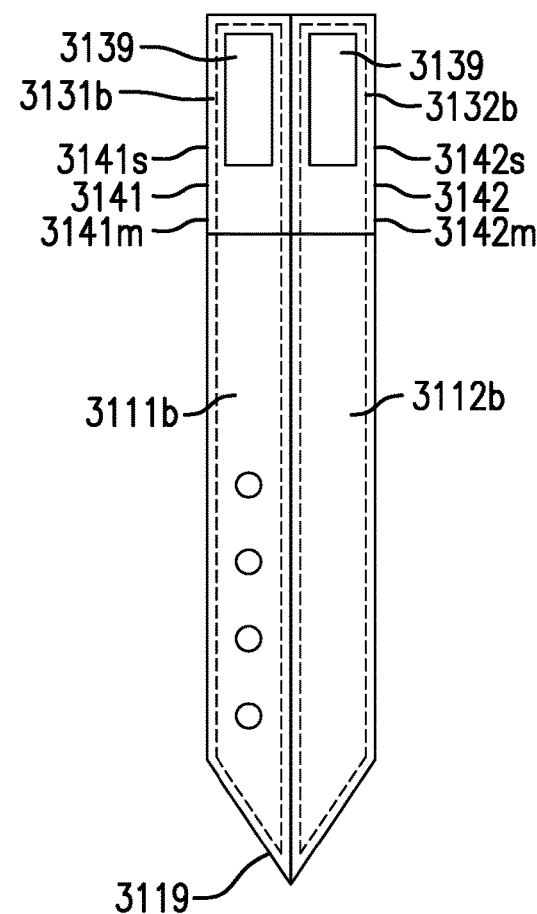

FIGS. 9A-9E show one embodiment of an in vivo sensing device 3000. FIGS. 9A-9B show perspective views of in vivo sensing device 3000. FIG. 9C shows a partially opened view of in vivo sensing device 3000. FIGS. 9D-9E show a flattened view of in vivo sensing device 3000.

In vivo sensing device 3000 is capable of providing information about an analyte and/or other measurements in vivo. In vivo sensing device 3000 may also be capable of delivering an infusate.

In vivo sensing device 3000 includes a sensor assembly 3100.

Sensor assembly 3100 includes an implantable body 3110. Implantable body 3110 may be configured to be at least partially implanted in an implantation site in a subject. The implantation site may be in a tissue of a body of a subject.

Implantable body 3110 may include two or more segments. Implantable body 3110 may include a first implantable segment 3111 and a second implantable segment 3112.

First implantable segment 3111 may include a proximal portion 3111p, a distal portion 3111d, a longitudinal axis 3111x, an outer side 3111a, an inner side 3111b, and edges 3111e. First implantable segment 3111 may be elongate. First implantable segment 3111 may be flat. First implantable segment 3111 may be flexible. First implantable segment 3111 may be straight or curved. First implantable segment 3111 may include one or more bends.

Second implantable segment 3112 may include a proximal portion 3112p, a distal portion 3112d, a longitudinal axis 3112x, an outer side 3112a, and an inner side 3112b. Second implantable segment 3112 may be elongate. Second implantable segment 3112 may be flat. Second implantable segment 3112 may be flexible. Second implantable segment 3112 may be straight or curved. Second implantable segment 3112 may include one or more bends.

Figure 10A:
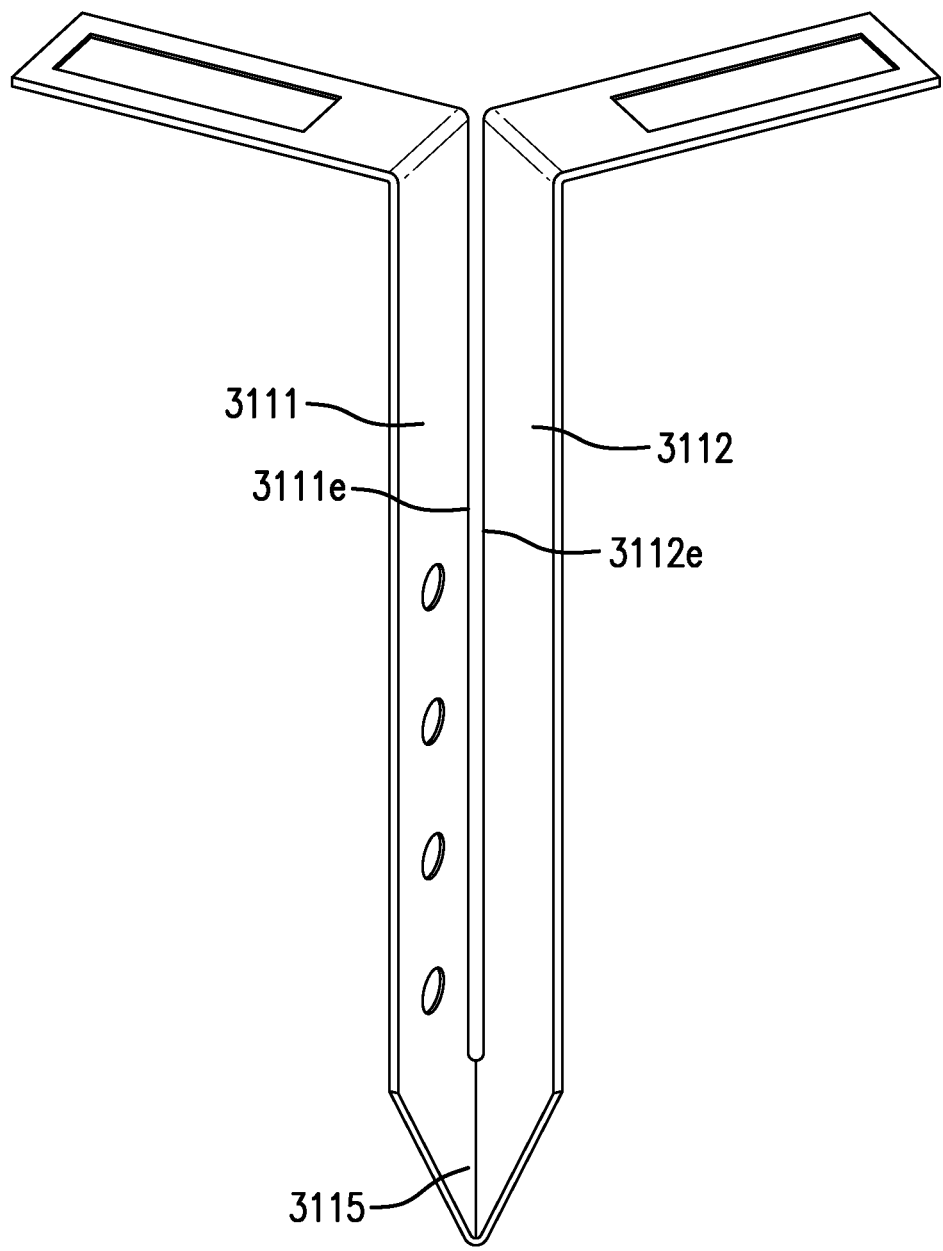
FIGS. 10A-10B show another embodiment of in vivo sensing device 3000.

First implantable segment 3111 is coupled to second implantable segment 3112. First implantable segment 3111 may be coupled to second implantable segment 3112 along edge 3111e of first implantable segment 3111 and edge 3112e of second implantable segment 3112. First implantable segment 3111 may be coupled to second implantable segment 3112 along a portion of edge 3111e of first implantable segment 3111 and edge 3112e of second implantable segment 3112, as shown in FIG. 10A. First implantable segment 3111 and second implantable segment 3112 may form an angle of between 0 and 90 degrees. First implantable segment 3111 and second implantable segment 3112 may be coupled by at least one bend 3115. First implantable segment 3111 and second implantable segment 3112 may be formed as a single piece that is bent at bend 3115. Bend 3115 may extend lengthwise along implantable body 3110. Alternatively, first implantable segment 3111 and second implantable segment 3112 may be formed as separate pieces, and distal portion 3111*d* and distal portion 3112*d* may be coupled by a hinge, joint, link, or other coupling.

First implantable segment 3111 and second implantable segment 3112 may include one or more conducting layers. Bend 3115 may include one or more conducting layers. The conducting layers may include stainless steel and/or other conducting material. First implantable segment 3111 and second implantable segment 3112 may include one or more insulating layers. Bend 3115 may include one or more insulating layers. The insulating layers may include polyimide and/or other insulating material. Some or all of the layers may remain intact or unbroken at bend 3115. Bend 3115 may be a bend, fold, kink, crease, or any elastic or plastic deformation. Bend 3115 may be permanent or temporary.

First implantable segment 3111 and second implantable segment 3112 may define a space 3116 between first implantable segment 3111 and second implantable segment 3112. Space 3116 may be uniform or non-uniform in size.

First implantable segment 3111 and second implantable segment 3112 may be of the same or different lengths and/or shapes.

Distal portion 3111*d* and/or distal portion 3112*d* may include a tip 3119. Tip 3119 may be pointed and/or sharpened. Distal portion 3111*d* and distal portion 3112*d* may be at least partially coupled, such as with an adhesive.

Figure 10B:
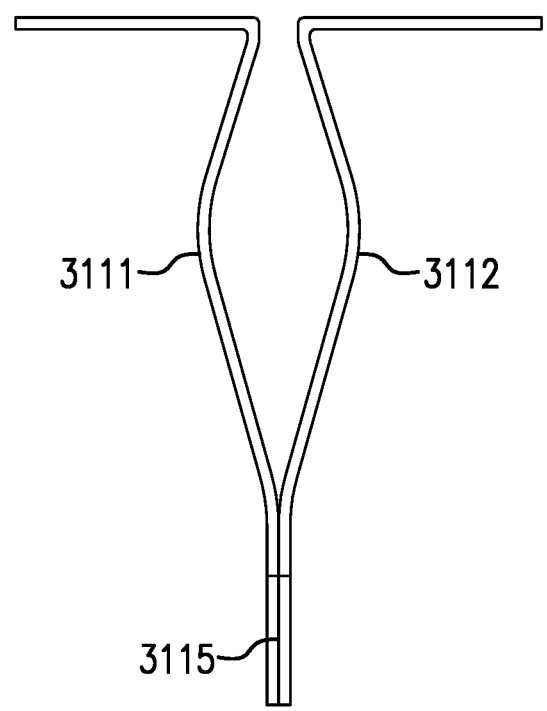

Implantable body 3110 may have spring-like properties. Implantable body 3110 may be capable of being deformed, and then spring back to its original shape. First implantable segment 3111 and second implantable segment 3112 may be configured to bow out or flex if implantable body 3110 is compressed in a longitudinal direction, as shown in FIG. 10B. This bowing out or flexing may reduce the likelihood that implantable body 3110 will break, kink, coil, or come out while implanted. This bowing out or flexing may help to refresh interstitial fluid and/or displace any blood surrounding implantable body 3110. Implantable body 3110 may have sufficient fatigue strength to last a design life of sensor assembly 3100.

Implantable body 3110 may have a looped configuration where the free ends are outside of the body. This configuration has no free end inside the body, which reduces the likelihood implantable body 3110 will break and leave a piece stranded inside the body. This configuration also provides a greater sensing area for larger or more sensors.

Sensor assembly 3100 includes at least one sensor 3120. Sensor 3120 may include one or more components that are an integral part of implantable body 3110. These components may be at least partially formed as part of one or more sides and/or edges of implantable body 3110. Sensor 3120 may include one or more discrete components that are coupled to implantable body 3110.

Sensor 3120 may include one or more portions. Sensor 3120 may include a first portion 3121 that is part of and/or coupled to first implantable segment 3111. First portion 3121 may be part of and/or coupled to outer side 3111*b* and/or inner side 3111*a* of first implantable segment 3111. Sensor 3120 may include a second portion 3122 that is part of and/or coupled to second implantable segment 3112. Second portion 3122 may be part of and/or coupled to outer side 3112*b* and/or inner side 3112*a* of second implantable segment 3112.

Sensor 3120 may include one or more electrodes. Sensor 3120 may include a working electrode 3123. Sensor 3120 may include a counter electrode 3124 and/or a reference electrode 3125. Sensor 3120 may include a combined counter/reference electrode. First portion 3121 and second portion 3122 may each include any one, any combination of these electrodes. In one example, first portion 3121 of sensor 3120 may include working electrode 3123, and be part of and/or coupled to first implantable segment 3111, while second portion 3122 of sensor 3120 may include counter electrode 3124 and reference electrode 3125, and be part of and/or coupled to second implantable segment 3112. In another example, first portion 3121 of sensor 3120 may include a first set of working electrode 3123, counter electrode 3124, and reference electrode 3125, and be part of and/or coupled to first implantable segment 3111, while second portion 3122 of sensor 3120 may include a second set of working electrode 3123, counter electrode 3124, and reference electrode 3125, and be part of and/or coupled to second implantable segment 3112.

Sensor 3120 may be configured to provide information about a tissue in which sensor 3120 is implanted. Sensor 3120 may be configured to provide information about an analyte and/or other measurements. Sensor 3120 may be configured to provide information about any one or any combination of temperature, pressure, pH, hydration, and perfusion. Sensor 3120 may be configured to provide information about impedance and/or other electrical properties. Sensor 3120 may include any one or any combination of a glucose sensor, oxygen sensor, lactate sensor, or other sensor. Multiple sensors 3120 having different functions may be included. Multiple sensors 3120 having the same function, of the same or different types, may be included for redundancy.

Sensor 3120 may be configured to be in direct contact with a tissue in a body of a subject. Sensor 3120 may be open to an exterior of implantable body 3110.

Sensor assembly 3100 may include one or more contact tabs 3130. Contact tabs 3130 may be coupled to implantable body 3110. Contact tabs 3130 may be configured to rest outside of the implantation site.

Contact tabs 3130 may provide electrical connections to sensor 3120. Contact tabs 3130 may allow a computer and/or circuit to be electrically coupled to sensor 3120. Contact tabs 3130 may allow a power source to be electrically coupled to sensor 3120.

Contact tabs 3130 may include at least one tab. Contact tabs 3130 may include a first contact tab 3131. Contact tabs 3130 may include a second contact tab 3132. First contact tab 3131 may have a first side 3131*a* and a second side 3131*b*. Second contact tab 3132 may have a first side 3132*a* and a second side 3132*b*.

First contact tab 3131 and second contact tab 3132 may be separate. First contact tab 3131 and second contact tab 3132 may be separated by a cut or a slit.

First contact tab 3131 may be coupled to first implantable segment 3111. First contact tab 3131 may be coupled to proximal portion 3111*p* of first implantable segment 3111. First contact tab 3131 and proximal portion 3111*p* may be coupled by at least one bend 3135. First contact tab 3131 and first implantable segment 3111 may be formed as a single piece that is bent at bend 3135. Alternatively, first contact tab 3131 and first implantable segment 3111 may be formed as separate pieces, and first contact tab 3131 and proximal portion 3111p may be coupled by a hinge, joint, link, or other coupling. First contact tab 3131 and proximal portion 3111p may be substantially perpendicular. First contact tab 3131 and proximal portion 3111p may form an angle of approximately 30 to 150 degrees. First contact tab 3131 may be flat. First contact tab 3131 may be flexible.

Second contact tab 3132 may be coupled to second implantable segment 3112. Second contact tab 3132 may be coupled to proximal portion 3112p of second implantable segment 3112. Second contact tab 3132 and proximal portion 3112p may be coupled by at least one bend 3135. Second contact tab 3132 and second implantable segment 3112 may be formed as a single piece that is bent at bend 3135. Alternatively, second contact tab 3132 and second implantable segment 3112 may be formed as separate pieces, and second contact tab 3132 and proximal portion 3112p may be coupled by a hinge, joint, link, or other coupling. Second contact tab 3132 and proximal portion 3112p may be substantially perpendicular. Second contact tab 3132 and proximal portion 3112p may form an angle of approximately 30 to 150 degrees. Second contact tab 3132 may be flat. Second contact tab 3132 may be flexible.

First contact tab 3131 and/or second contact tab 3132 may include one or more conducting layers. Bends 3135 may include one or more conducting layers. The conducting layers may include stainless steel and/or other conducting material. First contact tab 3131 and/or second contact tab 3132 may include one or more insulating layers. Bends 3135 may include one or more insulating layers. The insulating layers may include polyimide and/or other insulating material. Some or all of the layers may remain intact or unbroken at bends 3135. Bends 3135 may be a bend, fold, crease, or any elastic or plastic deformation. Bends 3135 may be permanent or temporary.

First contact tab 3131 may be coupled to first portion 3121 of sensor 3120. Second contact tab 3132 may be coupled to second portion 3122 of sensor 3120. First contact tab 3131 and second contact tab 3132 may also be coupled to second portion 3122 and first portion 3121, respectively, for redundancy.

First contact tab 3131 may include one or more contact pads 3139. Contact pads 3139 may be formed on first side 3131a and/or second side 3131b. Second contact tab 3132 may include one or more contact pads 3139. Contact pads 3139 may be formed on first side 3132a and/or second side 3132b. Contact pads 3139 may be formed by removing a portion of an insulating layer to expose a conducting layer.

Contact pads 3139 may be electrically coupled to one or more portions of sensor 3120. Contact pads 3139 may be coupled to sensor 3120 by one or more leads.

First contact tab 3131 and second contact tab 3132 may be oriented in different directions. First contact tab 3131 and second contact tab 3132 may be oriented in opposite directions. First contact tab 3131 and second contact tab 3132 may be positioned on opposite sides of implantable body 3110. This orientation may facilitate access to space 3116. This orientation in may balance sensor assembly 3100 and reduce the likelihood of damage or coming out of the implantation site. This orientation and/or positioning may allow first contact tab 3131 and second contact tab 3132 to be spaced apart. This spacing apart may provide room to make electrical connections to first contact tab 3131 and second contact tab 3132, such as to an on-body worn device (OBWD). This spacing apart may provide room to make bulky hermetic or airtight seals for electrical connections to first contact tab 3131 and/or second contact tab 3132. In one example, first contact tab 3131 and second contact tab 3132 may be separated by 3 mm or more.

First contact tab 3131 and second contact tab 3132 may be capable of lying flat against and/or parallel to an outside surface of the implantation site. This may allow a portion of in vivo sensing device 3000 outside of the implantation site to have a reduced height and/or size.

Sensor assembly 3100 may include one or more spacer arms 3140. Spacer arms 3140 may be coupled to implantable body 3110 and contact tabs 3130. Spacer arms 3140 may be coupled between implantable body 3110 and contact tabs 3130.

Spacer arms 3140 may include a first spacer arm 3141. First spacer arm 3141 may include a medial portion 3141m and a side portion 3141s. Spacer arms 3140 may include a second spacer arm 3142. Second spacer arm 3142 may include a medial portion 3142m and a side portion 3142s.

First spacer arm 3141 may be coupled to first implantable segment 3111 and first contact tab 3131. Medial portion 3141m of first spacer arm 3141 may be coupled to proximal portion 3111p of first implantable segment 3111. Side portion 3141s of first spacer arm 3141 may be coupled to first contact tab 3131. Medial portion 3141m and proximal portion 3111p may be coupled by at least one bend 3135. First spacer arm 3141 and first implantable segment 3111 may be formed as a single piece that is bent at bend 3135. Alternatively, first spacer arm 3141 and first implantable segment 3111 may be formed as separate pieces, and medial portion 3141m and proximal portion 3111p may be coupled by a hinge, joint, link, or other coupling. Medial portion 3141m and proximal portion 3111p may be substantially perpendicular. Medial portion 3141m and proximal portion 3111p may form an angle of approximately 30 to 150 degrees. First spacer arm 3141 may be elongate. First spacer arm 3141 may be flat. First spacer arm 3141 may be flexible. First spacer arm 3141 may be straight or curved. First spacer arm 3141 may include one or more bends.

Second spacer arm 3142 may be coupled to second implantable segment 3112 and second contact tab 3132. Medial portion 3142m of second spacer arm 3142 may be coupled to proximal portion 3112p of second implantable segment 3112. Side portion 3142s of second spacer arm 3142 may be coupled to second contact tab 3132. Medial portion 3142m and proximal portion 3112p may be coupled by at least one bend 3135. Second spacer arm 3142 and second implantable segment 3112 may be formed as a single piece that is bent at bend 3135. Alternatively, second spacer arm 3142 and second implantable segment 3112 may be formed as separate pieces, and medial portion 3142m and proximal portion 3112p may be coupled by a hinge, joint, link, or other coupling. Medial portion 3142m and proximal portion 3112p may be substantially perpendicular. Medial portion 3142 in and proximal portion 3112p may form an angle of approximately 30 to 150 degrees. Second spacer arm 3142 may be elongate. Second spacer arm 3142 may be flat. Second spacer arm 3142 may be flexible. Second spacer arm 3142 may be straight or curved. Second spacer arm 3142 may include one or more bends 1145.

First spacer arm 3141 and/or second spacer arm 3142 may include one or more conducting layers. Bends 3145 may include one or more conducting layers. The conducting layers may include stainless steel and/or other conducting material. First spacer arm 3141 and/or second spacer arm 3142 may include one or more insulating layers. bends 3145 may include one or more insulating layers. The insulating layers may include polyimide and/or other insulating material.

First spacer arm 3141 and second spacer arm 3142 may be oriented in different directions. First spacer arm 3141 and second spacer arm 3142 may be oriented in opposite directions. First spacer arm 3141 and second spacer arm 3142 may be oriented in the same direction. First spacer arm 3141 and second spacer arm 3141 may be positioned on opposite sides of implantable body 3110. First spacer arm 3141 and second spacer arm 3142 may be positioned on the same side of implantable body 3110. First spacer arm 3141 and second spacer arm 3142 may be of the same or different lengths and/or shapes.

First spacer arm 3141 and second spacer arm 3142 may be capable of lying flat against and/or parallel to an outside surface of the implantation site. This may allow a portion of in vivo sensing device 3000 outside of the implantation site to have a reduced height and/or size.

First spacer arm 3141 and second spacer arm 3142 may allow first contact tab 3131 and second contact tab 3132 to be spaced apart. First spacer arm 3141 and second spacer arm 3142 may allow a distance and positioning between first contact tab 3131 and second contact tab 3132 to be adjusted. This distance and positioning may provide space to make electrical connections to first contact tab 3131 and second contact tab 3132, such as to an on-body worn device (OBWD). This distance and positioning may provide space to make bulky electrical connections to first contact tab 3131 and/or second contact tab 3132. For example, first contact tab 3131 and/or second contact tab 3132 may require a bulky hermetic or airtight seal when coupled to working electrode 3123.

First spacer arm 3141 and second spacer arm 3142 may have spring-like properties. First spacer arm 3141 and second spacer arm 3142 may be capable of being deformed, and then spring back to their original shapes. First spacer arm 3141 and second spacer arm 3142 may be configured to bias implantable body 3110 back into the implantation site when implantable body 3110 travels at least partially out of the implantation site. First spacer arm 3141 and second spacer arm 3142 may be configured to bias implantable body 3110 in a distal direction when implantable body 3110 travels in a proximal direction. This travel may help to refresh interstitial fluid and/or displace any blood surrounding implantable body 3110. First implantable segment 3111 and second implantable segment 3112 may have sufficient stiffness to be pushed back into the implantation site instead of buckling or bunching in an accordion-like fashion outside of the implantation site. First spacer arm 3141 and second spacer arm 3142 may have sufficient fatigue strength to last a design life of sensor assembly 3100.

Figure 11A:
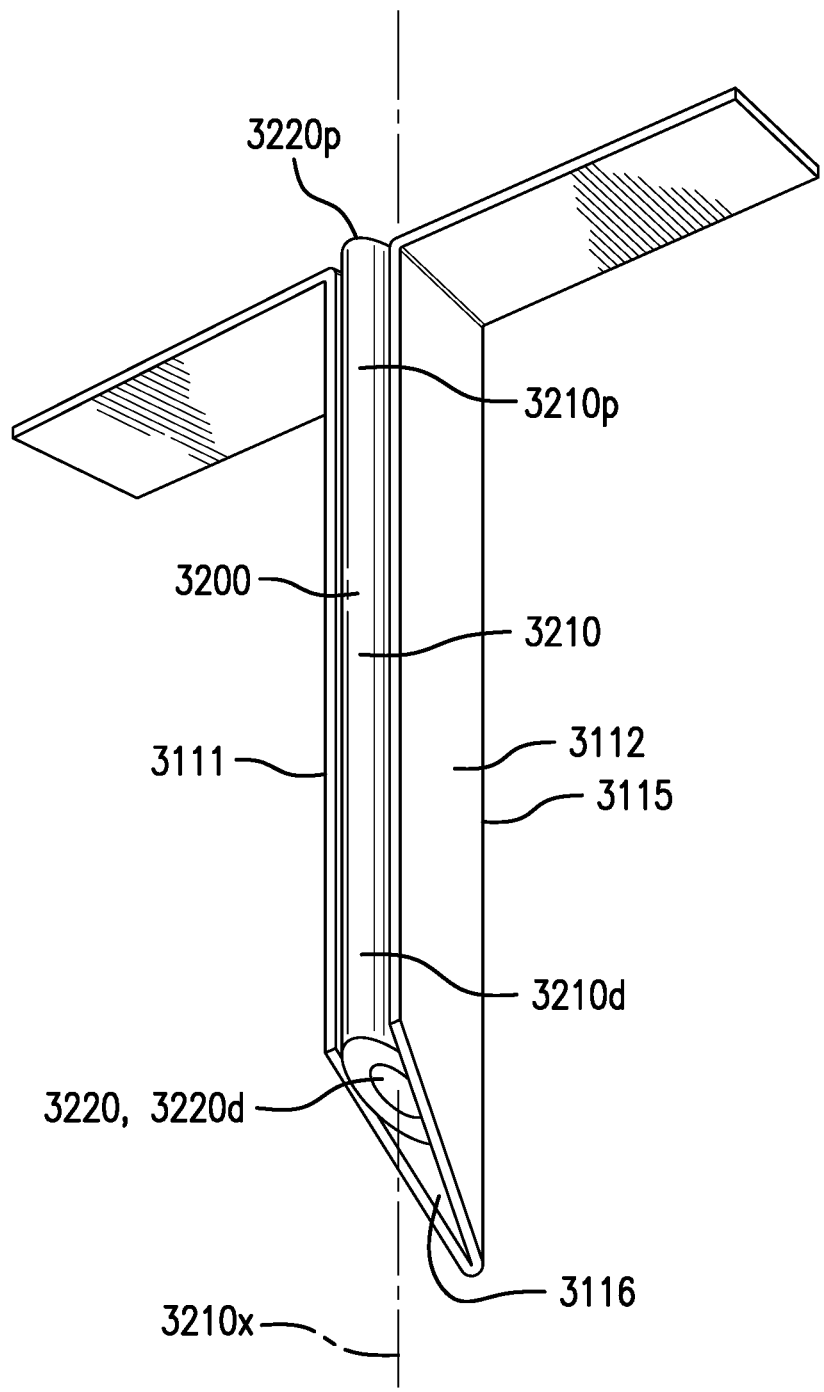
FIG. 11A shows in vivo sensing device 3000 with a catheter 3200.

Sensor assembly 3100 may be used with a catheter assembly 3200, as shown in FIG. 11A. Catheter assembly 3200 is configured to be at least partially placed in the implantation site. Catheter assembly 3200 includes at least one catheter 3210.

Catheter 3210 includes a proximal portion 3210$p$, a distal portion 3210$d$, and a longitudinal axis 3210$x$. Catheter 3210 may have a cross section that is circular. Alternatively, catheter 3210 may have a cross section that is oval, square, triangular, or other suitable shape. Catheter 3210 may be flexible.

Catheter 3210 may be at least partially positioned in space 3116 between first implantable segment 3111 and second implantable segment 3112.

Catheter 3210 may include an infusion lumen 3220 formed in catheter 3210. Infusion lumen 3220 may have a distal end 3220$d$ that is open or closed. Catheter 3210 may include one or more infusion ports formed in catheter 3210. Infusion ports may be in fluid communication with infusion lumen 3220. Infusion ports may be formed in a side of catheter 3210.

In vivo sensing device 3000 may be used with an insertion sharp 3300. Insertion sharp 3300 may include a needle, a flat lancet, or other suitable sharp.

Insertion sharp 3300 includes a proximal portion 3300$p$ and a distal portion 3300$d$.

Figure 11B:
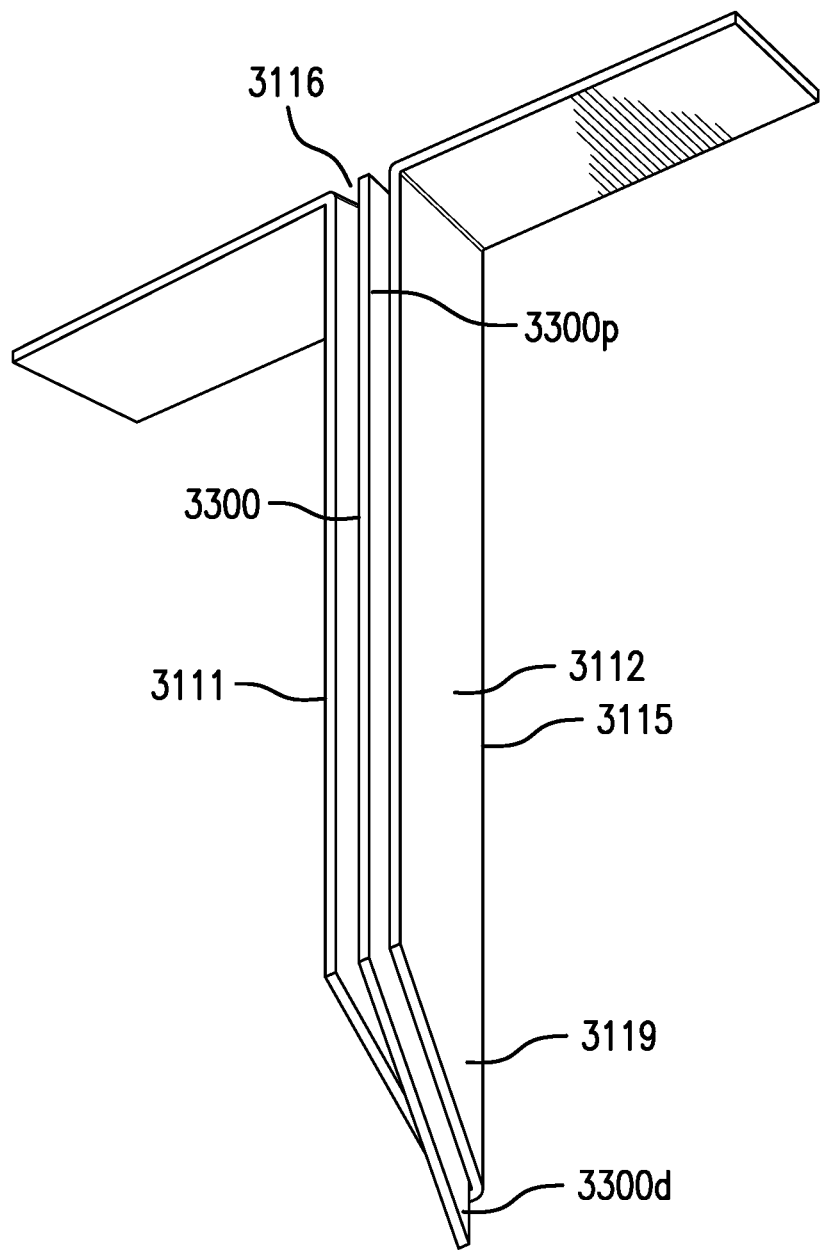
FIG. 11B shows in vivo sensing device 3000 with an insertion sharp 3300.

Insertion sharp 3300 may be at least partially placed in space 3116 between first implantable segment 3111 and second implantable segment 3112, as shown in FIG. 11B. Distal portion 3300$d$ of insertion sharp 3300 may extend beyond tip 3119.

Insertion sharp 3300 may be used with in vivo sensing device 3000 having catheter assembly 3200. Insertion sharp 3300 may be placed in infusion lumen 3220 of catheter 3210. Distal portion 3300$d$ of insertion sharp 3300 may extend beyond distal portion 3210$d$ of catheter 3210.

Alternatively, insertion sharp 3300 may be placed along a side of first implantable segment 3111 or second implantable segment 3112.

Figure 12A:
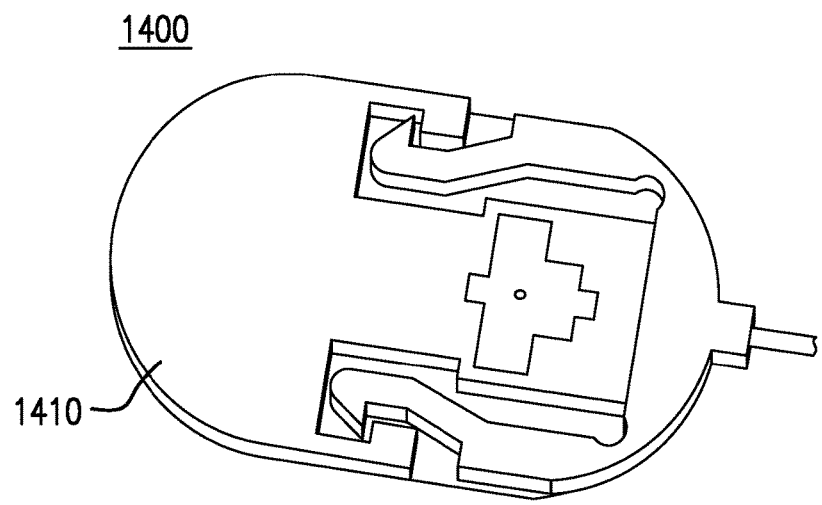
FIGS. 12A-12B show one embodiment of an on-body worn device (OBWD) 1400.
Figure 12B:
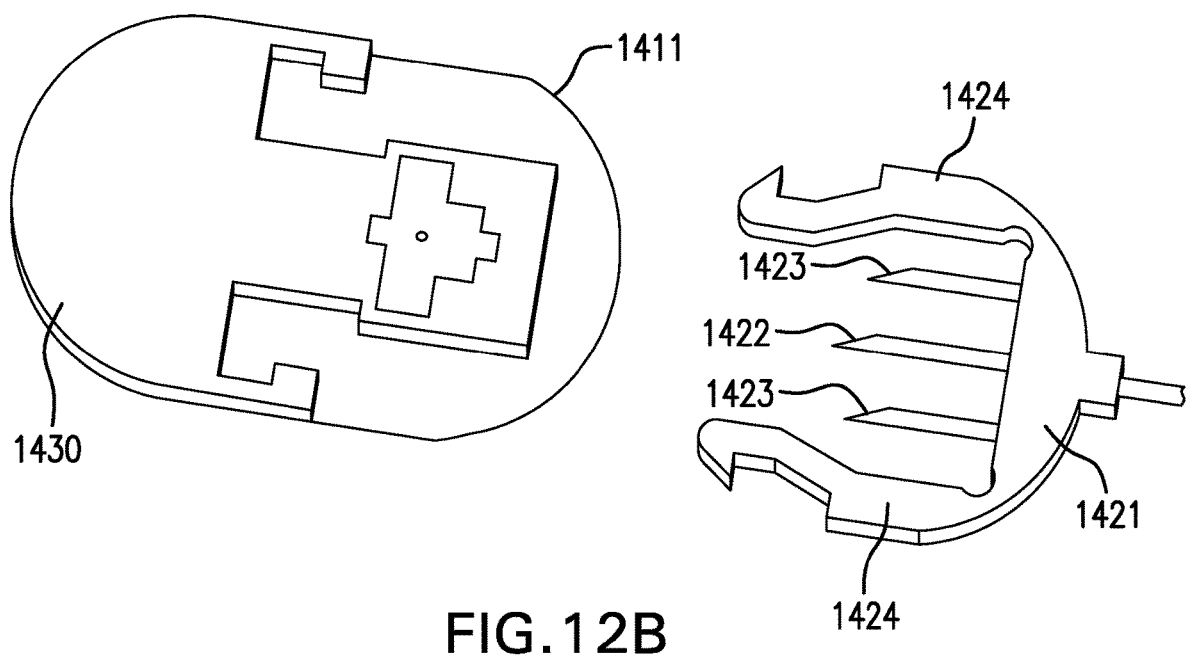
Figure 13A:
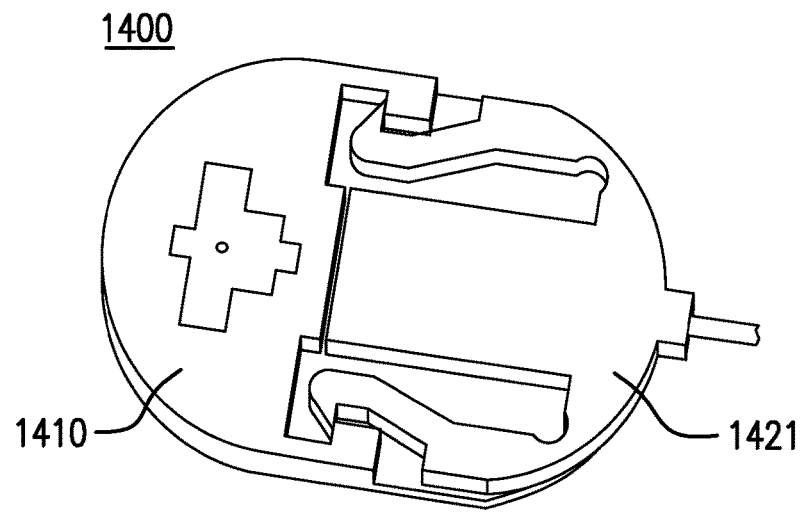
FIGS. 13A-13B show another embodiment of an OBWD 1400.
Figure 13B:
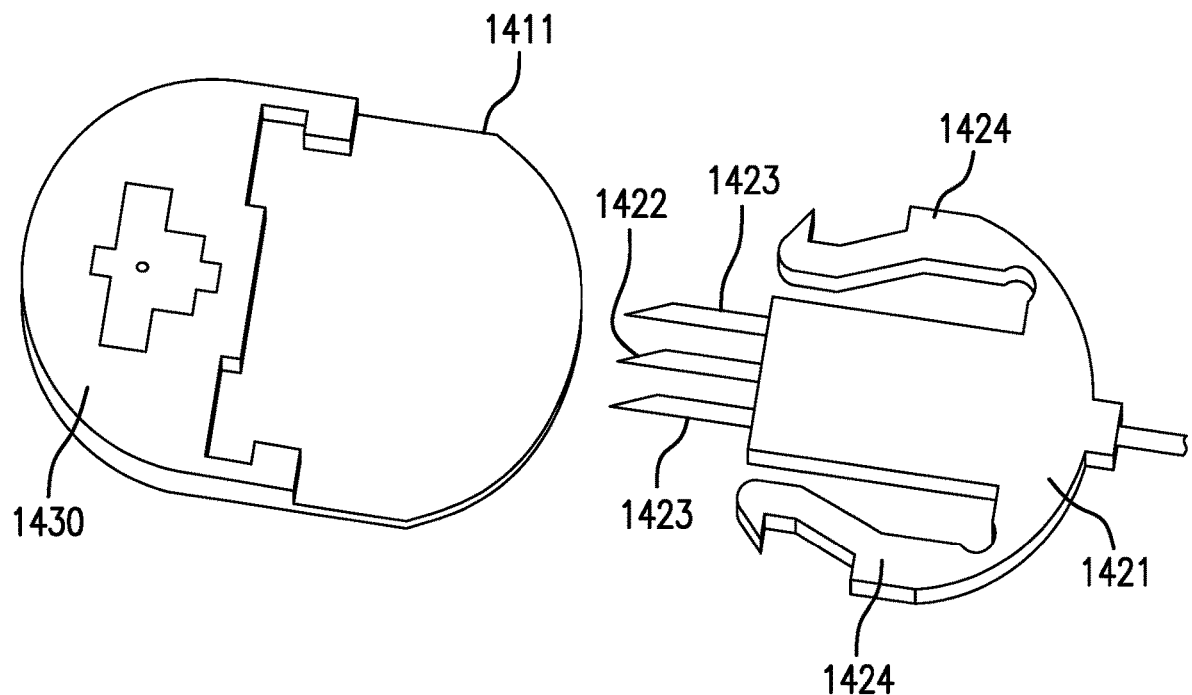

FIGS. 12A-12B show one embodiment of an on-body worn device (OBWD) 1400. FIGS. 12A-12B show another embodiment of an OBWD 1400.

In vivo sensing devices 1000, 2000, and 3000 may include an on-body worn device (OBWD) 1400.

OBWD 1400 may include a housing 1410. Housing 1410 may include a base plate 1411.

OBWD 1400 may include a connector 1421. Connector 1421 may include an infusion connector 1422, one or more electrical connectors 1423, and coupling arms 1424.

Infusion connector 1422 may include substantially fluid-tight connectors, such as a needle which may be inserted into a needle port. Electrical connectors 1423 may include electrically conductive connectors, such as metal pins which may be inserted into conductive elastomers. Coupling mechanism 1424 may be any suitable coupling mechanism, such as clips which fit into tabs.

OBWD may include electronics 1430. Electronics 1430 may include a printed circuit board and/or circuitry.

Figure 14A:
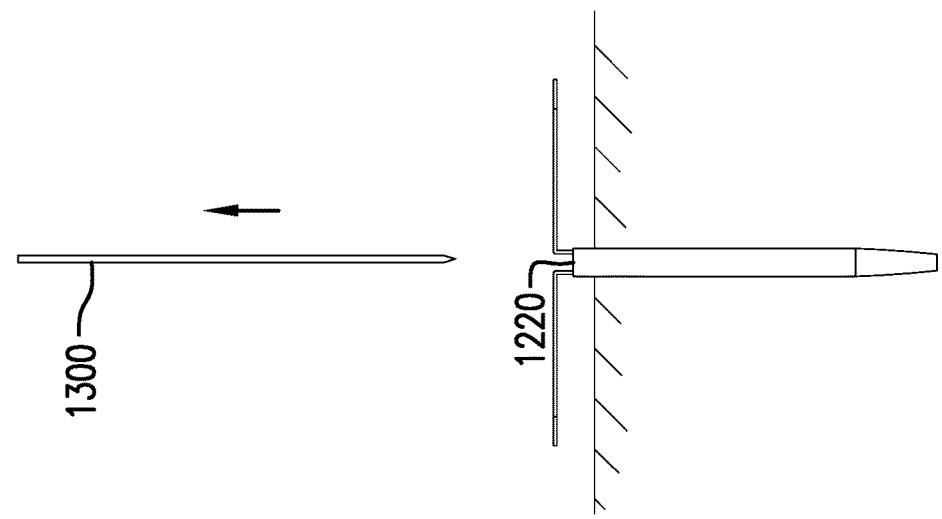
FIGS. 14A-14C show one embodiment of a method for implanting in vivo sensing device 1000.
Figure 14B:
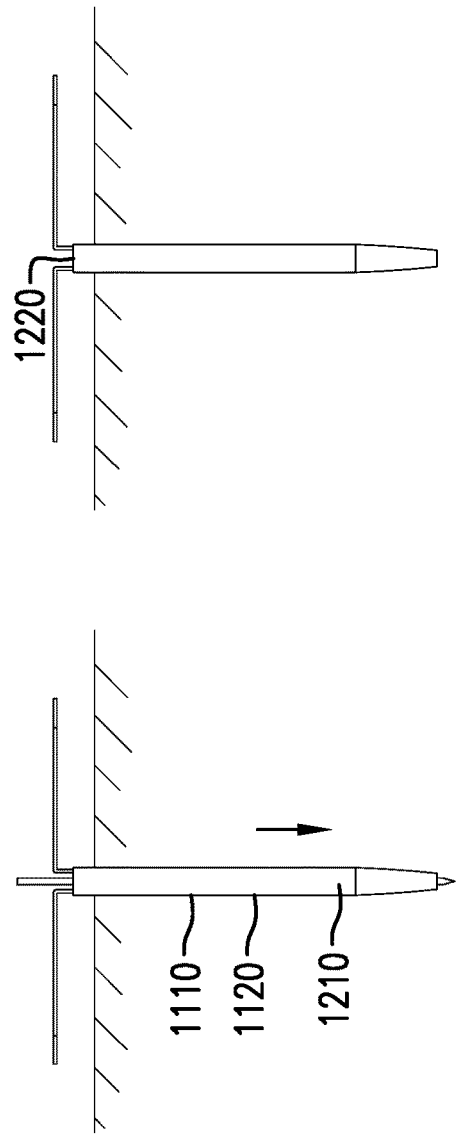
Figure 14C:
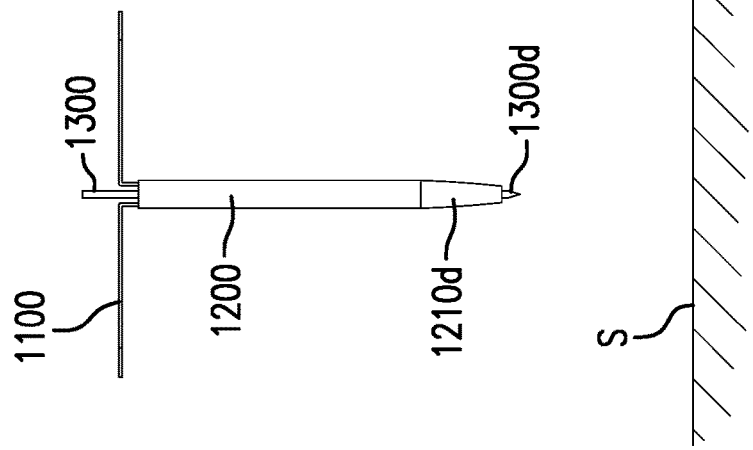

FIGS. 14A-14C show one embodiment of a method for implanting sensing and infusion device 1000.

FIG. 14A shows sensor assembly 1100 and catheter assembly 1200. Insertion sharp 1300 is placed in infusion lumen 1220 of catheter 1210. Distal portion 1300$d$ of insertion sharp 1300 extends beyond distal portion 1210$d$ of catheter 1210.

FIG. 14B shows implanting sensor assembly 1100 and catheter assembly 1200. Surface S may be the skin, or the surface of a blood vessel, organ, or other tissue. Distal portion 1300$d$ of insertion sharp 1300 punctures surface S. Implantable segments 1110 and sensor 1120 are at least partially implanted in the implantation site. Catheter 1210 is also at least partially implanted in the implantation site.

FIG. 14C shows removing insertion sharp 1300. Infusion lumen 1220 may allow blood and/or other bodily fluids to escape, reducing the likelihood of wetting or other effects on sensor 1120.

Figure 15A:
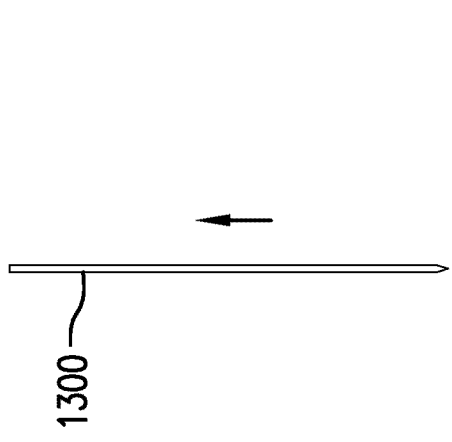
FIGS. 15A-15C show another embodiment of a method for implanting in vivo sensing device 1000.
Figure 15B:
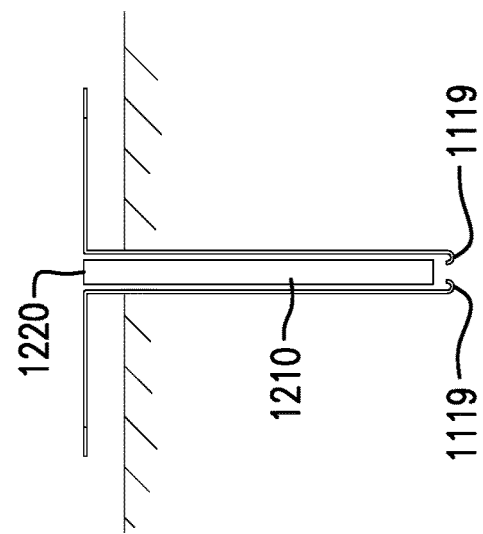
Figure 15C:
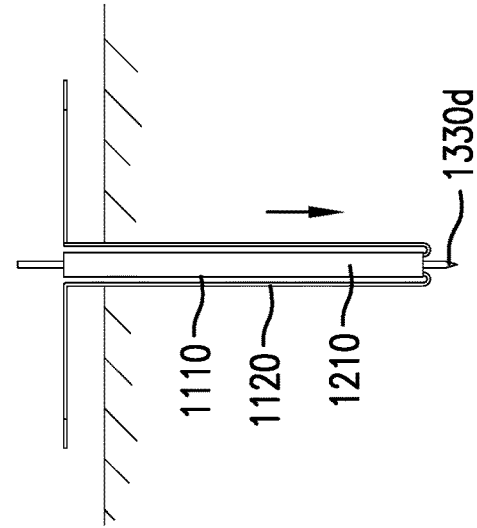

FIGS. 15A-15C show another embodiment of a method for implanting sensing and infusion device 1000.

FIG. 15A shows sensor assembly 1100 having implantable segments 1110 with hooks 1119. Insertion sharp 1300 is in infusion lumen 1220 of catheter 1210. Distal portion 1300*d* of insertion sharp 1300 extends beyond distal portion 1210*d* of catheter 1210. Hooks 1119 may be hooked into distal portion 1300*d* of insertion sharp 1300.

FIG. 15B shows implanting sensor assembly 1100 and catheter assembly 1200. Surface S may be the skin, or the surface of a blood vessel, organ, or other tissue. Distal portion 1300*d* of insertion sharp 1300 punctures surface S. Implantable segments 1110 and sensor 1120 are at least partially implanted in the implantation site. Catheter 1210 is also at least partially implanted in the implantation site.

FIG. 15C shows removing insertion sharp 1300. Hooks 1119 may be left where they are, or they may be pulled back and hooked into distal end 1220*d* of infusion lumen 1220. Infusion lumen 1220 may allow blood and/or other bodily fluids to escape, reducing the likelihood of wetting or other effects on sensor 1120.

Sensing and infusion device 1000 may both (1) sense at least one analyte and/or physiological property and (2) deliver at least one infusate, using a single implantation site. A single implantation site may use less space and may cause less trauma.

Figure 16A:
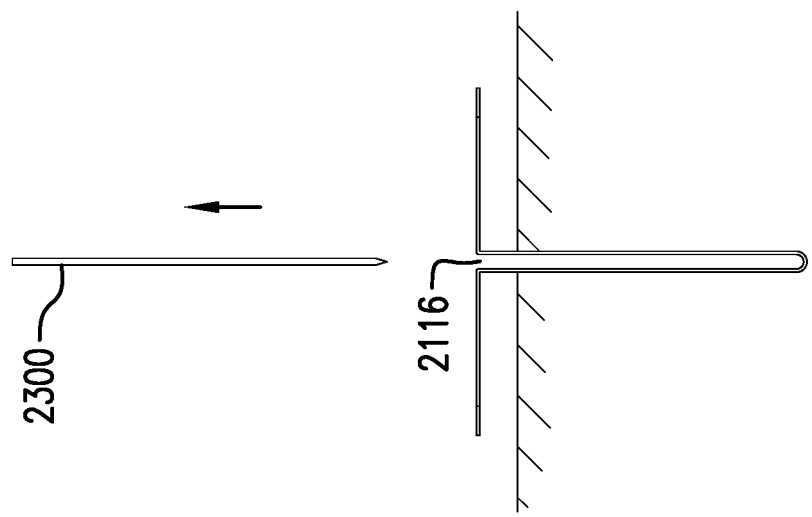
FIGS. 16A-16C show one embodiment of a method for implanting in vivo sensing device 2000.
Figure 16B:
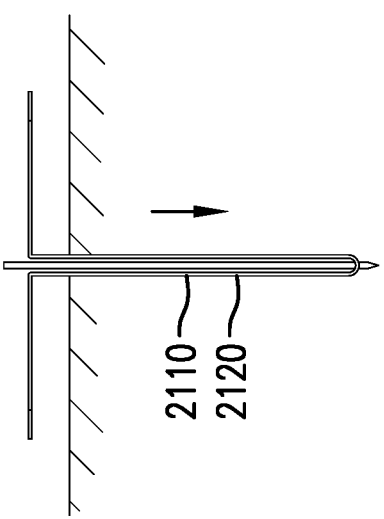
Figure 16C:
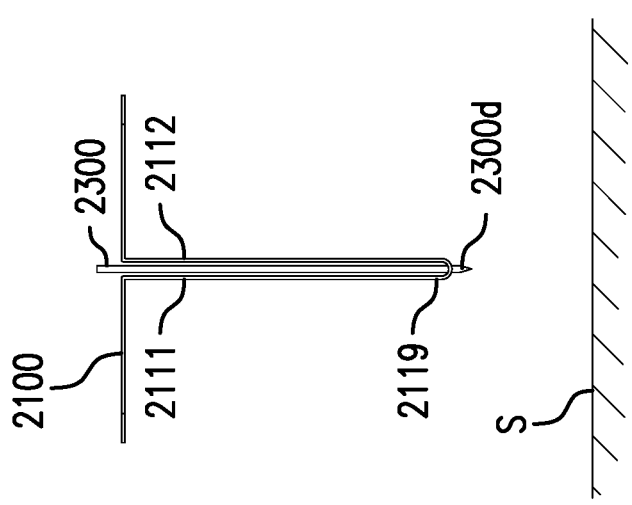

FIGS. 16A-16C show one embodiment of a method for implanting in vivo sensing device 2000.

FIG. 16A shows sensor assembly 2100. Insertion sharp 2300 is placed between first implantable segment 2111 and second implantable segment 2112. Distal portion 2300*d* of insertion sharp 2300 is placed in opening 2118, and extends beyond tip 2119.

FIG. 16B shows implanting sensor assembly 2100. Surface S may be the skin, or the surface of a blood vessel, organ, or other tissue. Distal portion 2300*d* of insertion sharp 2300 punctures surface S. Implantable body 2110 and sensor 2120 are at least partially implanted in the implantation site.

FIG. 16C shows removing insertion sharp 2300. Space 2116 may allow blood and/or other bodily fluids to escape, reducing the likelihood of wetting or other effects on sensor 2120.

Figure 17A:
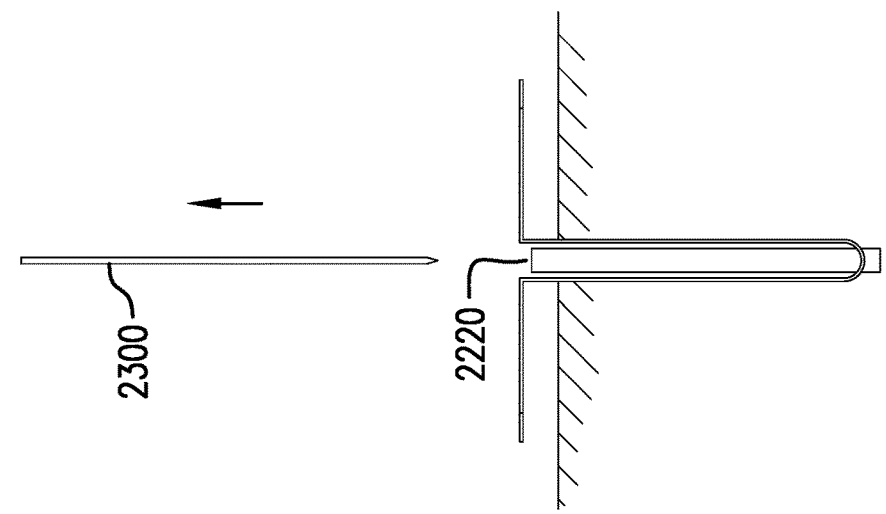
FIG. 17A-17C show another embodiment of a method for implanting in vivo sensing device 2000.
Figure 17B:
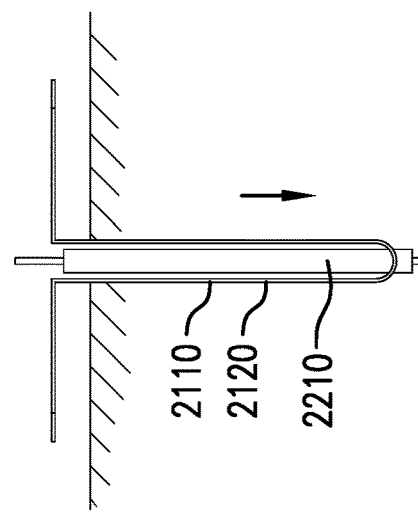
Figure 17C:
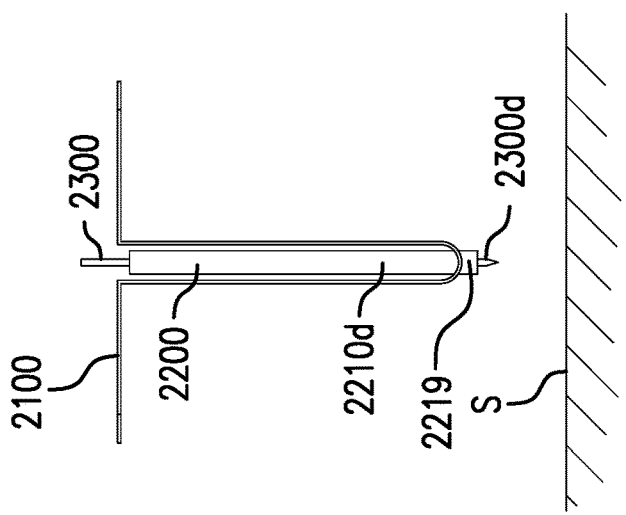

FIG. 17A-17C show another embodiment of a method for implanting in vivo sensing device 2000.

FIG. 17A shows sensor assembly 2100 and catheter assembly 2200. Insertion sharp 2300 is placed in infusion lumen 2220 of catheter 2210. Distal portion 2300*d* of insertion sharp 2300 extends beyond distal portion 2210*d* of catheter 2210.

FIG. 17B shows implanting sensor assembly 2100 and catheter assembly 2200. Surface S may be the skin, or the surface of a blood vessel, organ, or other tissue. Distal portion 2300*d* of insertion sharp 2300 punctures surface S. Implantable body 2110 and sensor 2120 are at least partially implanted in the implantation site. Catheter 2210 is also at least partially implanted in the implantation site.

FIG. 17C shows removing insertion sharp 2300. Infusion lumen 2220 may allow blood and/or other bodily fluids to escape, reducing the likelihood of wetting or other effects on sensor 2120.

In vivo sensing device 2000, when used with catheter assembly 2200, may both (1) sense at least one analyte and/or physiological property and (2) deliver at least one infusate, using a single implantation site. A single implantation site may use less space and may cause less trauma.

FIGS. 18A-18B show one embodiment of a method for implanting in vivo sensing device 3000.

FIG. 18A shows sensor assembly 3100. Implantable body 3110 includes a tip 3119 that is pointed and/or sharpened.

FIG. 18B shows implanting sensor assembly 3100. Surface S may be the skin, or the surface of a blood vessel, organ, or other tissue. Tip 3119 punctures surface S. Implantable body 3110 and sensor 3120 are at least partially implanted in the implantation site.

Space 3116 may allow blood and/or other bodily fluids to escape, reducing the likelihood of wetting or other effects on sensor 3120.

Figure 19C:
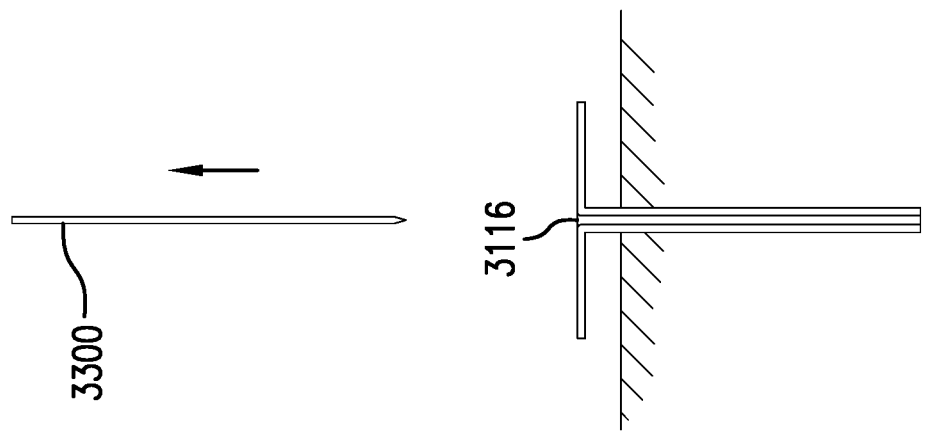
FIGS. 19A-19C show one embodiment of a method for implanting in vivo sensing device 3000.
Figure 19B:
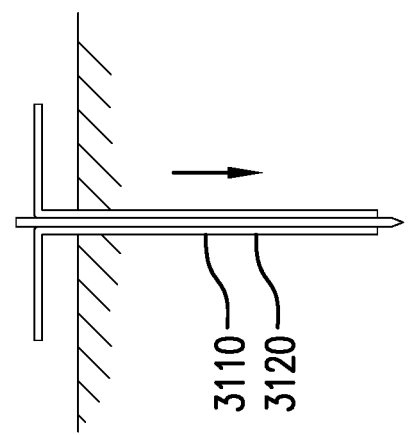
Figure 19A:
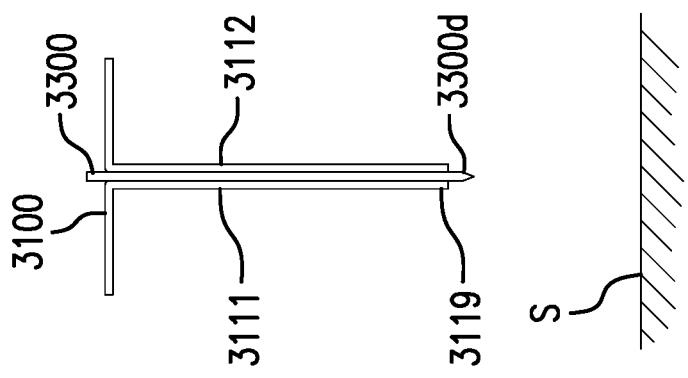

FIGS. 19A-19C show one embodiment of a method for implanting in vivo sensing device 3000.

FIG. 19A shows sensor assembly 3100. Insertion sharp 3300 is placed in space 3116. Distal portion 3300*d* of insertion sharp 3300 extends beyond tip 3119.

FIG. 19B shows implanting sensor assembly 3100. Surface S may be the skin, or the surface of a blood vessel, organ, or other tissue. Distal portion 3300*d* of insertion sharp 3300 punctures surface S. Implantable body 3110 and sensor 3120 are at least partially implanted in the implantation site.

FIG. 19C shows removing insertion sharp 3300. Space 3116 may allow blood and/or other bodily fluids to escape, reducing the likelihood of wetting or other effects on sensor 3120.

In vivo sensing device 3000, when used with catheter assembly 3200, may both (1) sense at least one analyte and/or physiological property and (2) deliver at least one infusate, using a single implantation site. A single implantation site may use less space and may cause less trauma.

"Sensor" as used herein is any device, component or combination that (1) detects/records/communicates information about an event or the presence/absence of a particular analyte, thing or property in its sensing environment, and/or (2) indicates an absolute or relative value/quantity/concentration, or rate of change, of that analyte, thing or property.

The sensor may be based on any principle and can be an electrochemical sensor, an impedance sensor, an acoustic sensor, a radiation sensor, a flow sensor, an immunosensor, or the like. For in-vivo use in medical and veterinary applications, the sensor may be used to detect, measure and/or record (1) one or more analytes, such as glucose, lactate, oxygen, ketone, or any other marker(s) of a disease or medical condition, and (2) one or more of properties, such as temperature, pressure, perfusion rate, hydration or pH.

The use of the sensing and infusion devices described herein are also not limited to a specific physical structure of the sensor or infusion device. For example, in a glucose sensing application, the sensor may be similar to a conventional glucose sensors that use a glucose-limiting membrane and generally based on the principles of one dimensional diffusion, where glucose and oxygen travel in the same general direction before reacting within the enzyme layer (e.g., glucose oxidase) at the working electrode. Or the sensor can use any other non-conventional structure, based on a glucose sensor without a glucose limiting membrane and/or any structure that takes advantage of multidimensional diffusion.

The combined sensing/infusion devices described herein may be applied in any medical or veterinary application. This includes the treatment/management of diabetes and the development of the artificial pancreas, by having a single point of insertion for infusion and sensing that reduces trauma to the patient; the embodiments described herein would allow one or more glucose sensors to be placed within one or more infusion catheters that deliver one or more drugs/agents/infusates (e.g., glucagon and insulin). The combined sensing/infusion devices can also be used to support organ failure with sensor augmented drug delivery, by combining an infusion catheter with sensors (e.g., sensors for lactate and oxygen) and directly inserting the device in the vasculature and tissue of failing organs, thereby providing high dose, targeted therapy designed to normalize mitochondria function. Alternatively, it can also be used to monitor metabolic changes in current or former cancer patients and tailor treatment compositions based on metabolic profiling specific to a cancer type.

While the foregoing has been with reference to particular embodiments of the invention, it will be appreciated by those skilled in the art that changes in these embodiments may be made without departing from the principles and spirit of the invention.

What is claimed is:

1. A sensing and infusion device comprising:
a first sensor strip having at least one working electrode; and
a catheter including:
an inner infusion lumen;
a first elongate sensor channel formed on an outer surface of the catheter external to the inner infusion lumen, the first sensor channel being open to an exterior of the catheter and configured to receive and hold the first sensor strip; and
an opening formed in a wall of the catheter separating the inner infusion lumen from the first sensor channel that provides access into the inner infusion lumen, the opening allowing for a distal portion of the first sensor strip to pass into the inner infusion lumen such that a distal end of the first sensor strip is disposed within the inner infusion lumen and the at least one working electrode remains within the first elongate sensor channel.

2. The device of claim 1, wherein the first sensor channel has a longitudinal dimension that is parallel with an axis of the inner infusion lumen.

3. The device of claim 1, wherein a second elongate sensor channel is formed within the inner infusion lumen and is configured to have a second sensor strip disposed therein.

4. The device of claim 1, wherein:
the catheter further includes a second elongate sensor channel formed on the outer surface of the catheter external to the infusion lumen;
the second sensor channel is open to the exterior of the catheter and configured to receive and hold a second sensor strip; and
the second sensor channel has a longitudinal dimension that is parallel with an axis of the infusion lumen.

5. The device of claim 4, wherein:
the first sensor strip has a first right-angle bend and a first proximal portion that is proximal of the first right-angle bend and projects radially away from the axis of the inner infusion lumen in a first radial direction; and
the second sensor strip has a second right-angle bend and a second proximal portion that is proximal of the second right-angle bend and projects radially away from the axis of the inner infusion lumen in a second radial direction that is opposite the first radial direction.

6. The device of claim 1, wherein the first sensor strip includes a sensor that is associated with the distal portion of the first sensor strip and is configured to be disposed within the inner infusion lumen when the distal portion of the first sensor strip is passed through the opening.

7. The device of claim 6, wherein the sensor is a pressure sensor configured to detect a pressure of an infusate disposed within the inner infusion lumen.

8. The device of claim 1, wherein the first sensor channel is open to the exterior of the catheter along an entire length of the first sensor channel.

9. The device of claim 1, wherein the first sensor channel extends along an entire length of the catheter.

10. The device of claim 1, further comprising an annular, radially-projecting backflow barrier covering a portion of the first sensor channel distal to one or more sensors disposed on the first sensor strip and exposed in the first sensor channel.

* * * * *